US009110065B2

(12) United States Patent
Walfish et al.

(10) Patent No.: US 9,110,065 B2
(45) Date of Patent: Aug. 18, 2015

(54) METHODS AND COMPOSITIONS FOR THE DIAGNOSIS AND TREATMENT OF THYROID CANCER

(76) Inventors: Paul Walfish, Toronto (CA); Ranju Ralhan, Thornhill (CA)

( * ) Notice: Subject to any disclaimer, the term of this patent is extended or adjusted under 35 U.S.C. 154(b) by 0 days.

(21) Appl. No.: 13/464,494

(22) Filed: May 4, 2012

(65) Prior Publication Data

US 2012/0214165 A1     Aug. 23, 2012

Related U.S. Application Data

(63) Continuation-in-part of application No. 13/497,441, filed as application No. PCT/CA2010/001503 on Sep. 21, 2010, now abandoned.

(60) Provisional application No. 61/244,173, filed on Sep. 21, 2009.

(51) Int. Cl.
*C12Q 1/68* (2006.01)
*G01N 33/574* (2006.01)
*C07K 16/30* (2006.01)

(52) U.S. Cl.
CPC .......... *G01N 33/57407* (2013.01); *C07K 16/30* (2013.01); *C12Q 1/6886* (2013.01); *C07K 2317/73* (2013.01); *C12Q 2600/158* (2013.01)

(58) Field of Classification Search
None
See application file for complete search history.

(56) References Cited

U.S. PATENT DOCUMENTS

2011/0104062 A1   5/2011   Siu
2011/0275065 A1   11/2011  Walfish
2011/0275530 A1   11/2011  Walfish

FOREIGN PATENT DOCUMENTS

WO    WO 2007141029 A1 *  12/2007

OTHER PUBLICATIONS

Balzar et al., Journal of Molecular Medicine, 1999, vol. 77, pp. 699-712.*
Maetzel et al., Nature Cell Biology, 2009, vol. 11, 162-171 and 14 pages of supplemental pages.*
Aberle et al, beta-catenin is a target for the ubiquitin-proteasome pathway, *The Embo Journal*, Jul. 1997, 16(13):3797-3804.
Al-Hajj M, et al., Prospective identification of tumorigenic breast cancer cells, *Proceedings of the National Academy of Sciences USA*. Jan. 2003;100(7):3983-8.
Antolovic D, et al, Heterogeneous detection of circulating tumor cells in patients with colorectal cancer by immunomagnetic enrichment using different EpCAM-specific antibodies, *BMC Biotechnology*. Apr. 2010; 10:35.
Baeuerle PA, EpCAM (CD326) finding its role in cancer, *British Journal of Cancer*, Jan. 2007, 96(3):417-23.

Balzar et al, Epidermal growth factor-like repeats mediate lateral and reciprocal interactions of Ep-CAM molecules in homophilic adhesions, *Molecular and Cellular Biology*, Apr. 2001, 21(7):2570-80.
Bian YS, et al, Nuclear accumulation of beta-catenin is a common and early event during neoplastic progression of Barrett esophagus, *American Journal of Clinical Pathology*. Oct. 2000; 114(4):583-90.
Cadigan KM, Wnt-beta-catenin signaling, *Current Biology*, Oct. 2008, 18:20, R943-7.
Chaudry MA, et al, EpCAM an immunotherapeutic target for gastrointestinal malignancy: current experience and future challenges, *British Journal of Cancer*. Feb. 2007; 96:1013-9.
Cimino A, Halushka M, Illei P, Wu X, Sukumar S, Argani P. Epithelial cell adhesion molecule (EpCAM) is overexpressed in breast cancer metastases. *Breast Cancer Research and Treatment*. Oct. 2010; 123(3):701-8, Epub Dec. 11, 2009.
El-Sahwi K et al, Overexpression of EpCAM in uterine serous papillary carcinoma: implications for EpCAM-specific immunotherapy with human monoclonal antibody adecatumumab (MT201), *Molecular Cancer Therapy*. Jan. 2010;9(1):57-66.
Gujral TS, et al, A novel RET kinase-beta-catenin signaling pathway contributes to tumorigenesis in thyroid carcinoma, *Cancer Research*. Mar. 2008; 68(5):1338-46.
Ishida K, et al, Nuclear localization of beta-catenin involved in precancerous change in oral leukoplakia, *Molecular Cancer*. Oct. 2007; 6:62.
Jemal A, et al, Cancer Statistics, 2008 *CA: A Cancer Journal for Clinicians*. Feb. 2008; 58(2):71-96.
Lantsov D, et all, Cyclin D1 overexpression in thyroid papillary microcarcinoma: its association with tumour size and aberrant beta-catenin expression, *Histopathology*. Jan. 2005; 47:248-56.
Li H, et al, beta-Catenin signaling: therapeutic strategies in oncology, *Cancer Biology and Therapy*. Oct. 2002; 1(6):621-5.
Litvinov SV, et al, Epithelial cell adhesion molecule (Ep-CAM) modulates cell-cell interactions mediated by classic cadherins, *The Journal of Cell Biology*. Dec. 1997; 139(5)1337-48.
MacDonald BT et al, Wnt/beta-catenin signaling: components, mechanisms, and diseases, *Developmental Cell*, Jul. 2009, 1, 9-26.
Maetzel D et al, Nuclear signalling by tumour-associated antigen EpCAM, *Nature Cell Biology*. Jan. 2009; 11(2):162-71.
Munz M, et al, The Emerging Role of EpCAM in Cancer and Stem Cell Signaling, *Cancer Research*. Jul. 2009; 69(14):5627-9.
Münz M, et al, The carcinoma-associated antigen EpCAM upregulates c-myc and induces cell proliferation, *Oncogene*. Jun. 2004; 23(34):5748-58.
Nappi TC, et al, Identification of Polo-like kinase 1 as a potential therapeutic target in anaplastic thyroid carcinoma, *Cancer Res*. Feb. 2009; 69(5):1916-23.

(Continued)

*Primary Examiner* — Michele K Joike
*Assistant Examiner* — Mindy G Brown
(74) *Attorney, Agent, or Firm* — Santosh K. Chari; Blake, Cassels & Graydon LLP

(57) ABSTRACT

Methods for detecting, diagnosing and monitoring thyroid cancer in a subject are described comprising measuring in a sample from the subject markers including Ep-ICD and EpEX. The invention also provides kits and compositions for carrying out the methods of the invention.

14 Claims, 45 Drawing Sheets

(56) References Cited

OTHER PUBLICATIONS

O'Brien CA, et al, A human colon cancer cell capable of initiating tumour growth in immunodeficient mice, *Nature.* Jan. 2007; 445(7123):106-10.

Ogasawara N, et al, Mutations and nuclear accumulation of beta-catenin correlate with intestinal phenotypic expression in human gastric cancer, *Histopathology.* Dec. 2006; 49(6):612-21.

Raffel A, et al, Increased EpCAM expression in malignant insulinoma: potential clinical implications, *European Journal of Endocrinology.* Feb. 2010; 162(2):391-8.

Ralhan et al, Discovery and verification of head-and-neck cancer biomarkers by differential protein expression analysis using iTRAQ labeling, multidimensional liquid chromatography, and tandem mass spectrometry, *Molecular & Cellular Proteomics.* Jun. 2008;7(6):1162-73. Epub Mar. 13, 2008.

Reis EM, et al, Large-scale transcriptome analyses reveal new genetic marker candidates of head, neck, and thyroid cancer, *Cancer Research.* Mar. 2005, 65(5):1693-9.

Ricci-Vitiani L, et al, Identification and expansion of human colon-cancer-initiating cells, *Nature.* Jan. 2007; 445(7123):111-5.

Rocha AS, et al, E-cadherin loss rather than beta-catenin alterations is a common feature of poorly differentiated thyroid carcinomas. *Histopathology.* Jun. 2003; 42(6):580-7.

Salvatore G, et al, A cell proliferation and chromosomal instability signature in anaplastic thyroid carcinoma, *Cancer Research,* Nov. 2007;67:10148-58.

Smallridge RC, et al, Anaplastic thyroid cancer: molecular pathogensis and emerging therapies, *Endocrine Related Cancer.* Mar. 2009; 16(1):17-44.

Takayama T, et al, Beta-catenin expression in human cancers, *The American Journal of Pathology,* Jan. 1996; 148(1):39-46.

Terris B, et al, EpCAM, a new marker for cancer stem cells in hepatocellular carcinoma, Journal of Hepatology .Feb. 2010; 52(2):280-1.

Trzpis M, et al. Epithelial cell adhesion molecule: more than a carcinoma marker and adhesion molecule, Epithelial Cell Adhesion Molecule, *American Journal of Pathology.* Aug. 2007; 171(2):386-95.

Went P, et al, Frequent high-level expression of the immunotherapeutic target Ep-CAM in colon, stomach, prostate and lung cancers, *British Journal of Cancer.* Jan. 2006; 94(1):128-35.

Ensinger et al., EpCAM overexpression in thyroid carcinomas: a histopathological study of 121 cases, Journal of Immunotherapy, Sep. 2006, 29(5) 569-573.

Ruf et al., Characterisation of the new EpCAM-specific antibody HO-3: implications for trifunctional antibody immunotherapy of cancer, British Journal of Cancer, Jul. 2007, 97(3):315-321.

Wiseman S M et al, Annals of Surgical Oncology, 2006, vol. 14, pp. 719-729.

Wiseman S M et al., Archives of Surgery, 2007, vol. 142, pp. 717-729.

Garcia-Rostan G et al, American Journal of Pathology, 2001, vol. 158, pp. 987-996.

\* cited by examiner

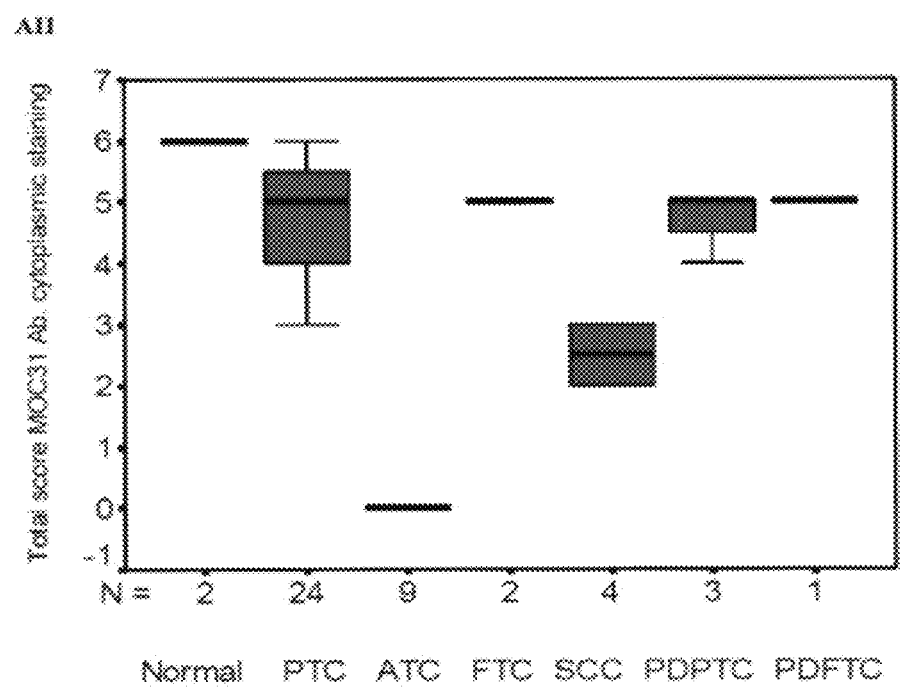

AIII

Figure 3
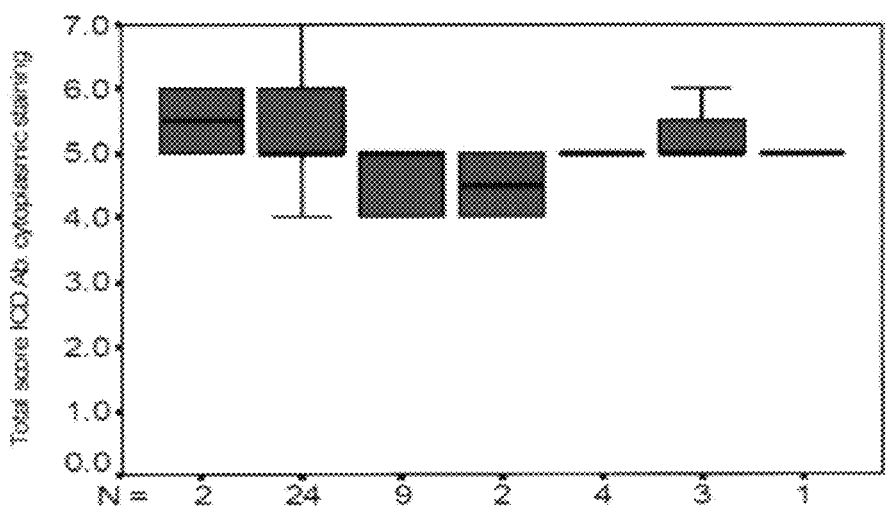
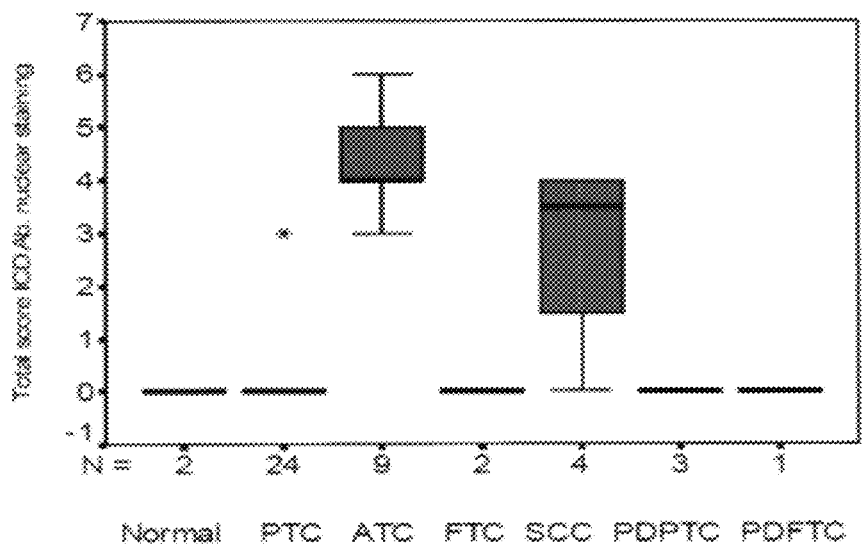

Figure 3
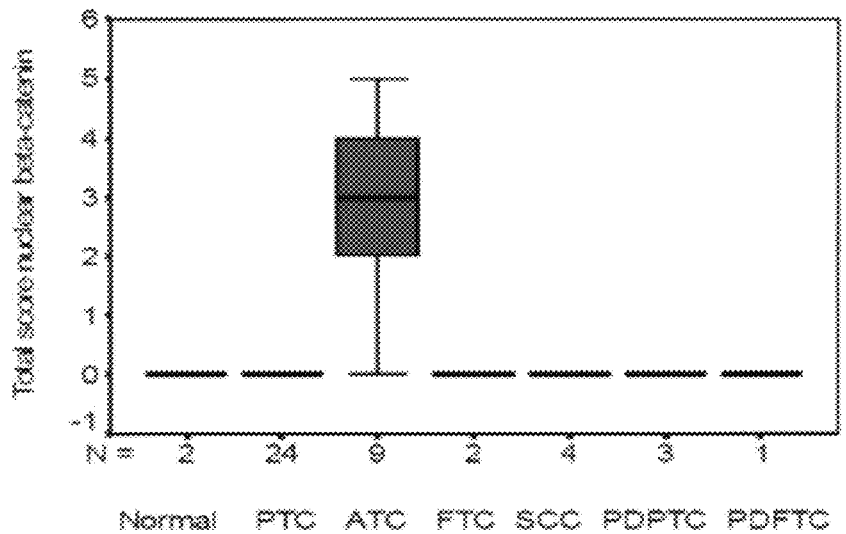
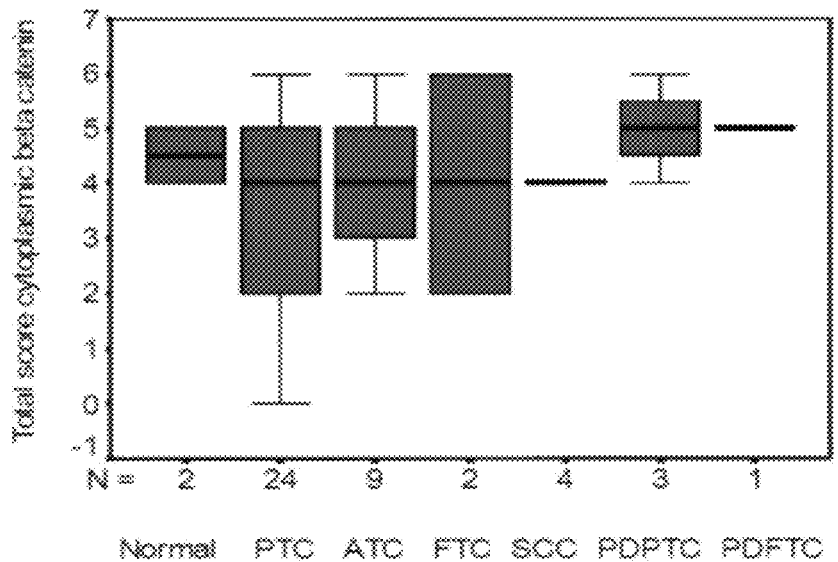

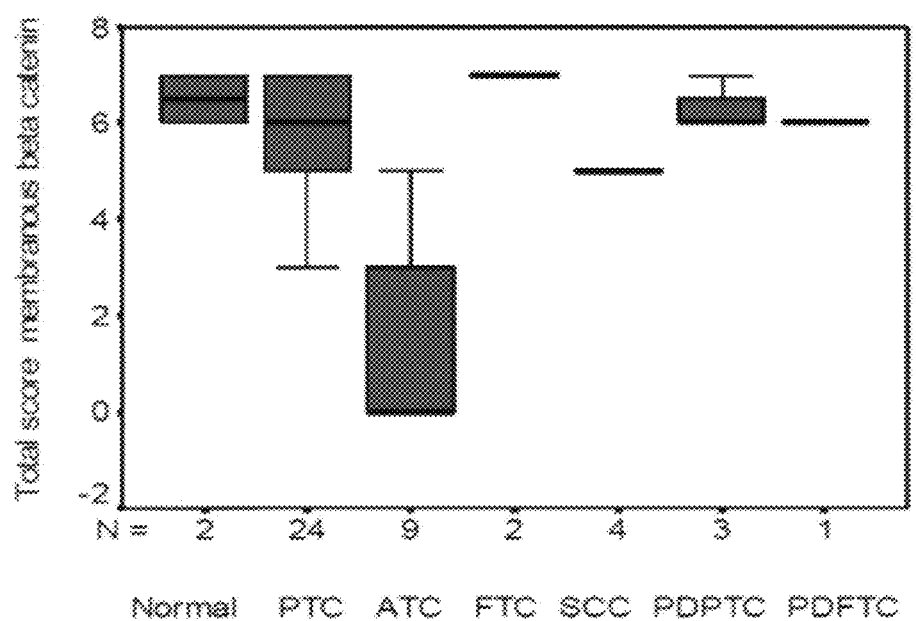

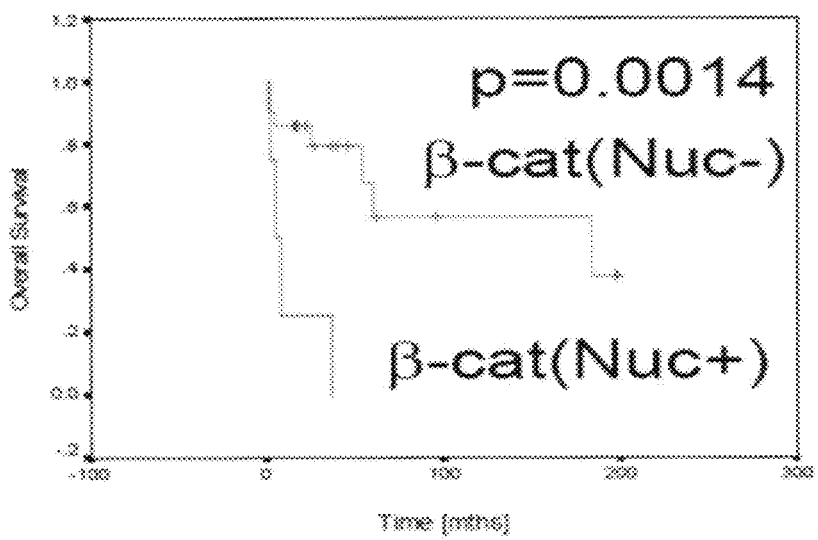

(D)

Median DFS, Ep-ICD-β-cat Nuc+= 5 mths
Median DFS, Ep-ICD-β-cat Nuc- =185 mths

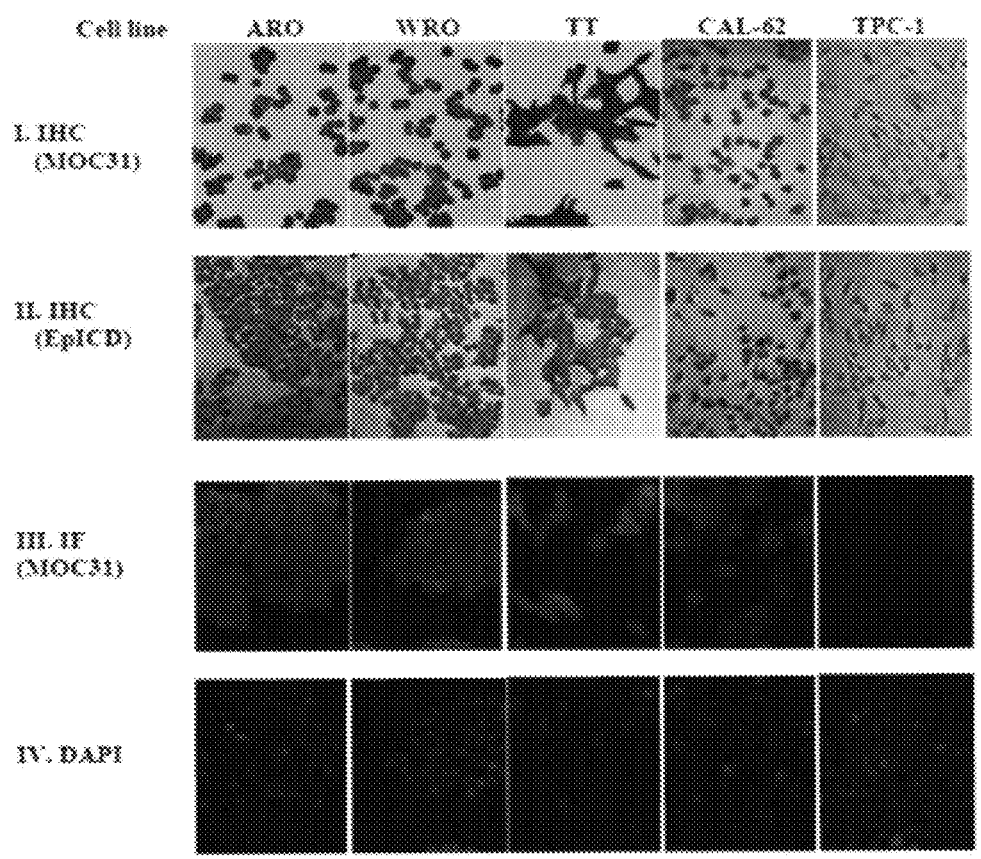

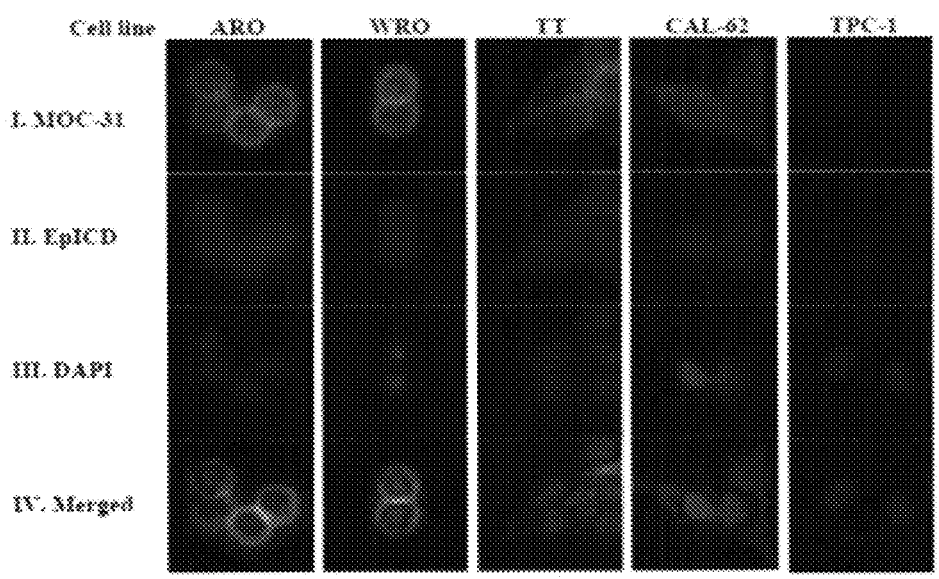

(C)

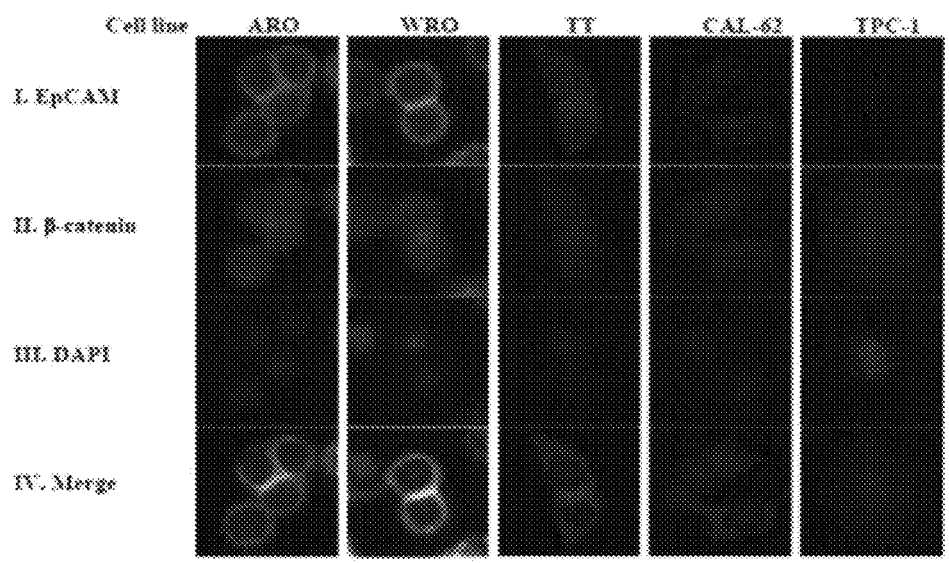

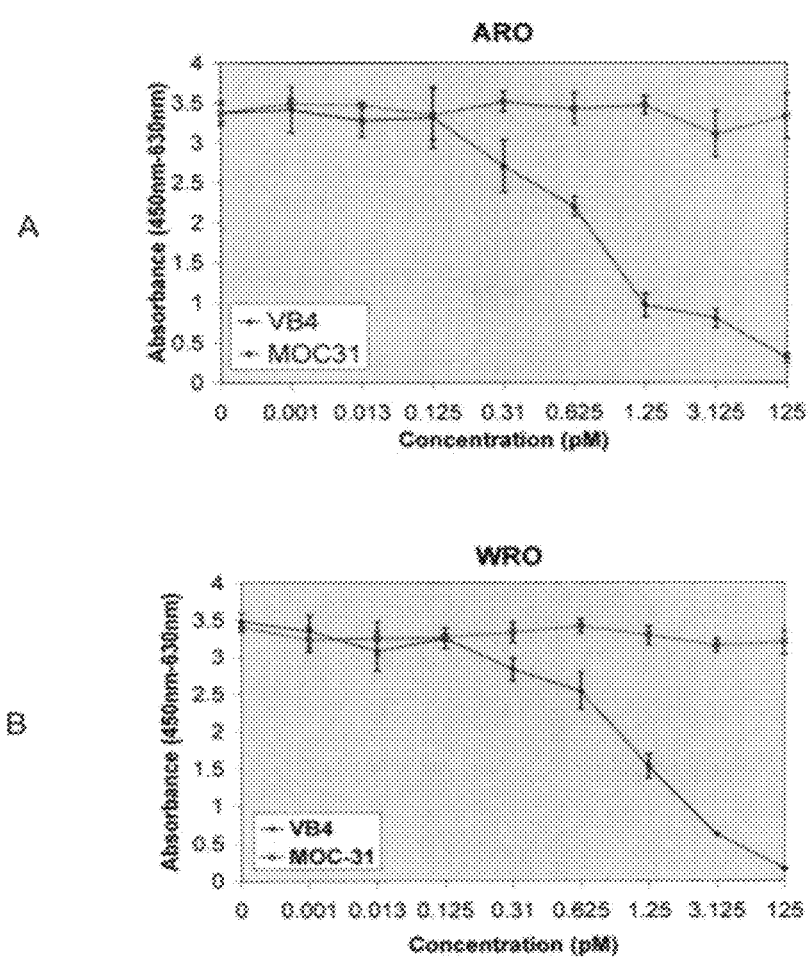

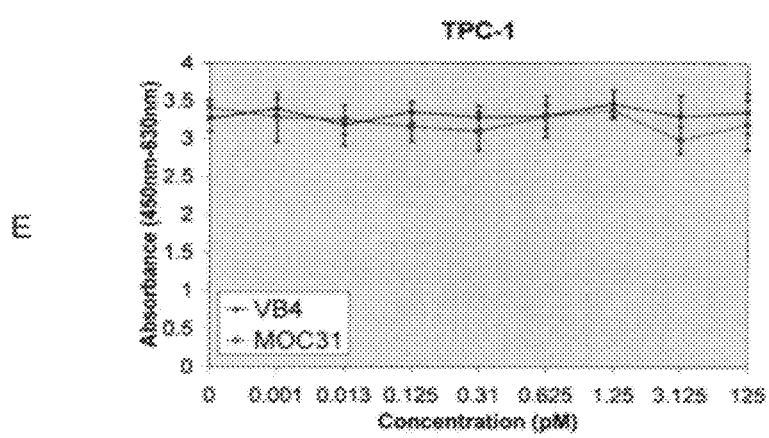

(A)

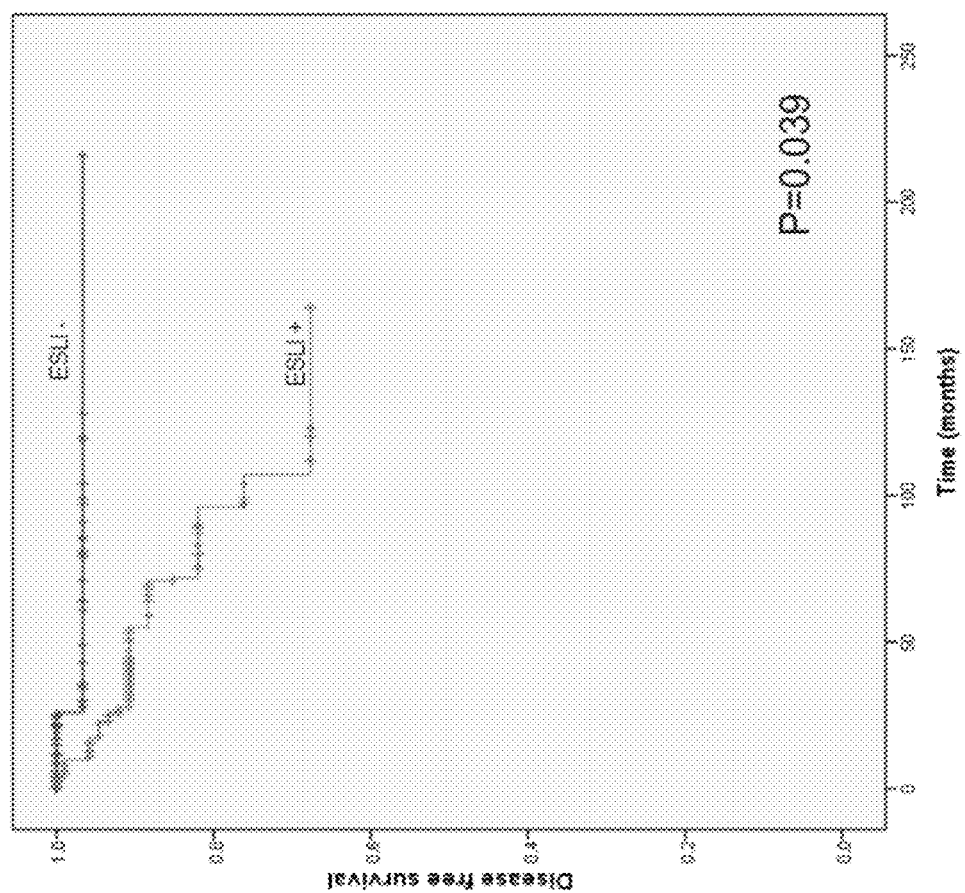

SEQUENCE LISTING

<160> NUMBER OF SEQ ID NOS: 10

<210> SEQ ID NO 1
<211> LENGTH: 314
<212> TYPE: PRT
<213> ORGANISM: Homo sapiens

<400> SEQUENCE: 1

Met Ala Pro Pro Gln Val Leu Ala Phe Gly Leu Leu Ala Ala Ala
1               5                   10                  15

Thr Ala Thr Phe Ala Ala Ala Gln Glu Glu Cys Val Cys Glu Asn Tyr
                20                  25                  30

Lys Leu Ala Val Asn Cys Phe Val Asn Asn Asn Arg Gln Cys Gln Cys
            35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

```
Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
            245                 250                 255

Pro Glu Phe Ser Met Gln Gly Leu Lys Ala Gly Val Ile Ala Val Ile
        260                 265                 270

Val Val Val Val Ile Ala Val Val Ala Gly Ile Val Val Leu Val Ile
        275                 280                 285

Ser Arg Lys Lys Arg Met Ala Lys Tyr Glu Lys Ala Glu Ile Lys Glu
    290                 295                 300

Met Gly Glu Met His Arg Glu Leu Asn Ala
305                 310

<210> SEQ ID NO 2
<211> LENGTH: 1731
<212> TYPE: DNA
<213> ORGANISM: Homo sapiens

<400> SEQUENCE: 2
aactgcagcg ccggggctgg gggaggggag cctactcact ccccccaactc ccgggcggtg    60 actcatcaac gagcaccagc ggccagaggt gagcagtccc gggaaggggc cgagaggcgg   120
ggccgccagg tcgggcaggt gtgcgctccg ccccgccgcg cgcacagagc gctagtcctt   180
cggcgagcga gcaccttcga cgcggtccgg gaccccctc gtcgctgtcc tcccgacgcg    240
gacccgcgtg ccccaggcct cgcgctgccc ggccggctcc tcgtgtccca ctccggcgc    300 acgccctccc gcgagtcccg ggcccctccc gcgcccctct tctcggcgcg cgcgcagcat   360
ggcgcccccg caggtcctcg cgttcgggct tctgcttgcc gcggcgacgg cgacttttgc   420
cgcagctcag gaagaatgtg tctgtgaaaa ctacaagctg gccgtaaact gctttgtgaa   480
taataatcgt caatgccagt gtacttcagt tggtgcacaa atactgtca tttgctcaaa    540 gctggctgcc aaatgtttgg tgatgaaggc agaaatgaat ggctcaaaac ttgggagaag   600
agcaaaacct gaaggggccc tccagaacaa tgatgggctt tatgatcctg actgcgatga   660
gagcgggctc tttaaggcca agcagtgcaa cggcacctcc atgtgctggt gtgtgaacac   720
tgctggggtc agaagaacag acaaggacac tgaaataacc tgctctgagc gagtgagaac   780
ctactggatc atcattgaac taaaacacaa agcaagagaa aaaccttatg atagtaaaag   840
tttgcggact gcacttcaga aggagatcac aacgcgttat caactggatc caaaatttat   900
cacgagtatt ttgtatgaga ataatgttat cactattgat ctggttcaaa attcttctca   960
aaaaactcag aatgatgtgg acatagctga tgtggcttat tattttgaaa agatgttaa   1020 aggtgaatcc ttgtttcatt ctaagaaaat ggacctgaca gtaaatgggg aacaactgga   1080
tctggatcct ggtcaaactt taatttatta tgttgatgaa aaagcacctg aattctcaat   1140
gcagggtcta aaagctggtg ttattgctgt tattgtggtt gtggtgatag cagttgttgc   1200
tggaattgtt gtgctggtta tttccagaaa gaagagaatg gcaaagtatg agaaggctga   1260
gataaaggag atgggtgaga tgcatagggaa actcaatgca taactatata atttgaagat   1320
tatagaagaa gggaaatagc aaatggacac aaattacaaa tgtgtgtgcg tgggacgaag   1380
acatctttga aggtcatgag tttgttagtt aacatcata tatttgtaat agtgaaacct    1440
gtactcaaaa tataagcagc ttgaaactgg ctttaccaat cttgaaattt gaccacaagt   1500
gtcttatata tgcagatcta atgtaaaatc cagaacttgg actccatcgt taaaattatt   1560
```

```
tatgtgtaac attcaaatgt gtgcattaaa tatgcttcca cagtaaaatc tgaaaaactg    1620
atttgtgatt gaaagctgcc tttctattta cttgagtctt gtacatacat actttttat    1680 gagctatgaa ataaaacatt ttaaactgaa tttcttaaaa aaaaaaaaa a              1731

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
ccatgtgctg gtgtgtgaa                                                   19

<210> SEQ ID NO 4
<211> LENGTH: 26
<212> TYPE: DNA
<213> ORGANISM: Artificial Sequence
<220> FEATURE:
<223> OTHER INFORMATION: primer

<400> SEQUENCE: 4
tgtgttttag ttcaatggat gatcca                                           26

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
agccacatcg ctcagacac                                                   19

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
gcccaatacg accaaatcc                                                   19

<210> SEQ ID NO 7
<211> LENGTH: 781
<212> TYPE: PRT
<213> ORGANISM: Homo sapiens

<400> SEQUENCE: 7

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60

Glu Trp Glu Gln Gly Phe Ser Gln Ser Phe Thr Gln Glu Gln Val Ala
65                  70                  75                  80

Asp Ile Asp Gly Gln Tyr Ala Met Thr Arg Ala Gln Arg Val Arg Ala
                85                  90                  95
```

-continued

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
            130                 135                 140

Asp Ala Glu Leu Ala Thr Arg Ala Ile Pro Glu Leu Thr Lys Leu Leu
145                 150                 155                 160

Asn Asp Glu Asp Gln Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
            290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
            370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
            450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

```
Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
        530                 535                 540

Gln Asp Thr Gln Arg Arg Thr Ser Met Gly Gly Thr Gln Gln Phe
545                 550                 555                 560

Val Glu Gly Val Arg Met Glu Ile Val Glu Gly Cys Thr Gly Ala
                565                 570                 575

Leu His Ile Leu Ala Arg Asp Val His Asn Arg Ile Val Ile Arg Gly
        580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
        610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
        690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
770                 775                 780

<210> SEQ ID NO 8
<211> LENGTH: 3720
<212> TYPE: DNA
<213> ORGANISM: Homo sapiens

<400> SEQUENCE: 8
aggatacagc ggcttctgcg cgacttataa gagctccttg tgcggcgcca ttttaagcct      60
ctcggtctgt ggcagcagcg ttggcccggc cccgggagcg gagagcgagg ggaggcggag     120
acggaggaag gtctgaggag cagcttcagt ccccgccgag ccgccaccgc aggtcgagga     180
cggtcggact cccgcggcgg gaggagcctg ttccctgag  ggtatttgaa gtataccata     240
caactgtttt gaaaatccag cgtggacaat ggctactcaa gctgatttga tggagttgga     300
catggccatg gaaccagaca gaaaagcggc tgttagtcac tggcagcaac agtcttacct     360
ggactctgga atccattctg gtgccactac cacagctcct tctctgagtg gtaaaggcaa     420
tcctgaggaa gaggatgtgg atacctccca gtcctgtat  gagtgggaac agggattttc     480
tcagtccttc actcaagaac aagtagctga tattgatgga cagtatgcaa tgactcgagc     540
tcagagggta cgagctgcta tgttccctga gacattagat gagggcatgc agatcccatc     600
```

```
tacacagttt gatgctgctc atcccactaa tgtccagcgt ttggctgaac catcacagat    660
gctgaaacat gcagttgtaa acttgattaa ctatcaagat gatgcagaac ttgccacacg    720
tgcaatccct gaactgacaa aactgctaaa tgacgaggac caggtggtgg ttaataaggc    780
tgcagttatg gtccatcagc tttctaaaaa ggaagcttcc agacacgcta tcatgcgttc    840
tcctcagatg gtgtctgcta ttgtacgtac catgcagaat acaaatgatg tagaaacagc    900
tcgttgtacc gctgggacct tgcataacct ttcccatcat cgtgagggct tactggccat    960
ctttaagtct ggaggcattc ctgccctggt gaaaatgctt ggttcaccag tggattctgt   1020
gttgttttat gccattacaa ctctccacaa cctttttatta catcaagaag gagctaaaat  1080
ggcagtgcgt ttagctggtg ggctgcagaa aatggttgcc ttgctcaaca aaacaaatgt   1140
taaattcttg gctattacga cagactgcct tcaaatttta gcttatggca accaagaaag   1200
caagctcatc atactggcta gtggtggacc ccaagcttta gtaaatataa tgaggaccta   1260
tacttacgaa aaactactgt ggaccacaag cagagtgctg aaggtgctat ctgtctgctc   1320
tagtaataag ccggctattg tagaagctgg tggaatgcaa gctttaggac ttcacctgac   1380
agatccaagt caacgtcttg ttcagaactg tctttggact ctcaggaatc tttcagatgc   1440
tgcaactaaa caggaaggga tggaaggtct ccttgggact cttgttcagc ttctgggttc   1500
agatgatata aatgtggtca cctgtgcagc tggaattctt tctaacctca cttgcaataa   1560
ttataagaac aagatgatgg tctgccaagt gggtggtata gaggctcttg tgcgtactgt   1620
ccttcgggct ggtgacaggg aagacatcac tgagcctgcc atctgtgctc ttcgtcatct   1680
gaccagccga caccaagaag cagagatggc ccagaatgca gttcgccttc actatggact   1740
accagttgtg gttaagctct acacccacc atcccactgg cctctgataa aggctactgt   1800
tggattgatt cgaaatcttg ccctttgtcc cgcaaatcat gcacctttgc gtgagcaggg   1860
tgccattcca cgactagttc agttgcttgt tcgtgcacat caggataccc agcgccgtac   1920
gtccatgggt gggacacagc agcaatttgt ggaggggggtc cgcatggaag aaatagttga   1980
aggttgtacc ggagcccttc acatcctagc tcgggatgtt cacaaccgaa ttgttatcag   2040
aggactaaat accattccat tgtttgtgca gctgctttat tctcccattg aaaacatcca   2100
aagagtagct gcaggggtcc tctgtgaact tgctcaggac aaggaagctg cagaagctat   2160
tgaagctgag ggagccacag ctcctctgac agagttactt cactctagga atgaaggtgt   2220
ggcgacatat gcagctgctg ttttgttccg aatgtctgag acaagccac aagattacaa    2280
gaaacggctt tcagttgagc tgaccagctc tctcttcaga acagagccaa tggcttggaa   2340
tgagactgct gatcttggac ttgatattgg tgcccaggga gaaccccttg gatatcgcca   2400
ggatgatcct agctatcgtt cttttcactc tggtggatat ggccaggatg ccttgggtat   2460
ggaccccatg atggaacatg agatgggtgg ccaccaccct ggtgctgact atccagttga   2520
tgggctgcca gatctggggc atgcccagga cctcatggat gggctgcctc caggtgacag   2580
caatcagctg gcctggtttg atactgacct gtaaatcatc tttaggtaa gaagttttaa    2640
aaagccagtt tgggtaaaat acttttactc tgcctacaga acttcagaaa gacttggttg   2700
gtagggtggg agtggtttag gctatttgta aatctgccac aaaaacaggt atatactttg   2760
aaaggagatg tcttggaaca ttggaatgtt ctcagatttc tggttgttat gtgatcatgt   2820
gtggaagtta ttaacttaa tgttttttgc cacagctttt gcaacttaat actcaaatga    2880
gtaacatttg ctgtttaaa cattaatagc agcctttctc tctttataca gctgtattgt    2940
ctgaacttgc attgtgattg gcctgtagag ttgctgagag ggctcgaggg gtgggctggt   3000
```

| | |
|---|---|
| atctcagaaa gtgcctgaca cactaaccaa gctgagtttc ctatgggaac aattgaagta | 3060 |
| aacttttgt tctggtcctt tttggtcgag gagtaacaat acaaatggat tttgggagtg | 3120 |
| actcaagaag tgaagaatgc acaagaatgg atcacaagat ggaatttatc aaaccctagc | 3180 |
| cttgcttgtt aaatttttt ttttttttt ttaagaatat ctgtaatggt actgactttg | 3240 |
| cttgctttga agtagctctt tttttttttt ttttttttt tttgcagtaa ctgttttta | 3300 |
| agtctctcgt agtgttaagt tatagtgaat actgctacag caatttctaa ttttaagaa | 3360 |
| ttgagtaatg gtgtagaaca ctaattcata atcactctaa ttaattgtaa tctgaataaa | 3420 |
| gtgtaacaat tgtgtagcct ttttgtataa aatagacaaa tagaaaatgg tccaattagt | 3480 |
| ttcctttta atatgcttaa aataagcagg tggatctatt tcatgttttt gatcaaaaac | 3540 |
| tatttgggat atgtatgggt agggtaaatc agtaagaggt gttatttgga accttgtttt | 3600 |
| ggacagttta ccagttgcct tttatcccaa agttgttgta acctgctgtg atacgatgct | 3660 |
| tcaagagaaa atgcggttat aaaaaatggt tcagaattaa acttttaatt cattcgattg | 3720 |

<210> SEQ ID NO 9
<211> LENGTH: 3415
<212> TYPE: DNA
<213> ORGANISM: Homo sapiens

<400> SEQUENCE: 9

| | |
|---|---|
| aggatacagc ggcttctgcg cgacttataa gagctccttg tgcggcgcca tttttaagcct | 60 |
| ctcggtctgt ggcagcagcg ttggcccggc cccgggagcg gagagcgagg ggaggcggag | 120 |
| acggaggaag gtctgaggag cagcttcagt ccccgccgag ccgccaccgc aggtcgagga | 180 |
| cggtcggact cccgcggcgg gaggagcctg ttcccctgag ggtatttgaa gtataccata | 240 |
| caactgtttt gaaaatccag cgtggacaat ggctactcaa gctgatttga tggagttgga | 300 |
| catggccatg gaaccagaca gaaaagcggc tgttagtcac tggcagcaac agtcttacct | 360 |
| ggactctgga atccattctg gtgccactac cacagctcct tctctgagtg gtaaaggcaa | 420 |
| tcctgaggaa gaggatgtgg atacctccca agtcctgtat gagtgggaac agggatttc | 480 |
| tcagtccttc actcaagaac aagtagctga tattgatgga cagtatgcaa tgactcgagc | 540 |
| tcagagggta cgagctgcta tgttccctga gacattagat gagggcatgc agatcccatc | 600 |
| tacacagttt gatgctgctc atcccactaa tgtccagcgt ttggctgaac catcacagat | 660 |
| gctgaaacat gcagttgtaa acttgattaa ctatcaagat gatgcagaac ttgccacacg | 720 |
| tgcaatccct gaactgacaa aactgctaaa tgacgaggac caggtggtgg ttaataaggc | 780 |
| tgcagttatg gtccatcagc tttctaaaaa ggaagcttcc agacacgcta tcatgcgttc | 840 |
| tcctcagatg gtgtctgcta ttgtacgtac catgcagaat acaaatgatg tagaaacagc | 900 |
| tcgttgtacc gctgggacct tgcataacct ttcccatcat cgtgagggct tactggccat | 960 |
| ctttaagtct ggaggcattc ctgccctggt gaaaatgctt ggttcaccag tggattctgt | 1020 |
| gttgttttat gccattacaa ctctccacaa ccttttatta catcaagaag gagctaaaat | 1080 |
| ggcagtgcgt ttagctggtg ggctgcagaa aatggttgcc ttgctcaaca aaacaaatgt | 1140 |
| taaattcttg gctattacga cagactgcct tcaaatttta gcttatggca accaagaaag | 1200 |
| caagctcatc atactggcta gtggtggacc ccaagcttta gtaaatataa tgaggaccta | 1260 |
| tacttacgaa aaactactgt ggaccacaag cagagtgctg aaggtgctat ctgtctgctc | 1320 |
| tagtaataag ccggctattg tagaagctgg tggaatgcaa gctttaggac ttcacctgac | 1380 |

```
agatccaagt caacgtcttg ttcagaactg tctttggact ctcaggaatc tttcagatgc    1440
tgcaactaaa caggaaggga tggaaggtct ccttgggact cttgttcagc ttctgggttc    1500
agatgatata aatgtggtca cctgtgcagc tggaattctt tctaacctca cttgcaataa    1560
ttataagaac aagatgatgg tctgccaagt gggtggtata gaggctcttg tgcgtactgt    1620
ccttcgggct ggtgacaggg aagacatcac tgagcctgcc atctgtgctc ttcgtcatct    1680
gaccagccga caccaagaag cagagatggc ccagaatgca gttcgccttc actatggact    1740
accagttgtg gttaagctct tacacccacc atcccactgg cctctgataa aggctactgt    1800
tggattgatt cgaaatcttg ccctttgtcc cgcaaatcat gcacctttgc gtgagcaggg    1860
tgccattcca cgactagttc agttgcttgt tcgtgcacat caggataccc agcgccgtac    1920
gtccatgggt gggacacagc agcaatttgt ggagggggtc cgcatggaag aaatagttga    1980
aggttgtacc ggagcccttc acatcctagc tcggatgtt cacaaccgaa ttgttatcag     2040
aggactaaat accattccat gtttgtgca gctgctttat tctcccattg aaaacatcca     2100
aagagtagct gcaggggtcc tctgtgaact tgctcaggac aaggaagctg cagaagctat    2160
tgaagctgag ggagccacag ctcctctgac agagttactt cactctagga atgaaggtgt    2220
ggcgacatat gcagctgctg ttttgttccg aatgtctgag acaagccac aagattacaa     2280 gaaacggctt tcagttgagc tgaccagctc tctcttcaga acagagccaa tggcttggaa    2340
tgagactgct gatcttggac ttgatattgg tgcccaggga gaaccccttg gatatcgcca    2400
ggatgatcct agctatcgtt cttttcactc tggtggatat ggccaggatg ccttgggtat    2460
ggaccccatg atggaacatg agatgggtgg ccaccaccct ggtgctgact atccagttga    2520
tgggctgcca gatctggggc atgcccagga cctcatggat gggctgcctc aggtgacag     2580 caatcagctg gcctggtttg atactgacct gtaaatcatc ctttagctgt attgtctgaa    2640
cttgcattgt gattggcctg tagagttgct gagagggctc gaggggtggg ctggtatctc    2700
agaaagtgcc tgacacacta accaagctga gtttcctatg ggaacaattg aagtaaactt    2760
tttgttctgg tccttttttgg tcgaggagta acaatacaaa tggattttgg gagtgactca    2820
agaagtgaag aatgcacaag aatggatcac aagatggaat ttatcaaacc ctagccttgc    2880
ttgttaaatt ttttttttttt ttttttttaag aatatctgta atggtactga cttgcttgc    2940 tttgaagtag ctcttttttt tttttttttt ttttttttgc agtaactgtt ttttaagtct    3000
ctcgtagtgt taagttatag tgaatactgc tacagcaatt tctaattttt aagaattgag    3060
taatggtgta gaacactaat tcataatcac tctaattaat tgtaatctga ataaagtgta    3120
acaattgtgt agccttttg tataaaatag acaaatagaa aatggtccaa ttagtttcct     3180
ttttaatatg cttaaaataa gcaggtggat ctatttcatg ttttttgatca aaaactattt    3240 gggatatgta tgggtagggt aaatcagtaa gaggtgttat ttggaacctt gttttggaca    3300
gtttaccagt tgccttttat cccaaagttg ttgtaacctg ctgtgatacg atgcttcaag    3360
agaaaatgcg gttataaaaa atggttcaga attaaacttt taattcattc gattg          3415
```

<210> SEQ ID NO 10
<211> LENGTH: 3256
<212> TYPE: DNA
<213> ORGANISM: Homo sapiens

<400> SEQUENCE: 10

```
aggatacagc ggcttctgcg cgacttataa gagctccttg tgcggcgcca ttttaagcct      60
ctcggtctgt ggcagcagcg ttggcccggc cccgggagcg gagagcgagg ggaggcggag     120
```

-continued

```
acggaggaag gtctgaggag cagcttcagt ccccgccgag ccgccaccgc aggtcgagga      180
cggtcggact cccgcggcgg gaggagcctg ttcccctgag ggtatttgaa gtataccata      240
caactgtttt gaaaatccag cgtggacaat ggctactcaa gctgatttga tggagttgga      300
catggccatg gaaccagaca gaaaagcggc tgttagtcac tggcagcaac agtcttacct      360
ggactctgga atccattctg gtgccactac cacagctcct tctctgagtg gtaaaggcaa      420
tcctgaggaa gaggatgtgg atacctccca agtcctgtat gagtgggaac agggattttc      480
tcagtccttc actcaagaac aagtagctga tattgatgga cagtatgcaa tgactcgagc      540
tcagagggta cgagctgcta tgttccctga gacattagat gagggcatgc agatcccatc      600
tacacagttt gatgctgctc atcccactaa tgtccagcgt ttggctgaac catcacagat      660
gctgaaacat gcagttgtaa acttgattaa ctatcaagat gatgcagaac ttgccacacg      720
tgcaatccct gaactgacaa aactgctaaa tgacgaggac caggtggtgg ttaataaggc      780
tgcagttatg gtccatcagc tttctaaaaa ggaagcttcc agacacgcta tcatgcgttc      840
tcctcagatg gtgtctgcta ttgtacgtac catgcagaat acaaatgatg tagaaacagc      900
tcgttgtacc gctgggacct tgcataacct ttcccatcat cgtgagggct tactggccat      960 cttaagtct ggaggcattc ctgccctggt gaaaatgctt ggttcaccag tggattctgt      1020
gttgttttat gccattacaa ctctccacaa cctttattta catcaagaag gagctaaaat      1080
ggcagtgcgt ttagctggtg ggctgcagaa aatggttgcc ttgctcaaca aaacaaatgt      1140
taaattcttg gctattacga cagactgcct tcaaatttta gcttatggca accaagaaag      1200
caagctcatc atactggcta gtggtggacc ccaagcttta gtaaatataa tgaggaccta      1260
tacttacgaa aaactactgt ggaccacaag cagagtgctg aaggtgctat ctgtctgctc      1320
tagtaataag ccggctattg tagaagctgg tggaatgcaa gctttaggac ttcacctgac      1380
agatccaagt caacgtcttg ttcagaactg tctttggact ctcaggaatc tttcagatgc      1440
tgcaactaaa caggaaggga tggaaggtct ccttgggact cttgttcagc ttctgggttc      1500
agatgatata aatgtggtca cctgtgcagc tggaattctt tctaacctca cttgcaataa      1560
ttataagaac aagatgatgg tctgccaagt gggtggtata gaggctcttg tgcgtactgt      1620
ccttcgggct ggtgacaggg aagacatcac tgagcctgcc atctgtgctc ttcgtcatct      1680
gaccagccga caccaagaag cagagatggc ccagaatgca gttcgccttc actatggact      1740
accagttgtg gttaagctct tacacccacc atcccactgg cctctgataa aggctactgt      1800
tggattgatt cgaaatcttg ccctttgtcc cgcaaatcat gcacctttgc gtgagcaggg      1860
tgccattcca cgactagttc agttgcttgt tcgtgcacat caggataccc agcgccgtac      1920
gtccatgggt gggacacagc agcaatttgt ggaggggtc cgcatggaag aaatagttga      1980
aggttgtacc ggagcccttc acatcctagc tcgggatgtt cacaaccgaa ttgttatcag      2040
aggactaaat accattccat gtttgtgca gctgctttat tctcccattg aaaacatcca      2100
aagagtagct gcaggggtcc tctgtgaact tgctcaggac aaggaagctg cagaagctat      2160
tgaagctgag ggagccacag ctcctctgac agagttactt cactctagga atgaaggtgt      2220
ggcgacatat gcagctgctg tttttgttccg aatgtctgag acaagccac aagattacaa      2280 gaaacggctt tcagttgagc tgaccagctc tctcttcaga acagagccaa tggcttggaa      2340
tgagactgct gatcttggac ttgatattgg tgcccaggga gaaccccttg gatatcgcca      2400
ggatgatcct agctatcgtt cttttcactc tggtggatat ggccaggatg ccttgggtat      2460
```

-continued

```
ggacccmatg atggaacatg agatgggtgg ccaccaccct ggtgctgact atccagttga    2520
tgggctgcca gatctggggc atgcccagga cctcatggat gggctgcctc caggtgacag    2580
caatcagctg gcctggtttg atactgacct gtaaatcatc ctttaggagt aacaatacaa    2640
atggattttg ggagtgactc aagaagtgaa gaatgcacaa gaatggatca caagatggaa    2700
tttatcaaac cctagccttg cttgttaaat tttttttttt ttttttttaa gaatatctgt    2760
aatggtactg actttgcttg ctttgaagta gctctttttt tttttttttt tttttttttg    2820
cagtaactgt tttttaagtc tctcgtagtg ttaagttata gtgaatactg ctacagcaat    2880
ttctaatttt taagaattga gtaatggtgt agaacactaa ttcataatca ctctaattaa    2940
ttgtaatctg aataaagtgt aacaattgtg tagcctttt gtataaaata gacaaataga    3000
aaatggtcca attagtttcc tttttaatat gcttaaaata agcaggtgga tctatttcat    3060 gttttgatc aaaaactatt tgggatatgt atgggtaggg taaatcagta agaggtgtta    3120
tttggaacct tgttttggac agtttaccag ttgccttta tcccaaagtt gttgtaacct    3180
gctgtgatac gatgcttcaa gagaaaatgc ggttataaaa aatggttcag aattaaactt    3240
ttaattcatt cgattg                                                   3256
```

METHODS AND COMPOSITIONS FOR THE DIAGNOSIS AND TREATMENT OF THYROID CANCER

CROSS-REFERENCE TO RELATED APPLICATIONS

This application is a continuation-in-part of U.S. patent application Ser. No. 13/497,441, filed Mar. 21, 2012, which is a US national stage of International Patent Application No. PCT/CA2010/001503, filed Sep. 21, 2010, which claims the benefit of the priority of U.S. Provisional Patent Application No. 61/244,173, filed on Sep. 21, 2009, all of which are hereby incorporated herein by reference.

FIELD OF THE INVENTION

The invention relates to markers associated with thyroid cancer, in particular aggressive thyroid cancer, compositions, kits, and methods for detecting, diagnosing, predicting, monitoring, and characterizing thyroid cancer, and treatment of thyroid cancer.

BACKGROUND OF THE INVENTION

Epithelial cell adhesion molecule (EpCAM) is a 40 kDa transmembrane glycoprotein showing frequent overexpression in several human malignancies [Spizzo et al., 2004; Went P et al., 2006; Wenqi D et al, 2009]. EpCAM was originally identified as a cancer marker, attributable to its high expression on rapidly proliferating epithelial tumors [reviewed in Trzpis M et al., 2007]. The normal epithelia express EpCAM at a variable though generally lower level than cancer cells. It is also overexpressed in normal stem and progenitor cells [Stingl J et al., 2001; Schmelzer E et al., 2007; Trzpis M et al., 2008] and in cancer-initiating cells in breast, colon, pancreas and prostate carcinomas [Al-Hajj M et al., 2003; O'Brien C A et al., 2007; Ricci-Vitiani L et al., 2007]. Recently, EpCAM has been detected in circulating tumor cells expressing E6/E7-HPV oncogenes in peripheral blood in cervical cancer patients after radical hysterectomy [Weismann P et al., 2009]. There is a large database on EpCAM staining for many cancers and normal tissues. However, all these studies used antibodies directed against the extracellular domain of EpCAM that may detect the EpCAM precursor or cell-bound EpEx (the "extracellular domain"), or both [Wenqi D et al., 2009].

EpCAM is a pleiotropic molecule that serves important roles in cell adhesion, cell proliferation, differentiation, migration, cell cycle regulation and is implicated in cancer and stem cell signaling [Munz et al., 2009]. The molecular mechanisms that regulate EpCAM expression are not well understood. Recently, regulated intramembrane proteolysis (RIP) has been shown to act as its mitogenic signal transducer in vitro and in vivo [Maetzel et al., 2009]. The cleavage and shedding of EpCAM ectodomain, EpEx, by proteases-TACE and Presenilin-2, releases its intracellular domain (Ep-ICD) that translocates to the nucleus. The association of Ep-ICD with FHL2 and Wnt pathway components—β-catenin and Lef-1 forms a nuclear complex that binds DNA at Lef-1 consensus sites and induces gene transcription, leading to increased cell proliferation and has been shown to be oncogenic in immunodeficient mice [Maetzel, 2009]. In view of the multiple roles of EpCAM as an oncogenic signal transducer, cell adhesion molecule and cancer stem cell marker [Litvinov S V et al., 1997; Munz et al., 2009], it is important to establish the clinical significance of nuclear Ep-ICD in human cancers.

Nuclear Ep-ICD was recently reported in a preliminary study in human colon cancer, but not in the normal colonic epithelium [Maetzel, 2009]. In view of the tremendous heterogeneity in solid tumors, the clinical significance of nuclear Ep-ICD in other human cancers remains to be established. Further, EpCAM has been shown to increase cell proliferation by upregulation of c-myc, cyclins A and E [Munz et al., 2004].

Thyroid cancer (TC) represents 90% of all endocrine malignancies with an estimated annual incidence of 122,800 cases worldwide and approximately 33,000 newly diagnosed cases in the USA [Reis et al., 2005; Jemal et al., 2008]. Anaplastic thyroid cancer (ATC) is a rare but very aggressive form of this malignancy, accounting for less than 2% of all thyroid cancers. ATC commonly presents as a rapidly increasing neck mass that spreads locally, compresses the adjacent structures, with a tendency to disseminate to regional lymph nodes and distant sites [Pasieka J L et al., 2003; Are C & Shaha 2006]. Most well differentiated thyroid cancers have an excellent prognosis, with relative 5-year survival rates above 95%, despite their tendency for early metastasis. However, the less-differentiated thyroid tumors—anaplastic and other aggressive metastatic thyroid cancers can be fatal with median survival time ranging from 4 months to 5 years [Are C & Shaha, 2006]. This variation in clinical outcomes may be attributed to the differences in genetic damage acquired by the aggressive and non-aggressive thyroid tumors during their malignant evolution.

The pathogenesis of ATC is linked to mutations in BRAF, RAS, β-Catenin, PIK3CA, TP53, AXIN1, PTEN and APC genes [reviewed in Smallridge R C et al., 2009]. The gene expression signatures in ATC have been identified showing the upregulation of the serine/threonine kinase Polo-like kinase 1 (PLK1) and its potential as a therapeutic target in ATC has been investigated [Salvatore G et al., 2007 CR; Nappi T C et al., 2009]. However, there are no proven predictive molecular markers to identify aggressive TCs.

Further, well-differentiated papillary thyroid carcinoma ("PTC") generally has a good prognosis and can be effectively managed through a combination of surgery and radioactive iodine treatment. Yet, a subset of PTC show poor prognosis and tumor recurrence may lead to increased mortality [Lin J D et. al., 2009]. The lack of universally accepted biomarkers to define aggressive PTC further confounds the difficulty in determining which PTC patients have a poor prognosis and those who do not. According to American Thyroid Association (ATA) guidelines, there are conflicting data outlining the patients to whom radioiodine remnant ablation should be given. This discrepancy might be caused by the limitation faced by the current system in differentiating between aggressive and non-aggressive PTC. A variety of factors have been studied and found to affect the prognosis for PTC patients including age, gender, tumor histology, extracapsular extension, tumor size and positive lymph nodes or distant metastases [Sipos J A et al., 2010]. Despite the plethora of criteria to differentiate aggressive PTCs from non-aggressive cases, lack of universal consensus and controversy generating ongoing debates resulted in only a select few being considered in the currently recommended TNM staging system [Sipos J A et al., 2010].

There is an urgent need to find reliable biomarker(s) that can aid in the identification of patients with aggressive PTC. The early stratification of patients with a poorer prognosis would enable oncologists to choose the treatment strategy that matches more closely to the patient's cancer biology, thereby avoiding over-treatment, improving survival and quality of life for benefiting patients, particularly in a population that has demonstrated an enhanced risk for aggressive tumors. Biomarker(s) that serve as a tool for timely intervention and detection could direct effective adjuvant treatment to those patients who require it and save patients with non-aggressive PTCs from unnecessary additional surgery and radiation. Subsequently, these novel marker(s) would possess the ability to pave the way for a revised, comprehensive, universally accepted management plan for PTC.

SUMMARY OF THE INVENTION

The present invention relates to markers of thyroid cancer. In particular, EpCAM polypeptides and domains thereof (in particular, the ectodomain EpEx and the intracellular domain EP-ICD) and β-catenin (collectively referred to herein as "Polypeptide Thyroid Cancer Markers"), and polynucleotides encoding such polypeptides and domains thereof (collectively referred to herein as "Polynucleotide Thyroid Cancer Markers") constitute biomarkers for thyroid cancer, in particular aggressive thyroid cancer, more particularly anaplastic thyroid cancer (ATC). Polypeptide Thyroid Cancer Markers and Polynucleotide Thyroid Cancer Markers, and portions or fragments thereof, are sometimes collectively referred to herein as "Thyroid Cancer Markers".

The term "Thyroid Cancer Markers" in some aspects of the invention may include Wnt Proteins and polynucleotides encoding Wnt Proteins; and thus "Polypeptide Thyroid Cancer Markers" in some aspects includes Wnt Proteins, and "Polynucleotide Thyroid Cancer Markers" in some aspects includes polynucleotides encoding Wnt Proteins.

Thus, Thyroid Cancer Markers and agents that interact with the Thyroid Cancer Markers, may be used in detecting, diagnosing, characterizing, classifying, and monitoring thyroid cancer (i.e., monitoring progression of the cancer or the effectiveness of a therapeutic treatment), in the identification of subjects with a predisposition to thyroid cancer, and in determining prognosis or patient survival. In aspects of the invention, the Thyroid Cancer Markers, in particular Ep-ICD, EpEx and optionally β-catenin, are used in characterizing the aggressiveness of a thyroid cancer. In some aspects of the invention, the Thyroid Cancer Markers are used to determine metastatic potential or patient survival. The invention also contemplates methods for assessing the status of a thyroid tissue, and methods for the diagnosis and therapy of thyroid cancer.

A method of the invention wherein Thyroid Cancer Marker(s) are assayed can have enhanced sensitivity and/or specificity relative to a method assaying other markers. The enhanced clinical sensitivity may be about a 5-10% increase, in particular 6-9% increase, more particularly 8% increase in sensitivity. In an embodiment of a method of the invention, Thyroid Cancer Marker(s) detected in tumor samples provide a thyroid cancer clinical sensitivity of at least about 80 to 99%, in particular 90 to 95%, more particularly 91%, 92%, 93%, 94%, 95% or 98% thyroid cancer clinical sensitivity. In embodiments of the invention where one or more of nuclear Ep-ICD, cytoplasmic Ep-ICD, nuclear β-catenin and cytoplasmic β-catenin are detected in a tumor sample the clinical sensitivity can be greater than about 80 to 90%, more particularly greater than about 80 to 85%, most particularly greater than about 83%, 84%, 85%, 90%, 95% or 98%. Clinical sensitivity and specificity may be determined using methods known to persons skilled in the art.

In accordance with methods of the invention, a Thyroid Cancer Marker in a sample can be assessed by detecting the presence in the sample of (a) a polypeptide or polypeptide fragment corresponding to the marker; (b) a transcribed nucleic acid or fragment thereof having at least a portion with which the marker is substantially identical; and/or (c) a transcribed nucleic acid or fragment thereof, wherein the nucleic acid hybridizes with the marker.

In an aspect of the invention, a method is provided for detecting Thyroid Cancer Markers associated with thyroid cancer, in particular aggressive thyroid cancer, more particularly anaplastic thyroid carcinoma, in a patient comprising or consisting essentially of:
(a) obtaining a sample from a patient;
(b) detecting or identifying in the sample one or more Thyroid Cancer Markers and
(c) comparing the detected amount with an amount detected for a standard.

In accordance with methods of the invention, a thyroid tissue can be assessed or characterized, for example, by detecting the presence in the sample of (a) a Thyroid Cancer Marker; (b) a transcribed nucleic acid or fragment thereof having at least a portion with which a Polynucleotide Thyroid Cancer Marker is substantially identical; and/or (c) a transcribed nucleic acid or fragment thereof, wherein the nucleic acid hybridizes with a Polynucleotide Thyroid Cancer Marker. Thyroid Cancer Markers in a sample may be determined by methods as described herein and generally known in the art.

In an aspect, the invention provides a method for characterizing or classifying a thyroid sample comprising detecting a difference in the expression of a first plurality of Thyroid Cancer Marker relative to a control, the first plurality of markers consisting of Ep-ICD, β-catenin, and optionally EpEx, or in another embodiment, Ep-ICD and EpEx, wherein in one embodiment Ep-ICD is nuclear and/or cytoplasmic Ep-ICD.

One aspect of the invention provides a method for detecting thyroid cancer in a patient comprising determining the status of Thyroid Cancer Markers in a sample obtained from the patient, wherein an abnormal status in the sample indicates the presence of thyroid cancer. Thyroid Cancer Markers may be correlated with specific disease stages. Thus, another aspect of the invention provides a method of diagnosing a specific disease stage of thyroid cancer in a patient comprising determining the status of a Thyroid Cancer Marker in a sample obtained from the patient, wherein an abnormal status of the marker indicates the presence of a specific disease stage.

Another aspect of the invention provides a method of screening for thyroid cancer in a patient comprising identifying a patient at risk of having thyroid cancer or in need of screening and determining the status of Thyroid Cancer Markers in a sample obtained from the patient, wherein an abnormal status of the markers indicates the presence of thyroid cancer or a particular stage thereof.

Another aspect provides a diagnostic method comprising identifying a patient who is a candidate for treatment for thyroid cancer and determining the status of Thyroid Cancer Markers in a sample obtained from the patient, wherein an abnormal status of the Thyroid Cancer Markers in the sample indicates that treatment is desirable or necessary.

In aspects of the invention, the abnormal status can be an elevated status, low status or negative status. In an embodiment of the invention for detecting or diagnosing thyroid cancer the abnormal status is an elevated status.

In an aspect, the invention provides a method for diagnosing ATC in a subject, the method comprising:
(a) contacting a sample from a subject with a reagent capable of measuring a level of a target Thyroid Cancer Marker, in particular at least one Thyroid Cancer Marker selected from Ep-ICD, β-catenin, and optionally EpEx and c-myc or in another embodiment Ep-ICD and optionally EpEx; and (b) providing a diagnosis of ATC in said subject based on an increase in the level of at least one of Ep-ICD and β-catenin and optionally c-myc, and optionally a decrease in EpEx, in the sample from the subject over a control level obtained from similar samples taken from subjects who do not have ATC or from the subject at a different time.

In embodiments of this aspect of the invention, the Thyroid Cancer Markers measured are nuclear Ep-ICD, cytoplasmic Ep-ICD, nuclear β-catenin, cytoplasmic β-catenin, and optionally EpEx.

In an embodiment of the invention, a method is provided for detecting one or more of Ep-ICD, β-catenin, EpEx, and EpCAM, associated with thyroid cancer, in particular aggressive thyroid cancer, more particularly anaplastic thyroid cancer, in a patient comprising or consisting essentially of:

(a) obtaining a sample from a patient;

(b) detecting or identifying in the sample one or more of Ep-ICD, β-catenin, EpEx, and EpCAM, in one embodiment Ep-ICD and optionally EpEx or in another embodiment Ep-ICD and EpEx; and (c) comparing the detected amounts with amounts detected for a standard.

In a particular embodiment of the invention, a method is provided for diagnosing ATC in a patient comprising or consisting essentially of:

(a) detecting or identifying in the sample one or more of nuclear Ep-ICD and optionally cytoplasmic Ep-ICD and optionally nuclear β-catenin and cytoplasmic β-catenin; and (b) comparing the detected amount with an amount detected for a standard, wherein an increase in one or more of nuclear Ep-ICD, cytoplasmic Ep-ICD, nuclear β-catenin and cytoplasmic β-catenin is indicative of ATC.

In a particular embodiment of the invention, a method is provided for diagnosing ATC in a patient comprising or consisting essentially of:

(a) detecting or identifying in the sample one or more of nuclear Ep-ICD, cytoplasmic Ep-ICD and EpEx (e.g. membranous EpEx) and optionally nuclear β-catenin, cytoplasmic β-catenin; and (b) comparing the detected amount with an amount detected for a standard, wherein an increase in one or more of nuclear Ep-ICD, cytoplasmic Ep-ICD and optionally nuclear β-catenin and cytoplasmic β-catenin and a decrease or absence of EpEx is indicative of ATC.

In a particular aspect of the invention, a method is provided for detecting Thyroid Cancer Markers, preferably Ep-ICD and/or β-catenin, associated with aggressive or metastatic thyroid cancer, in a patient comprising or consisting essentially of:

(a) obtaining a sample (e.g. tumor sample) from a patient;

(b) detecting in the sample Thyroid Cancer Markers, preferably Ep-ICD and/or β-catenin; and (c) comparing the detected amount with an amount detected for a standard or cut-off value.

The term "detect" or "detecting" includes assaying, or otherwise establishing the presence or absence of the target marker(s), subunits, or combinations of reagent bound targets, and the like, or assaying for ascertaining, establishing, or otherwise determining one or more factual characteristics of a thyroid cancer such as aggressiveness, metastatic potential or patient survival. A standard may correspond to levels quantitated for samples from control subjects with no disease or early stage disease (e.g., low grade thyroid cancer such as papillary thyroid cancer) or from other samples of the subject.

The invention provides a method of assessing whether a patient is afflicted with or has a pre-disposition for thyroid cancer, in particular aggressive or metastatic thyroid cancer, more particularly ATC, the method comprising comparing:

(a) levels of Thyroid Cancer Markers from the patient; and (b) standard levels of Thyroid Cancer Markers in samples of the same type obtained from control patients not afflicted with thyroid cancer or with a lower grade of thyroid cancer, wherein altered levels of Thyroid Cancer Markers relative to the corresponding standard levels of Thyroid Cancer Markers is an indication that the patient is afflicted with thyroid cancer, in particular aggressive or metastatic thyroid cancer, more particularly ATC.

In an aspect of a method of the invention for assessing whether a patient is afflicted with aggressive or metastatic thyroid cancer, in particular ATC, higher levels of nuclear Ep-ICD, cytoplasmic Ep-ICD, nuclear β-catenin, or cytoplasmic β-catenin, and lower levels or the absence of EpEx (e.g., membranous EpEx), in a sample relative to corresponding normal levels or levels from a patient with a lower grade of thyroid cancer, is an indication that the patient is afflicted with aggressive or metastatic thyroid cancer, in particular ATC.

In an embodiment of a method of the invention for assessing whether a patient is afflicted with anaplastic thyroid cancer, levels of nuclear and/or cytoplasmic Ep-ICD in a sample from the patient are compared to a standard, and higher levels of nuclear and/or cytoplasmic Ep-ICD compared to a standard are indicative of aggressive or metastatic thyroid cancer or anaplastic thyroid cancer.

In an embodiment of a method of the invention for assessing whether a patient is afflicted with anaplastic thyroid cancer, levels of nuclear β-catenin in a sample from the patient are compared to a standard, and higher levels of nuclear β-catenin compared to a standard are indicative of anaplastic thyroid cancer.

In an embodiment of a method of the invention for assessing whether a patient is afflicted with aggressive or metastatic thyroid cancer or anaplastic thyroid cancer, levels of cytoplasmic β-catenin in a sample from the patient are compared to a standard, and higher levels of cytoplasmic β-catenin compared to a standard are indicative of anaplastic thyroid cancer.

In an embodiment of a method of the invention for assessing whether a patient is afflicted with aggressive or metastatic thyroid cancer or anaplastic thyroid cancer, levels of membranous EpEx in a sample from the patient are compared to a standard, and lower levels or absence of membranous EpEx compared to a standard are indicative of anaplastic thyroid cancer.

In an embodiment of a method of the invention for assessing whether a patient is afflicted with follicular thyroid cancer (FTC), levels of membranous EpEx, nuclear Ep-ICD, cytoplasmic Ep-ICD and optionally β-catenin in a sample from the patient are compared to a standard.

In an embodiment of a method of the invention for assessing whether a patient is afflicted with follicular thyroid cancers (FTC), levels of membranous EpEx, nuclear Ep-ICD, and cytoplasmic Ep-ICD in a sample from the patient are compared to a standard. In an embodiment, there is an absence or low levels of nuclear Ep-ICD and optionally higher levels of cytoplasmic β-catenin.

In an embodiment of a method of the invention for assessing whether a patient is afflicted with papillary thyroid cancers (PTC), levels of membranous EpEx, nuclear Ep-ICD, cytoplasmic Ep-ICD and optionally β-catenin in a sample from the patient are compared to a standard. In an embodiment, there is an absence or low levels of nuclear Ep-ICD and optionally β-catenin.

In an embodiment of a method of the invention for assessing whether a patient is afflicted with squamous cell carcinoma of the thyroid, levels of membranous EpEx, nuclear Ep-ICD, cytoplasmic Ep-ICD and optionally β-catenin in a sample from the patient are compared to a standard.

In particular aspects, methods of the invention are used to diagnose the stage of thyroid cancer in a subject or characterizing thyroid cancer in a subject. In an embodiment, the method comprises comparing
 (a) levels of Thyroid Cancer Markers (e.g. biopsy sample) from a sample from the patient; and
 (b) levels of Thyroid Cancer Markers in control samples of the same type obtained from patients without thyroid cancer or control patients with a different stage of thyroid cancer (e.g., low grade thyroid cancer) or from a sample from the patient taken at a different time, wherein altered levels of Thyroid Cancer Markers, relative to the corresponding levels in the control samples is an indication that the patient is afflicted with a more aggressive or metastatic thyroid cancer.

In embodiments, the aggressive thyroid cancer is ATC and the Thyroid Cancer Markers are one or more of nuclear Ep-ICD, nuclear β-catenin, and cytoplasmic β-catenin. In particular embodiments, the Thyroid Cancer Marker is nuclear Ep-ICD.

The invention further provides a non-invasive non-surgical method for detection or diagnosis of thyroid cancer, in particular aggressive or metastatic thyroid cancer, more particularly ATC, in a subject comprising: obtaining a sample (e.g., biopsy sample) from the subject; subjecting the sample to a procedure to detect Thyroid Cancer Marker(s); detecting or diagnosing thyroid cancer by comparing the levels of Thyroid Cancer Marker(s) to the levels of Thyroid Cancer Marker(s) obtained from a control subject with no thyroid cancer or a lower grade of thyroid cancer or from a sample from the patient taken at a different time. In embodiments of this method of the invention, the Thyroid Cancer Marker(s) are one or more of nuclear Ep-ICD, nuclear β-catenin, cytoplasmic β-catenin. In particular embodiments, the Thyroid Cancer Marker is nuclear Ep-ICD. In another embodiment the Thyroid Cancer Marker is cytoplasmic Ep-ICD. In yet another embodiment the Thyroid Cancer Marker is EpEx.

In aspects of the invention, aggressive thyroid cancer, in particular ATC, is detected, diagnosed or characterized by determination of increased levels of one or more of nuclear Ep-ICD, and nuclear β-catenin, cytoplasmic β-catenin, or in another embodiment nuclear and cytoplasmic Ep-ICD when compared to such levels obtained from a control or from a sample from the patient taken at a different time.

In a particular embodiment the invention provides a method for diagnosing the aggressiveness of thyroid cancer in a subject comprising:
 (a) determining the amount of nuclear Ep-ICD and optionally cytoplasmic Ep-ICD, or both nuclear and cytoplasmic Ep-ICD in a sample (e.g., tumor sample) from the subject;
 (b) optionally, determining the amount of one or both of nuclear β-catenin and β-catenin in the sample;
 (c) determining the amount of EpEx in the sample;
 (d) mathematically combining the results of step (a) and optionally step (b), and optionally step (c) to provide a mathematical combination, or in one embodiment mathematically combining the results of step (a) and (c); and
 (e) comparing or correlating the mathematical combination to the aggressiveness of the thyroid cancer.
  The combination is preferably compared to a mathematical combination for a predetermined standard.

In one embodiment the mathematical combination is a Ep-ICD Subcellar Localization Index (ESLI) defined as the sum of the immunohistochemcial (IHC) scores for loss of membranous EpEx, nuclear and cytoplasmic Ep-ICD.

In an aspect, the invention provides a method for monitoring the progression of thyroid cancer in a patient the method comprising:
 (a) detecting Thyroid Cancer Marker(s) in a patient sample (e.g. biopsy sample) at a first time point;
 (b) repeating step (a) at a subsequent point in time; and
 (c) comparing the levels detected in (a) and (b), and thereby monitoring the progression of thyroid cancer in the patient.

The invention provides a method for classifying a patient having thyroid cancer, the method comprising measuring Thyroid Cancer Marker(s) in a sample (e.g. tumor sample) from the patient and correlating the values measured to values measured for the Thyroid Cancer Markers from thyroid cancer patients stratified in classification groups. The method can be used to predict patient survival, wherein the Thyroid Cancer Marker(s) are predictive of survival and wherein the classification groups comprise groups of known overall survival. In aspects of this method of the invention, the Thyroid Cancer Marker(s) are selected from Ep-ICD and optionally β-catenin (e.g., nuclear and cytoplasmic), in particular nuclear Ep-ICD, cytoplasmic Ep-ICD. In various embodiments the values measured can be normalized to provide more accurate quantification and to correct for experimental variations.

In particularly useful aspects of the invention, Polynucleotide Thyroid Cancer Markers, preferably polynucleotides encoding Ep-ICD and optionally B-catenin are detected and levels of Polynucleotide Thyroid Cancer Markers in a sample (e.g., biopsy sample) from a patient are compared with Polynucleotide Thyroid Cancer Marker levels from samples of patients without thyroid cancer, with a lower grade of thyroid cancer, or from levels from samples of the same patient. A method of the invention may employ one or more polynucleotides, oligonucleotides, or nucleic acids capable of hybridizing to Polynucleotide Thyroid Cancer Markers and preferably polynucleotides encoding Ep-ICD. In an aspect of the invention, Ep-ICD mRNA is detected.

The present invention relates to a method for diagnosing and characterizing thyroid cancer, more particularly the stage of thyroid cancer, in a sample from a subject comprising isolating nucleic acids, preferably mRNA, from the sample, and detecting Polynucleotide Thyroid Cancer Markers in the sample. In an embodiment, the presence of increased levels of polynucleotides encoding Ep-ICD and optionally β-catenin, in the sample compared to a standard or control is indicative of the aggressiveness or metastatic potential of a thyroid cancer, in particular is indicative of ATC.

The invention also provides methods for determining the presence or absence of thyroid cancer or the aggressiveness or metastatic potential of a thyroid cancer in a subject, in particular determining ATC, in the subject comprising detecting in the sample a level of nucleic acids that hybridize to a Polynucleotide Thyroid Cancer Marker(s), and comparing the level(s) with a predetermined standard or cut-off value, and therefrom determining the presence or absence of thyroid cancer or the aggressiveness or metastatic potential of a thyroid cancer in the subject, in particular determining ATC in the subject. In an embodiment a method is provided for determining the aggressiveness or metastatic potential of thyroid cancer in a subject comprising (a) contacting a sample taken from the subject with oligonucleotides that hybridize to polynucleotides encoding Ep-ICD and optionally β-catenin; and (b) detecting in the sample a level of nucleic acids that hybridize to the oligonucleotides relative to a predetermined standard or cut-off value, and therefrom determining the aggressiveness or metastatic potential of the cancer in the subject.

In an aspect, the invention provides a method of assessing the aggressiveness or metastatic potential of a thyroid cancer in a patient, the method comprising comparing:
   (a) levels of Polynucleotide Thyroid Cancer Marker(s) in a sample from the patient; and
   (b) control levels of Polynucleotide Thyroid Cancer Marker(s) in samples of the same type obtained from control patients not afflicted with thyroid cancer or a lower grade of thyroid cancer or from a sample from the patient taken at a different time, wherein altered levels of Polynucleotide Thyroid Cancer Marker(s) relative to the corresponding control levels of Polynucleotide Thyroid Cancer Marker(s) is an indication of the aggressiveness or metastatic potential of the thyroid cancer.

In a particular method of the invention for assessing whether a patient is afflicted with an aggressive or metastatic thyroid cancer, and in particular ATC, higher levels of Ep-ICD and/or or optionally β-catenin, in a sample relative to the corresponding control levels is an indication that the patient is afflicted with an aggressive or metastatic thyroid cancer.

Within certain embodiments, the amount of nucleic acid that is mRNA is detected via amplification reactions such as polymerase chain reaction (PCR) using, for example, at least one oligonucleotide primer that hybridizes to a Polynucleotide Thyroid Cancer Marker(s) or a complement of such polynucleotide. Within other embodiments, the amount of mRNA is detected using a hybridization technique, employing an oligonucleotide probe that hybridizes to a Polynucleotide Thyroid Cancer Marker(s), or a complement thereof.

When using mRNA detection, the method may be carried out by combining isolated mRNA with reagents to convert to cDNA according to standard methods; treating the converted cDNA with amplification reaction reagents along with an appropriate mixture of primers to produce amplification products; and analyzing the amplification products to detect the presence of Polynucleotide Thyroid Cancer Marker(s) in the sample. For mRNA the analyzing step may be accomplished using RT-PCR analysis to detect the presence of Polynucleotide Thyroid Cancer Marker(s). The analysis step may be accomplished by quantitatively detecting the presence of Polynucleotide Thyroid Cancer Marker(s) in the amplification product, and comparing the quantity of Polynucleotide Thyroid Cancer Marker(s), detected against a panel of expected values for known presence or absence in normal and malignant samples (e.g. tissue sample, in particular a tissue sample from patients with a different stage of thyroid cancer), derived using similar primers.

Therefore, the invention provides a method wherein mRNA is detected by (a) isolating mRNA from a sample and combining the mRNA with reagents to convert it to cDNA; (b) treating the converted cDNA with amplification reaction reagents and nucleic acid primers that hybridize to a Polynucleotide Thyroid Cancer Marker(s) to produce amplification products; (d) analyzing the amplification products to detect an amount of mRNA Polynucleotide Thyroid Cancer Marker(s); and (e) comparing the amount of mRNA to an amount detected against a panel of expected values for normal tissue and malignant tissue (e.g., tissue from patients with a different stage of thyroid cancer) derived using similar nucleic acid primers.

Protein based methods can also be used for diagnosing and monitoring thyroid cancer, in particular the aggressiveness or metastatic potential of thyroid cancer, more particularly ATC, in a subject comprising detecting Thyroid Cancer Markers in a sample from the subject. Thyroid Cancer Markers may be detected using a binding agent for Thyroid Cancer Markers, preferably antibodies specifically reactive with Thyroid Cancer Markers, or parts thereof.

The invention provides a method of assessing whether a patient is afflicted with thyroid cancer, in particular aggressive or metastatic thyroid cancer, more particularly ATC, which comprises comparing:
   (a) levels of Polypeptide Thyroid Cancer Markers in a sample from the patient; and
   (b) control levels of Polypeptide Thyroid Cancer Markers in a non-cancer sample or sample from a patient with a lower grade of thyroid cancer or from a sample from the patient taken at a different time, wherein significantly different levels of Polypeptide Thyroid Cancer Markers in the sample from the patient compared with the control levels (e.g. higher in the patient samples) is an indication that the patient is afflicted with thyroid cancer or an aggressive or metastatic thyroid cancer, in particular ATC.

In another aspect the invention provides methods for determining the presence or absence of thyroid cancer or the aggressiveness or metastatic potential of a thyroid cancer in a patient, in particular ATC, comprising the steps of (a) contacting a biological sample obtained from a patient with a binding agent that specifically binds to a Polypeptide Thyroid Cancer Marker(s); and (b) detecting in the sample an amount of Polypeptide Thyroid Cancer Marker(s) that binds to the binding agent(s), relative to a predetermined standard or cut-off value, and therefrom determining the presence or absence of aggressiveness or metastatic potential of thyroid cancer in the patient.

In an embodiment, the invention relates to a method for detecting, diagnosing, staging and monitoring thyroid cancer in a subject by quantitating Polypeptide Thyroid Cancer Marker(s) in a biological sample from the subject comprising (a) reacting the biological sample with an antibody specific for Polypeptide Thyroid Cancer Marker(s) which is directly or indirectly labelled with a detectable substance; and (b) detecting the detectable substance.

In another embodiment, the invention provides a method of using antibodies to detect expression of Polypeptide Thyroid Cancer Marker(s) in a sample, the method comprising: (a) combining antibodies specific for a Polypeptide Thyroid Cancer Marker(s) with a sample under conditions which allow the formation of antibody:protein complexes; and (b) detecting complex formation, wherein complex formation indicates expression of a Polypeptide Thyroid Cancer Marker(s) in the sample. Expression may be compared with standards and is diagnostic of thyroid cancer or the aggressiveness or metastatic potential of the thyroid cancer, in particular ATC.

In an aspect, the invention provides a method for monitoring the progression of thyroid cancer in a patient, the method comprising:
   (a) detecting Polypeptide Thyroid Cancer Marker(s) in a patient sample at a first time point; and
   (b) repeating step (a) at a subsequent point in time; and
   (c) comparing the levels detected in (a) and (b), and thereby monitoring the progression of thyroid cancer in the patient.

The invention further relates to a method of assessing the efficacy of a therapy for thyroid cancer, more particularly aggressive or metastatic thyroid cancer in a patient. This method comprises comparing:
(a) levels of Thyroid Cancer Markers in a first sample obtained from the patient prior to providing at least a portion of the therapy to the patient; and
(b) levels of Thyroid Cancer Markers in a second sample obtained from the patient following therapy.

Significantly different levels of Thyroid Cancer Markers in the second sample, relative to the first sample, is an indication that the therapy is efficacious for inhibiting thyroid cancer, more particularly anaplastic thyroid carcinoma. In an embodiment, the method is used to assess the efficacy of a therapy for inhibiting thyroid cancer, more particularly aggressive or metastatic thyroid cancer, and lower levels of nuclear Ep-ICD, and optionally cytoplasmic Ep-ICD, nuclear β-catenin or cytoplasmic β-catenin, in the second sample relative to the first sample, is an indication that the therapy is efficacious for inhibiting the cancer or metastasis. The therapy may be any therapy for treating thyroid cancer including but not limited to chemotherapy, immunotherapy, gene therapy, radiation therapy, and surgical removal of tissue. Therefore, the method can be used to evaluate a patient before, during, and after therapy, for example, to evaluate the reduction in tumor burden, aggressiveness or metastatic potential of the tumor.

The invention contemplates a method for determining the effect of an environmental factor on thyroid tissue or thyroid cancer comprising comparing Thyroid Cancer Markers in the presence and absence of the environmental factor.

The invention also provides a method for assessing the potential efficacy of a test agent for treating thyroid cancer, and a method of selecting an agent for treating thyroid cancer.

The invention contemplates a method of assessing the potential of a test compound to contribute to thyroid cancer comprising:
(a) maintaining separate aliquots of diseased cells in the presence and absence of the test compound; and
(b) comparing the levels of Thyroid Cancer Markers in each of the aliquots.

A significant difference between the levels of markers in an aliquot maintained in the presence of (or exposed to) the test compound relative to the aliquot maintained in the absence of the test compound, indicates that the test compound potentially contributes to thyroid cancer.

The invention also provides a pharmaceutical composition or diagnostic composition comprising Thyroid Cancer Markers or agents that interact with Thyroid Cancer Markers. In particular, the invention provides a pharmaceutical composition or diagnostic composition comprising Polypeptide Thyroid Cancer Markers, or agents that bind to such markers, or hybridize to or amplify Polynucleotide Thyroid Cancer Markers.

In an embodiment, the composition comprises a probe that specifically hybridizes to a Polynucleotide Thyroid Cancer Marker or a fragment thereof. In another embodiment a composition is provided comprising a specific primer(s) pair capable of amplifying a Polynucleotide Thyroid Cancer Marker using polymerase chain reaction methodologies. In a still further embodiment, the composition comprises a binding agent(s) (e.g. antibody) that binds to a Polypeptide Thyroid Cancer Marker or a fragment thereof. Probes, primers, and binding agents can be labeled with a detectable substance.

In an embodiment, a pharmaceutical composition or diagnostic composition of the invention comprises antibodies specific for Ep-ICD, β-catenin and/or EpEx. In an embodiment, a pharmaceutical composition or diagnostic composition of the invention comprises nucleotides (e.g. probes) that hybridize to polynucleotides encoding Ep-ICD, β-catenin and/or EpEx. In an embodiment, a diagnostic composition of the invention comprises primers that amplify polynucleotides encoding Ep-ICD, β-catenin and/or EpEx.

In another aspect, the invention relates to use of an agent that interacts with a Thyroid Cancer Marker in the manufacture of a composition for diagnosing thyroid cancer, in particular the aggressiveness or metastatic potential of a thyroid cancer, more particularly ATC.

The methods of the invention may comprise detecting Wnt Proteins and polynucleotides encoding the Wnt Proteins. The methods of the invention may also comprise detecting additional markers associated with thyroid cancer such as galectin-3, thyroglobulin, E-cadherin, beta-actin, FHL2 and Lef-1. Further, the amount of Thyroid Cancer Markers may be mathematically combined with other markers of thyroid cancer. In an embodiment the invention provides a method for detecting or diagnosing thyroid cancer in a subject comprising:
(a) determining the amount of Thyroid Cancer Markers in a sample from the subject;
(b) determining the amount of other markers associated with thyroid cancer in particular markers selected from the group consisting of galectin-3, thyroglobulin, E-cadherin, c-Myc, beta-actin, FHL2 and Lef-1 in the sample;
(c) mathematically combining the results of step (a) and step (b) to provide a mathematical combination; and
(d) comparing or correlating the mathematical combination to the presence of thyroid cancer or aggressiveness or metastatic potential of thyroid cancer.

The combination is preferably compared to a mathematical combination for a predetermined standard. In particular aspects, the invention provides a method for detecting, characterizing or diagnosing thyroid cancer by determining the combination of Thyroid Cancer Markers and one or both of galectin-3 and thyroglobulin in a sample from a subject.

The invention also includes kits for carrying out methods of the invention. In an aspect the invention provides a kit for detecting, diagnosing or characterizing thyroid cancer comprising Thyroid Cancer Markers. In a particular aspect, the invention provides a test kit for diagnosing or characterizing thyroid cancer in a subject which comprises an agent that interacts with a Thyroid Cancer Marker(s). In an embodiment, the kit is for assessing whether a patient is afflicted with aggressive or metastatic thyroid cancer, in particular ATC, and it comprises reagents for identifying and/or assessing levels of Ep-ICD, β-catenin and optionally EpEx or preferably Ep-ICD and optionally EpEx or in another embodiment Ep-ICD and EpEx.

The invention therefore contemplates an in vivo method comprising administering to a mammal one or more agent that carries a label for imaging and binds to a Thyroid Cancer Marker(s), and then imaging the mammal. According to a preferred aspect of the invention, an in vivo method for imaging thyroid cancer is provided comprising:
(a) injecting a patient with an agent that binds to a Thyroid Cancer Marker(s), the agent carrying a label for imaging the thyroid cancer;
(b) allowing the agent to incubate in vivo and bind to the Thyroid Cancer Marker(s); and
(c) detecting the presence of the label localized to the thyroid cancer.

In an embodiment of the invention the agent is an antibody which recognizes the Thyroid Cancer Marker(s). In another embodiment of the invention the agent is a chemical entity which recognizes the Thyroid Cancer Marker(s).

The agent carries a label to image the Thyroid Cancer Marker(s). Examples of labels useful for imaging are radiolabels, fluorescent labels (e.g., fluorescein and rhodamine), nuclear magnetic resonance active labels, positron emitting isotopes detectable by a positron emission tomography ("PET") scanner, chemiluminescers such as luciferin, and enzymatic markers such as peroxidase or phosphatase. Short-range radiation emitters, such as isotopes detectable by short-range detector probes can also be employed.

The invention also contemplates the localization or imaging methods described herein using multiple markers for thyroid cancer.

The invention provides methods of treating thyroid cancer, in particular ATC, comprising administering to a subject or using a pharmaceutical composition of the invention. In an aspect, the invention provides antagonists (e.g. antibodies) specific for Ep-ICD or β-catenin that can be used therapeutically to destroy or inhibit the growth of thyroid cancer cells, (e.g. ATC cells), or to block Ep-ICD or β-catenin activity. In addition, Ep-ICD or β-catenin may be used in various immunotherapeutic methods to promote immune-mediated destruction or growth inhibition of tumors expressing Ep-ICD or β-catenin.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which:

FIGS. 7A-7E are plots showing viability of the indicated cell lines (as measured by absorbance) when treated with increasing concentrations (pM) of VB4-845/VB6-845 (VB4) or control (MOC31) (FIG. 7A: WRO cells; FIG. 7B: ARO cells; FIG. 7C: medullary thyroid cancer cell line, TT; FIG. 7D: papillary cell line, TPC-1; and FIG. 7E: anaplastic cell line, CAL-62).

FIG. 27 is a Kaplan Meier survival analysis for ESLI. Kaplan Meier survival analysis showing significant association with reduced disease free survival (DFS) in ESLI positive PTC patients (p=0.039) with a mean DFS=133 months compared to ESLI negative patients with a mean DFS=210 months.

DETAILED DESCRIPTION OF THE INVENTION

Figure 1:
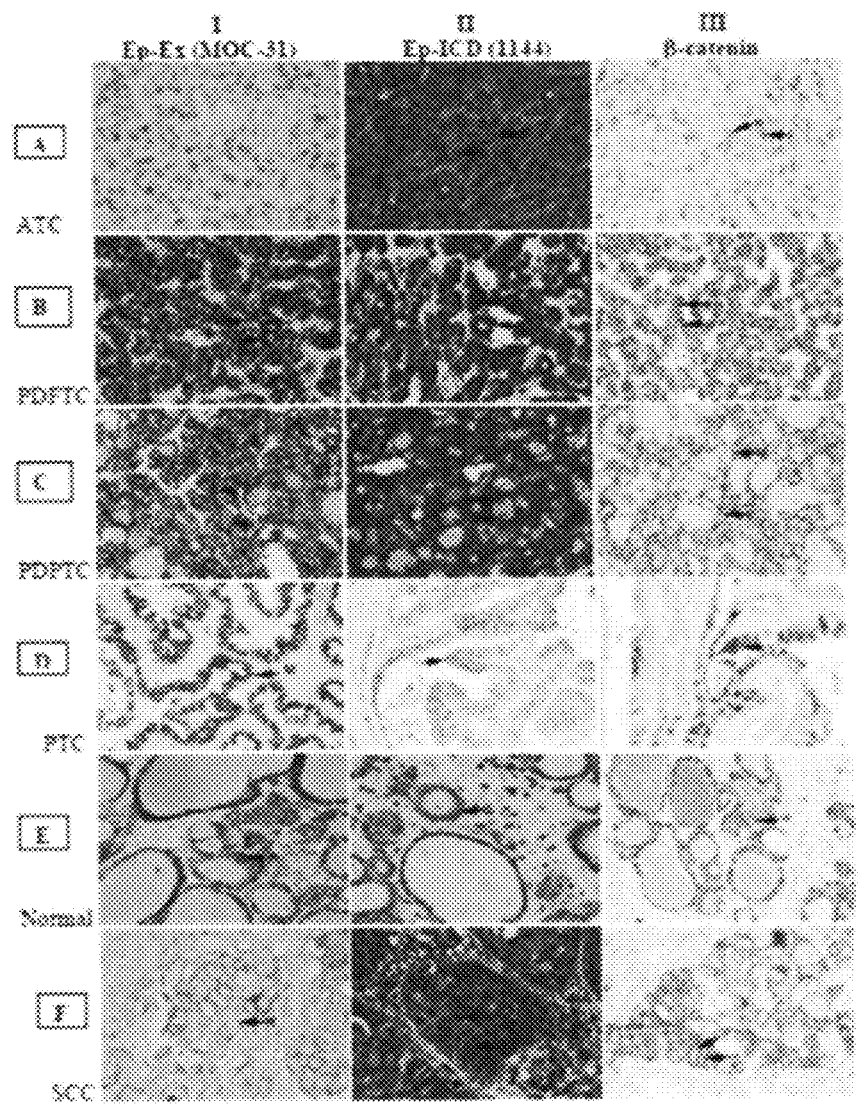
FIG. 1. Immunohistochemical analysis of EpEx, Ep-ICD and β-catenin in thyroid cancers. The anaplastic thyroid cancers did not show detectable membranous EpEx staining (IA); all the other subtypes of thyroid cancers analyzed and normal thyroid tissues showed plasma membranous EpEX staining (IB-IF). Nuclear Ep-ICD staining was only observed in undifferentiated and poorly differentiated thyroid cancers (IIA-IIC, and IIF), but not in well differentiated thyroid cancer and normal thyroid tissue (IID, IIE). Correlated with nuclear Ep-ICD staining, nuclear or cytoplasmic β-catenin staining was observed in aggressive thyroid cancers (IIIA-IIIC, and IIIF), while membranous staining was observed in less aggressive thyroid cancers and normal thyroid tissue (IIID, IIIE).

The invention relates to newly discovered correlations between expression of Thyroid Cancer Markers and thyroid cancer, in particular aggressiveness or metastatic potential of a thyroid cancer, more particularly ATC. The Thyroid Cancer Markers described herein provide methods for diagnosing, detecting or characterizing thyroid cancer, in particular aggressiveness or metastatic potential of a thyroid cancer, more particularly ATC. Methods are provided for diagnosing or detecting the presence or absence of aggressive or metastatic thyroid cancer in a sample, and for monitoring the progression of thyroid cancer, as well as providing information about characteristics of a thyroid carcinoma that are relevant to the diagnosis and characterization of thyroid carcinoma in a patient.

Unless defined otherwise, all technical and scientific terms used herein have the same meaning as commonly understood by one of ordinary skill in the art to which this invention belongs. The following definitions supplement those in the art and are directed to the present application and are not to be imputed to any related or unrelated case. Although any methods and materials similar or equivalent to those described herein can be used in the practice of the invention, particular materials and methods are described herein.

Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. As used herein and in the appended claims, the singular forms "a", "an", and "the" include plural reference unless the context clearly dictates otherwise.

The term "thyroid cancer" refers to any malignant process of the thyroid gland. Examples of thyroid cancers include, but are not limited to, papillary thyroid carcinoma, follicular variant of papillary thyroid carcinoma, follicular carcinoma, Hurthle cell tumor, anaplastic thyroid carcinoma, medullary thyroid cancer, thyroid lymphoma, poorly differentiated thyroid cancer and thyroid angiosarcoma. In aspects of the invention, the thyroid cancer is medullary thyroid cancer. In aspects of the invention, the thyroid cancer is an aggressive cancer or has metastatic potential, in particular an aggressive medullary or follicular thyroid cancer or a medullary or follicular thyroid cancer with metastatic potential. In aspects of the invention, the thyroid cancer is anaplastic thyroid carcinoma (ATC).

"Metastatic potential" refers to the ability or possibility of a cancer cell moving from the initial site (i.e. thyroid) to other sites in the body.

The term "sample" and the like mean a material known or suspected of expressing or containing Thyroid Cancer Markers, or binding agents such as antibodies specific for Polypeptide Thyroid Cancer Markers. The sample may be derived from a biological source ("biological sample"), such as tissues (e.g., biopsy samples), extracts, or cell cultures, including cells (e.g. tumor cells), cell lysates, and biological or physiological fluids, such as, for example, whole blood, plasma, serum, saliva, cerebral spinal fluid, sweat, urine, milk, peritoneal fluid and the like. A sample may be used directly as obtained from the source or following a pretreatment to modify the character of the sample, such as preparing plasma from blood, diluting viscous fluids, and the like. In certain aspects of the invention, the sample is a human physiological fluid, such as human serum. In certain aspects of the invention, the sample is a biopsy sample. In certain aspects of the invention the sample is a benign, malignant, or normal tissue sample.

The samples that may be analyzed in accordance with the invention include polynucleotides from clinically relevant sources, preferably expressed RNA or a nucleic acid derived therefrom (cDNA or amplified RNA derived from cDNA that incorporates an RNA polymerase promoter). As will be appreciated by those skilled in the art, the target polynucleotides can comprise RNA, including, without limitation total cellular RNA, poly(A)$^+$ messenger RNA (mRNA) or fraction thereof, cytoplasmic mRNA, or RNA transcribed from cDNA (i.e., cRNA).

Target polynucleotides can be detectably labeled at one or more nucleotides using methods known in the art. The label is preferably uniformly incorporated along the length of the RNA, and more preferably, is carried out at a high degree of efficiency. The detectable label can be, without limitation, a luminescent label, fluorescent label, bio-luminescent label, chemi-luminescent label, radiolabel, and colorimetric label.

Target polynucleotides from a patient sample can be labeled differentially from polynucleotides of a standard. The standard can comprise target polynucleotides from normal individuals (e.g. those not afflicted with or pre-disposed to thyroid cancer, in particular pooled from samples from normal individuals or patients with a different disease stage). The target polynucleotides can be derived from the same individual, but taken at different time points, and thus indicate the efficacy of a treatment by a change in expression of the markers, or lack thereof, during and after the course of treatment.

The terms "subject", "patient" and "individual" are used interchangeably herein and refer to a warm-blooded animal such as a mammal that is afflicted with, or suspected of having, being pre-disposed to, or being screened for thyroid cancer, in particular actual or suspected aggressive thyroid cancer or metastatic potential, more particularly ATC. The term includes but is not limited to domestic animals, sports animals, primates and humans. Preferably, the terms refer to a human.

As used herein, the term "subject suspected of having" thyroid cancer refers to a subject that presents one or more symptoms indicative of a thyroid cancer (e.g., a noticeable lump or mass) or is being screened for a cancer (e.g., during a routine physical). A subject suspected of having thyroid carcinoma may also have one or more risk factors. A subject suspected of having thyroid cancer has generally not been tested for cancer. However, a "subject suspected of having" thyroid cancer encompasses an individual who has received an initial diagnosis but for whom the stage of cancer is not known. The term further includes people who once had cancer (e.g., an individual in remission).

As used herein, the term "subject at risk for thyroid cancer" refers to a subject with one or more risk factors for developing thyroid cancer, in particular aggressive or metastatic thyroid cancer, more particularly ATC. Risk factors include, but are not limited to, gender, age, genetic predisposition, environmental exposure, previous incidents of cancer, pre-existing non-cancer diseases, and lifestyle.

As used herein, the term "characterizing thyroid cancer" in a subject refers to the identification of one or more properties of a cancer sample in a subject, including but not limited to the subject's prognosis or survival. Cancers may be characterized by the identification of the expression of one or more markers, including but not limited to, the Thyroid Cancer Markers disclosed herein.

As used herein, the term "treat" or "treating" refers to any method used to partially or completely alleviate, ameliorate, relieve, inhibit, prevent, delay onset of, reduce severity of and/or reduce incidence of one or more symptoms or features of a particular condition. Treatment may be administered to a subject who does not exhibit signs of a condition and/or exhibits only early signs of the condition for the purpose of decreasing the risk of developing pathology associated with the condition. Thus, depending on the state of the subject, the term in some aspects of the invention may refer to preventing a condition, and includes preventing the onset, or preventing the symptoms associated with a condition. The term also includes maintaining the condition and/or symptom such that the condition and/or symptom do not progress in severity. A treatment may be either performed in an acute or chronic way. The term also refers to reducing the severity of a condition or symptoms associated with such condition prior to affliction with the condition. Such prevention or reduction of the severity of a condition prior to affliction refers to administration of a therapy to a subject that is not at the time of administration afflicted with the condition. Preventing also includes preventing the recurrence of a condition, or of one or more symptoms associated with such condition. The terms "treatment" and "therapeutically" refer to the act of treating, as "treating" is defined above. The purpose of intervention is to combat the condition and includes the administration of therapy to prevent or delay the onset of the symptoms or complications, or alleviate the symptoms or complications, or eliminate the condition.

"Polypeptide" and "protein" are used interchangeably herein and indicate at least one molecular chain of amino acids linked through covalent and/or non-covalent bonds. The terms include peptides, oligopeptides, and proteins, and post-translational modifications of the polypeptides, e.g. glycosylations, acetylations, phosphorylations, and the like. Protein fragments, analogues, mutated or variant proteins, fusion proteins, and the like, are also included within the meaning of the terms.

The term "EpCAM" refers to a type I membrane protein comprising an epidermal growth factor (EGF)-like domain and a thyroglobulin repeat domain. In particular, it is composed of a large extracellular domain (265 amino acids) (EpEx), a single transmembrane part of 23 amino acids (amino acids 266-288 in SEQ ID NO. 1), and a short cytoplasmic domain of 26 amino acids (Ep-ICD—amino acids 289-413 in SEQ ID NO. 1). Two EGF-like repeats are located within the extracellular domain (Balzar et al., 2001). The mature enzyme consists of 314 amino acids. [See Baeuerie P A and O Gires, British Journal of Cancer (2007) 96, pages 417-423 for a review of EpCAM (CD326).] The term includes native-sequence polypeptides, isoforms, precursors, and chimeric or fusion proteins of EpCAM, in particular human EpCAM. EpCAM polypeptides that can be employed in the present invention include, without limitation, polypeptides comprising the sequences found in Accession No. NP_002345 and SEQ ID NO. 1. In particular aspects of the invention, domains of EpCAM are utilized in the methods of the present invention, in particular Ep-ICD and EpEx.

The term "β-catenin" refers to an adherens junction protein which contains several armadillo repeats, i.e. sequences of approximately 50 amino acids involved in protein-protein interactions. Each repeat consists of three helices, with helix 1 and 3 antiparallel to each other and perpendicular to helix 2, and a conserved glycine residue that allows the sharp turn between helices 1 and 2 (see Aberle H, et al, J Cell Sci. 1994 December; 107 (Pt 12):3655-63; van Hengel, J., et al, Cytogenet. Cell Genet. 70 (1-2), 68-70 (1995)). The term includes native-sequence polypeptides, isoforms, precursors, and chimeric or fusion proteins of β-catenin, in particular human β-catenin. β-catenin polypeptides that can be employed in the present invention include, without limitation, polypeptides comprising the sequences found in Swiss-Prot Accession No: P35222.1, Genbank NP_001091679 and SEQ ID NO. 7.

"Wnt Proteins" refers to a family of highly conserved secreted signaling molecules that regulate cell-to-cell interactions during embryogenesis. Wnt Proteins include proteins that regulate the production of Wnt signaling molecules, their interactions with receptors on target cells and the physiological responses of target cells that result from contact of cells with Wnt ligands, includes target proteins. Wnt Proteins include without limitation Wnt proteins (e.g., Wnt1, Wnt3, Wnt4, Wnt5B, Wnt7A, Wnt10A, Wnt10B), cell-surface receptors of the Frizzled (FRZ) family, Dishevelled family proteins, axin proteins (e.g. Axin1, Axin2), WTX, PORC1, RSPO4, VANGL1, GSK-3, APC, TCF/LEF family transcription factors (e.g. TCF4), the transmembrane protein LRP, sclerostin, trimeric G proteins, CK1, GSK3, Norrin, WTX, PORC1, RSPO4, VANGL1, and target proteins such as C-myc. (See MacDonald B T, et al, Dev Cell. 2009 July; 17(1):9-26; Cadigan K M Curr Biol. 2008 Oct. 28; 18(20): R943-7.)

A "native-sequence polypeptide" comprises a polypeptide having the same amino acid sequence of a polypeptide derived from nature. Such native-sequence polypeptides can be isolated from nature or can be produced by recombinant or synthetic means. The term specifically encompasses naturally occurring truncated or secreted forms of a polypeptide, polypeptide variants including naturally occurring variant forms (e.g. alternatively spliced forms or splice variants), and naturally occurring allelic variants.

The term "polypeptide variant" means a polypeptide having at least about 10%, 20%, 30%, 40%, 45%, 50%, 55%, 60%, 65%, 70%, 75%, 80%, 85%, 90%, 95%, 97%, 98%, or 99% amino acid sequence identity, particularly at least about 70-80%, more particularly at least about 85%, still more particularly at least about 90%, most particularly at least about 95%, 97%, or 99% amino acid sequence identity with a native-sequence polypeptide. Particular polypeptide variants have at least 70-80%, 85%, 90%, 95%, 97% or 99% amino acid sequence identity to the sequences identified in Accession No. NP_002345 and SEQ ID NO: 1 or Swiss-Prot Accession No: P35222.1, Genbank NP_001091679 and SEQ ID NO. 7. Such variants include, for instance, polypeptides wherein one or more amino acid residues are added to, or deleted from, the N- or C-terminus of the full-length or mature sequences of the polypeptide, including variants from other species, but exclude a native-sequence polypeptide. In aspects of the invention variants retain the immunogenic activity of the corresponding native-sequence polypeptide.

Sequence identity of two amino acid sequences or of two nucleic acid sequences is defined as the percentage of amino acid residues or nucleotides in a candidate sequence that are identical with the amino acid residues in a polypeptide or nucleic acid sequence, after aligning the sequences and introducing gaps, if necessary, to achieve the maximum percent sequence identity, and not considering any conservative substitutions as part of the sequence identity. Alignment for purposes of determining percent amino acid or nucleic acid sequence identity can be achieved in various conventional ways, for instance, using publicly available computer software including the GCG program package (Devereux J. et al., Nucleic Acids Research 12(1): 387, 1984); BLASTP, BLASTN, and FASTA (Atschul, S. F. et al. J. Molec. Biol. 215: 403-410, 1990). The BLAST X program is publicly available from NCBI and other sources (BLAST Manual, Altschul, S. et al. NCBI NLM NIH Bethesda, Md. 20894; Altschul, S. et al. J. Mol. Biol. 215: 403-410, 1990). Skilled artisans can determine appropriate parameters for measuring alignment, including any algorithms needed to achieve maximal alignment over the full length of the sequences being compared. Methods to determine identity and similarity are codified in publicly available computer programs.

Polypeptide variants include polypeptides comprising amino acid sequences sufficiently identical to or derived from the amino acid sequence of a native polypeptide which includes fewer amino acids than the full-length polypeptides. A portion or fragment of a polypeptide can be a polypeptide which is for example, 3-5, 8-10, 10, 15, 15-20, 20, 25, 30, 35, 40, 45, 50, 60, 70, 80, 90, 100 or more amino acids in length. Portions or fragments in which regions of a polypeptide have deleted can be prepared by recombinant techniques and can be evaluated for one or more functional activities such as the ability to form antibodies specific for a polypeptide. A portion or fragment of a polypeptide may comprise a domain of the polypeptide, in particular an extracellular domain or intracellular domain.

An allelic variant may also be created by introducing substitutions, additions, or deletions into a nucleic acid encoding a native polypeptide sequence such that one or more amino acid substitutions, additions, or deletions are introduced into the encoded protein. Mutations may be introduced by standard methods, such as site-directed mutagenesis and PCR-mediated mutagenesis. In an embodiment, conservative substitutions are made at one or more predicted non-essential amino acid residues. A "conservative amino acid substitution" is one in which an amino acid residue is replaced with an amino acid residue with a similar side chain, several of which are known in the art.

A naturally occurring allelic variant may contain conservative amino acid substitutions from the native polypeptide sequence or it may contain a substitution of an amino acid from a corresponding position in polypeptide homolog, for example, a murine polypeptide.

A polypeptide disclosed herein includes chimeric or fusion proteins. A "chimeric protein" or "fusion protein" comprises all or part (preferably biologically active) of the polypeptide operably linked to a heterologous polypeptide (i.e., a different polypeptide). Within the fusion protein, the term "operably linked" is intended to indicate that the polypeptide and the heterologous polypeptide are fused in-frame to each other. The heterologous polypeptide can be fused to the N-terminus or C-terminus of the polypeptide. A useful fusion protein is a GST fusion protein in which a polypeptide is fused to the C-terminus of GST sequences. Another example of a fusion protein is an immunoglobulin fusion protein in which all or part of a polypeptide is fused to sequences derived from a member of the immunoglobulin protein family. Chimeric and fusion proteins can be produced by standard recombinant DNA techniques.

Polypeptides used in the methods disclosed herein may be isolated from a variety of sources, such as from human tissue types or from other sources, or prepared by recombinant or synthetic methods, or by any combination of these and similar techniques.

"Polynucleotide" refers to a polymeric form of nucleotides of any length, either ribonucleotides or deoxyribonucleotides. The term includes double- and single-stranded DNA and RNA, modifications such as methylation or capping and unmodified forms of the polynucleotide. The terms "polynucleotide" and "oligonucleotide" are used interchangeably herein. A polynucleotide may, but need not, include additional coding or non-coding sequences, or it may, but need not, be linked to other molecules and/or carrier or support materials. Polynucleotides for use in the methods of the invention may be of any length suitable for a particular method. In certain applications the term refers to antisense nucleic acid molecules (e.g. an mRNA or DNA strand in the reverse orientation to a sense Polynucleotide Thyroid Cancer Markers).

Polynucleotide Thyroid Cancer Markers include polynucleotides encoding Polypeptide Thyroid Cancer Markers, including a native-sequence polypeptide, a polypeptide variant including a portion of a Polypeptide Thyroid Cancer Marker, an isoform, precursor, and a chimeric polypeptide. A polynucleotide encoding an EpCAM polypeptide that can be employed in the present invention includes, without limitation, nucleic acids comprising a sequence of Accession No. UniProtKB/TrEMBL Q6FG26, UniProtKB/Swiss-Prot 16422, Genbank NM_002354 and BC014785 or SEQ ID NO. 2 or fragments thereof. A polynucleotide encoding a β-catenin polypeptide that can be employed in the present invention includes, without limitation, nucleic acids comprising a sequence of GenBank Accession Nos. NM_001904.3, NM_001098209, or NM_001098210, or SEQ ID NO. 8, 9 or 10.

Polynucleotides used in the methods of the invention include complementary nucleic acid sequences, and nucleic acids that are substantially identical to these sequences (e.g. at least about 10%, 20%, 30%, 40%, or 45%, preferably 50%, 55%, 60%, 65%, 70%, 75%, 80%, 85%, 90%, 95%, 97%, 98%, or 99% sequence identity).

Polynucleotides also include sequences that differ from a nucleic acid sequence due to degeneracy in the genetic code. As one example, DNA sequence polymorphisms within the nucleotide sequence of a Thyroid Cancer Marker disclosed herein may result in silent mutations that do not affect the amino acid sequence. Variations in one or more nucleotides may exist among individuals within a population due to natural allelic variation. DNA sequence polymorphisms may also occur which lead to changes in the amino acid sequence of a polypeptide.

Polynucleotides which may be used in the methods disclosed herein also include nucleic acids that hybridize under stringent conditions, preferably high stringency conditions to a nucleic acid sequence of a Polynucleotide Thyroid Cancer Marker. Appropriate stringency conditions which promote DNA hybridization are known to those skilled in the art, or can be found in Ausubel et al., (eds) Current Protocols in Molecular Biology, John Wiley & Sons, N.Y. (1989), 6.3.1-6.3.6. Generally, stringent conditions may be selected that are about 5° C. lower than the thermal melting point (Tm) for the specific sequence at a defined ionic strength and pH. The Tm is the temperature (under defined ionic strength, pH, and nucleic acid concentration) at which 50% of the probes complementary to a target sequence hybridize at equilibrium to the target sequence. Generally, stringent conditions will be those in which the salt concentration is less than about 1.0M sodium ion or other salts (e.g. about 0.01 to 1.0M sodium ion) and the temperature is at least about 30° C. for short probes, primers or oligonucleotides (e.g. 10-50 nucleotides) and at least 60° C. for longer probes, primers and oligonucleotides. For example, a hybridization may be conducted at 6.0× sodium chloride/sodium citrate (SSC) at about 45° C., followed by a wash of 2.0×SSC at 50° C., or at 42° C. in a solution containing 6×SCC, 0.5% SDS and 50% formamide followed by washing in a solution of 0.1×SCC and 0.5% SDS at 68° C.

Polynucleotide Thyroid Cancer Markers also include truncated nucleic acids or nucleic acid fragments and variant forms of the nucleic acids disclosed or referenced herein that arise by alternative splicing of an mRNA corresponding to a DNA. A fragment of a polynucleotide includes a polynucleotide sequence that comprises a contiguous sequence of approximately at least about 6 nucleotides, in particular at least about 8 nucleotides, more particularly at least about 10-12 nucleotides, and even more particularly 15-20 nucleotides that correspond to (i.e. identical or complementary to), a region of the specified nucleotide sequence.

"Significantly different" levels of markers or a "significant difference" in marker levels in a patient sample compared to a control or standard (e.g. normal levels, levels from a different disease stage, or levels in other samples from a patient) may represent levels that are higher or lower than the standard error of the detection assay, preferably the levels are at least about 1.5, 2, 3, 4, 5, 6, 7, 8, 9 or 10 times higher or lower, respectively, than the control or standard.

"Microarray" and "array," refer to nucleic acid or nucleotide arrays or protein or peptide arrays that can be used to detect biomolecules associated with thyroid cancer, for instance to measure gene expression. A variety of arrays are available commercially, such as, for example, as the in situ synthesized oligonucleotide array GeneChip™ made by Affymetrix, Inc. or the spotted cDNA array, LifeArray™ made by Incyte Genomics Inc. The preparation, use, and analysis of microarrays are well known to those skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (I 995) PCT application WO95/35505; Heller, R. A. et al. (1997) Proc. Natl. Acad. Sci. 94:2150-2155; and Heller, M. J. et al. (1997) U.S. Pat. No. 5,605,662).

"Binding agent" refers to a substance such as a polypeptide, antibody, ribosome, or aptamer that specifically binds to a Polypeptide Thyroid Cancer Marker. A substance "specifically binds" to a Polypeptide Thyroid Cancer Marker if it reacts at a detectable level with the polypeptide, and does not react detectably with peptides containing unrelated sequences or sequences of different polypeptides. Binding properties may be assessed using an ELISA, which may be readily performed by those skilled in the art.

A binding agent may be a ribosome, with or without a peptide component, an RNA or DNA molecule, or a polypeptide. A binding agent may be a polypeptide that comprises a Polypeptide Thyroid Cancer Marker sequence, a peptide variant thereof, or a non-peptide mimetic of such a sequence. By way of example a Polypeptide Thyroid Cancer Marker sequence may be a peptide portion of the polypeptide that is capable of modulating a function mediated by the polypeptide.

An aptamer includes a DNA or RNA molecule that binds to nucleic acids and proteins. An aptamer that binds to a Thyroid Cancer Marker can be produced using conventional techniques, without undue experimentation. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Antibodies for use in the present invention include but are not limited to synthetic antibodies, monoclonal antibodies, polyclonal antibodies, recombinant antibodies, antibody fragments (such as Fab, Fab', F(ab')$_2$), dAb (domain antibody; see Ward, et al, 1989, Nature, 341:544-546), antibody heavy chains, intrabodies, humanized antibodies, human antibodies, antibody light chains, single chain F$_{vs}$ (scFv) (e.g., including monospecific, bispecific etc), anti-idiotypic (ant-Id) antibodies, proteins comprising an antibody portion, chimeric antibodies (for example, antibodies which contain the binding specificity of murine antibodies, but in which the remaining portions are of human origin), derivatives, such as enzyme conjugates or labelled derivatives, diabodies, linear antibodies, disulfide-linked Fvs (sdFv), multispecific antibodies (e.g., bispecific antibodies), epitope-binding fragments of any of the above, and any other modified configuration of an immunoglobulin molecule that comprises an antigen recognition site of the required specificity. An antibody includes an antibody of any type (e.g. IgA, IgD, IgE, IgG, IgM and IgY), any class (e.g. IgG1, IgG2, IgG3, IgG4, IgA1 and IgA2), or any subclass (e.g. IgG2a and IgG2b), and the antibody need not be of any particular type, class or subclass. In certain embodiments of the invention the antibodies are IgG antibodies or a class or subclass thereof. An antibody may be from any animal origin including birds and mammals (e.g. human, murine, donkey, sheep, rabbit, goat, guinea pig, camel, horse, or chicken).

A "recombinant antibody" includes antibodies that are prepared, expressed, created or isolated by recombinant means, such as antibodies expressed using a recombinant expression vector transfected into a host cell, antibodies isolated from recombinant, combinatorial antibody libraries, antibodies isolated from an animal (e.g. a mouse or cow) that is transgenic and/or transchromosomal for human immunoglobin genes, or antibodies prepared, expressed, created or isolated by any other means that involves slicing of immunoglobulin gene sequences to other DNA sequences.

A "monoclonal antibody" refers to an antibody obtained from a population of homogenous or substantially homogenous antibodies. Generally each monoclonal antibody recognizes a single epitope on an antigen. In aspects of the invention, a monoclonal antibody is an antibody produced by a single hybridoma or other cell, and it specifically binds to only a Thyroid Cancer Marker as determined, for example by ELISA or other antigen-binding or competitive binding assay known in the art. The term is not limited to a particular method for making the antibody and for example they may be produced by the hybridoma method or isolated from phage libraries using methods known in the art.

Antibodies including monoclonal and polyclonal antibodies, fragments and chimeras, may be prepared using methods well known to those skilled in the art. Isolated native or recombinant Polypeptide Thyroid Cancer Markers may be utilized to prepare antibodies. See, for example, Kohler et al. (1975) Nature 256:495-497; Kozbor et al. (1985) J Immunol Methods 81:31-42; Cote et al. (1983) Proc Natl Acad Sci 80:2026-2030; and Cole et al. (1984) Mol Cell Biol 62:109-120 for the preparation of monoclonal antibodies; Huse et al. (1989) Science 246:1275-1281 for the preparation of monoclonal Fab fragments; and, Pound (1998) Immunochemical Protocols, Humana Press, Totowa, N.J. for the preparation of phagemid or B-lymphocyte immunoglobulin libraries to identify antibodies. Antibodies specific for Polypeptide Thyroid Cancer Markers may also be obtained from scientific or commercial sources. In an embodiment of the invention, antibodies are reactive against Polypeptide Thyroid Cancer Markers if they bind with a $K_a$ of greater than or equal to $10^{-7}$ M.

Examples of antibodies specific for EpCAM polypeptides are shown in Table 1.

The "status" of a marker refers to the presence, absence or extent/level of the marker or some physical, chemical or genetic characteristic of the marker. Such characteristics include without limitation, expression level, activity level, structure (sequence information), copy number, post-translational modification etc. The status of a marker may be directly or indirectly determined. In some embodiments status is determined by determining the level of a marker in the sample. The "level" of an element in a sample has its conventional meaning in the art, and includes quantitative determinations (e.g. mg/mL, fold change, etc) and qualitative determinations (e.g. determining the presence or absence of a marker or determining whether the level of the marker is high, low or even present relative to a standard).

The term "abnormal status" means that a marker's status in a sample is different from a reference status for the marker. A reference status may be the status of the marker in samples from normal subjects, averaged samples from subjects with the condition or sample(s) from the same subject taken at different times. An abnormal status includes an elevated, decreased, present or absent marker(s). Determining the level of a marker in a sample may include determining the level of the marker in a sample and abnormal status could be either lower levels (including undetectable levels) or higher levels (including any amount over zero) compared to a standard. A subject may have an increased likelihood of a condition disclosed herein if the status of a marker in the subject's sample is correlated with the condition (e.g. a level of the marker is closer to a standard or reference or is present in levels that exceed some threshold value where exceeding that value is correlated with the condition). A subject with an increased likelihood of a condition disclosed herein includes a subject with an abnormal status for a marker and as such the subject has a higher likelihood of the condition than if the subject did not have that status.

An "elevated status" means one or more characteristics of a marker are higher than a standard. In aspects of the invention, the term refers to an increase in a characteristic as compared to a standard. A "low status" means one or more characteristics of a marker are lower than a standard. In aspects of the invention, the term refers to a decrease in a characteristic as compared to a standard. A "negative status" means that one or more characteristic of a marker is absent or undetectable.

General Methods

A variety of methods can be employed for the diagnostic and prognostic evaluation of thyroid cancer involving Thyroid Cancer Markers and the identification of subjects with a predisposition to such disorders. Such methods may, for example, utilize Polynucleotide Thyroid Cancer Markers and fragments thereof, and binding agents (e.g. antibodies) directed against Polypeptide Thyroid Cancer Markers including peptide fragments. In particular, the polynucleotides and antibodies may be used, for example, for (1) the detection of the presence of polynucleotide mutations, or the detection of either over- or under-expression of mRNA, relative to a non-disorder state or the qualitative or quantitative detection of alternatively spliced forms of polynucleotide transcripts which may correlate with certain conditions or susceptibility toward such conditions; and (2) the detection of either an over- or an under-abundance of polypeptides relative to a non-disorder state or the presence of a modified (e.g., less than full length) polypeptide which correlates with a disorder state, or a progression toward a disorder state.

The methods described herein may be used to evaluate the probability of the presence of malignant cells, for example, in a group of cells freshly removed from a host. Such methods can be used to detect tumors, quantitate and monitor their growth, and help in the diagnosis and prognosis of disease. For example, higher levels of nuclear Ep-ICD, nuclear β-catenin or cytoplasmic β-catenin are indicative of aggressive thyroid cancer or metastatic thyroid cancer, in particular ATC.

In an aspect, the invention contemplates a method for determining the aggressiveness or stage of thyroid cancer, more particularly ATC, comprising producing a profile of levels of Polypeptide Thyroid Cancer Markers, and other markers associated with thyroid cancer, in cells from a patient, and comparing the profile with a reference to identify a profile for the test cells indicative of aggressiveness or stage of disease.

The methods of the invention require that the amount of Thyroid Cancer Markers quantitated in a sample from a subject being tested be compared to a predetermined standard or cut-off value. A standard may correspond to levels quantitated for another sample or an earlier sample from the subject, or levels quantitated for a control sample, in particular a sample from a subject with a lower grade cancer. Levels for control samples from healthy subjects or cancer subjects may be established by prospective and/or retrospective statistical studies. Healthy subjects who have no clinically evident disease or abnormalities may be selected for statistical studies. Diagnosis may be made by a finding of statistically different levels of Thyroid Cancer Markers compared to a control sample or previous levels quantitated for the same subject.

The invention also contemplates the methods described herein using multiple markers for thyroid cancer. Therefore, the invention contemplates a method for analyzing a biological sample for the presence of Thyroid Cancer Markers and other markers that are specific indicators of thyroid cancer. The methods described herein may be modified by including reagents to detect the other markers or polynucleotides encoding the markers. Examples of other markers include without limitation galectin-3, thyroglobulin, E-cadherin, beta-catenin, FHL2 and Lef-1, c-Myc, and beta-actin, in particular galectin-3.

Nucleic Acid Methods

As noted herein thyroid cancer, in particular aggressive thyroid cancer or a thyroid cancer with metastatic potential, more particularly ATC, may be detected based on the level of Polynucleotide Thyroid Cancer Markers in a sample. Techniques for detecting nucleic acid molecules such as polymerase chain reaction (PCR) and hybridization assays are well known in the art.

Probes may be used in hybridization techniques to detect polynucleotides. The technique generally involves contacting and incubating nucleic acids obtained from a sample from a patient or other cellular source with a probe under conditions favorable for the specific annealing of the probes to complementary sequences in the nucleic acids (e.g. under stringent conditions as discussed herein). After incubation, the non-annealed nucleic acids are removed, and the presence of nucleic acids that have hybridized to the probe if any are detected.

Nucleotide probes for use in the detection of polynucleotide sequences in samples may be constructed using conventional methods known in the art. The probes may comprise DNA or DNA mimics corresponding to a portion of an organism's genome, or complementary RNA or RNA mimics. The nucleic acids can be modified at the base moiety, at the sugar moiety, or at the phosphate backbone. DNA can be obtained using standard methods such as polymerase chain reaction (PCR) amplification of genomic DNA or cloned sequences. Computer programs known in the art can be used to design primers with the required specificity and optimal amplification properties.

A nucleotide probe may be labeled with a detectable substance such as a radioactive label which provides for an adequate signal and has sufficient half-life such as $^{32}P$, $^{3}H$, $^{14}C$ or the like. Other detectable substances that may be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleic acids to be detected and the amount of nucleic acids available for hybridization. Labeled probes may be hybridized to nucleic acids on solid supports such as nitrocellulose filters or nylon membranes as generally described in Sambrook et al., 1989, Molecular Cloning, A Laboratory Manual (2nd ed.). The nucleic acid probes may be used to detect Polynucleotide Thyroid Cancer Markers, preferably in human cells. The nucleotide probes may also be useful in the diagnosis of thyroid cancer involving Polynucleotide Thyroid Cancer Markers, in monitoring the progression of thyroid cancer, or monitoring a therapeutic treatment.

The detection of polynucleotides in a sample may involve the amplification of specific gene sequences using an amplification method such as PCR, followed by the analysis of the amplified molecules using techniques known to those skilled in the art. By way of example, oligonucleotide primers may be employed in a PCR based assay to amplify a portion of a polynucleotide and to amplify a portion of a polynucleotide derived from a sample, wherein the oligonucleotide primers are specific for (i.e. hybridize to) the polynucleotides. The amplified cDNA is then separated and detected using techniques well known in the art, such as gel electrophoresis.

In order to maximize hybridization under assay conditions, primers and probes employed in the methods of the invention generally have at least about 60%, preferably at least about 75% and more preferably at least about 90% identity to a portion of a Polynucleotide Thyroid Cancer Marker; that is, they are at least 10 nucleotides, and preferably at least 20 nucleotides in length. In an embodiment the primers and probes are at least about 10-40 nucleotides in length. Examples of primers are SEQ ID NOs. 3-6.

Hybridization and amplification reactions may also be conducted under stringent conditions as discussed herein.

Hybridization and amplification techniques described herein may be used to assay qualitative and quantitative aspects of polynucleotide expression. For example, RNA may be isolated from a cell type or tissue known to express Polynucleotide Thyroid Cancer Markers, and tested utilizing the hybridization (e.g. standard Northern analyses) or PCR techniques.

The primers and probes may be used in situ i.e., directly on tissue sections (fixed and/or frozen) of patient tissue obtained from biopsies or resections.

In an aspect of the invention, a method is provided employing reverse transcriptase-polymerase chain reaction (RT-PCR), in which PCR is applied in combination with reverse transcription. Generally, RNA is extracted from a sample tissue using standard techniques and is reverse transcribed to produce cDNA. The cDNA is used as a template for a polymerase chain reaction. The cDNA is hybridized to primer sets which are specifically designed against a Polynucleotide Thyroid Cancer Marker. Once the primer and template have annealed a DNA polymerase is employed to extend from the primer, to synthesize a copy of the template. The DNA strands are denatured, and the procedure is repeated many times until sufficient DNA is generated to allow visualization by ethidium bromide staining and agarose gel electrophoresis.

Amplification may be performed on samples obtained from a subject with suspected thyroid cancer, an individual who is not afflicted with thyroid cancer or has early stage disease or has aggressive or metastatic disease, in particular ATC. The reaction may be performed on several dilutions of cDNA spanning at least two orders of magnitude. A statistically significant difference in expression in several dilutions of the subject sample as compared to the same dilutions of the non-cancerous sample or early-stage cancer sample may be considered positive for the presence of cancer.

Oligonucleotides or longer fragments derived from Polynucleotide Thyroid Cancer Markers may be used as targets in a microarray. The microarray can be used to monitor the expression levels of the polynucleotides and to identify genetic variants, mutations, and polymorphisms. The information from the microarray may be used to determine gene function, to understand the genetic basis of a disorder, to diagnose a disorder, and to develop and monitor the activities of therapeutic agents. Thus, the invention also includes an array comprising Polynucleotide Thyroid Cancer Markers, and optionally other thyroid cancer markers. The array can be used to assay expression of Polynucleotide Thyroid Cancer Markers in the array. The invention allows the quantitation of expression of the polynucleotides.

The invention provides microarrays comprising Polynucleotide Thyroid Cancer Markers. In one embodiment, the invention provides a microarray for distinguishing samples associated with thyroid cancer, in particular aggressive thyroid cancer or thyroid cancer with metastatic potential, in particular ATC, comprising a positionally-addressable array of polynucleotide probes bound to a support, the polynucleotide probes comprising sequences complementary and hybridizable to Polynucleotide Thyroid Cancer Markers.

In an embodiment, the array can be used to monitor the time course of expression of Polynucleotide Thyroid Cancer Markers in the array. This can occur in various biological contexts such as tumor progression.

An array can also be useful for ascertaining differential expression patterns of Polynucleotide Thyroid Cancer Markers, and optionally other thyroid cancer markers in normal and abnormal cells. This may provide a battery of nucleic acids that could serve as molecular targets for diagnosis or therapeutic intervention.

Protein Methods

Binding agents may be used for a variety of diagnostic and assay applications. There are a variety of assay formats known to the skilled artisan for using a binding agent to detect a target molecule in a sample. (For example, see Harlow and Lane, Antibodies: A Laboratory Manual, Cold Spring Harbor Laboratory, NY, 1988). In general, the presence or absence of an aggressive thyroid cancer or a thyroid cancer with metastatic potential, in particular ATC, in a subject may be determined by (a) contacting a sample from the subject with a binding agent; (b) detecting in the sample a level of polypeptide that binds to the binding agent; and (c) comparing the level of polypeptide with a predetermined standard or cut-off value. In particular aspects of the invention, the binding agent is an antibody.

In an aspect, the invention provides a diagnostic method for monitoring or diagnosing thyroid cancer in a subject by quantitating Polypeptide Thyroid Cancer Markers in a biological sample from the subject comprising reacting the sample with antibodies specific for Polypeptide Thyroid Cancer Markers which are directly or indirectly labeled with detectable substances and detecting the detectable substances.

In an aspect of the invention, a method for detecting or diagnosing aggressiveness or metastatic potential of a thyroid cancer, in particular ATC, is provided comprising or consisting essentially of:
(a) obtaining a sample suspected of containing Polypeptide Thyroid Cancer Markers;
(b) contacting said sample with antibodies that specifically bind Polypeptide Thyroid Cancer Markers under conditions effective to bind the antibodies and form complexes;
(c) measuring the amount of Polypeptide Thyroid Cancer Markers present in the sample by quantitating the amount of the complexes; and
(d) comparing the amount of Polypeptide Thyroid Cancer Markers present in the samples with the amount of Polypeptide Thyroid Cancer Markers in a control, wherein a change or significant difference in the amount of Polypeptide Thyroid Cancer Markers in the sample compared with the amount in the control is indicative of aggressive thyroid cancer or a thyroid cancer with metastatic potential, in particular ATC.

In an embodiment, the invention contemplates a method for monitoring the progression of thyroid cancer in an individual, comprising:
(a) contacting antibodies which bind to Polypeptide Thyroid Cancer Markers with a sample from the individual so as to form complexes comprising the antibodies and Polypeptide Thyroid Cancer Markers in the sample;
(b) determining or detecting the presence or amount of complex formation in the sample;
(c) repeating steps (a) and (b) at a point later in time; and
(d) comparing the result of step (b) with the result of step (c), wherein a difference in the amount of complex formation is indicative of disease, disease stage, progression, aggressiveness and/or metastatic potential of the cancer in said individual.

The amount of complexes may also be compared to a value representative of the amount of the complexes from an individual not at risk of, or afflicted with thyroid cancer at a different stage or from the same individual at a different point in time.

Antibodies specifically reactive with Polypeptide Thyroid Cancer Markers or derivatives, such as enzyme conjugates or labeled derivatives, may be used to detect Polypeptide Thyroid Cancer Markers in various samples (e.g. biological materials, in particular tissue samples). They may be used as diagnostic or prognostic reagents and they may be used to detect abnormalities in the level of Polypeptide Thyroid Cancer Markers or abnormalities in the structure, and/or temporal, tissue, cellular, or subcellular location of Polypeptide Thyroid Cancer Markers. Antibodies may also be used to screen potentially therapeutic compounds in vitro to determine their effects on thyroid cancer involving Polypeptide Thyroid Cancer Markers. In vitro immunoassays may also be used to assess or monitor the efficacy of particular therapies.

Antibodies may be used in any immunoassay that relies on the binding interaction between antigenic determinants of Polypeptide Thyroid Cancer Markers and the antibodies. Immunoassay procedures for in vitro detection of antigens in samples are also well known in the art. [See for example, Paterson et al., Int. J. Can. 37:659 (1986) and Burchell et al., Int. J. Can. 34:763 (1984) for a general description of immunoassay procedures]. Qualitative and/or quantitative determinations of Polypeptide Thyroid Cancer Markers in a sample may be accomplished by competitive or non-competitive immunoassay procedures in either a direct or indirect format. Detection of Polypeptide Thyroid Cancer Markers using antibodies can, for example involve immunoassays which are run in either the forward, reverse or simultaneous modes. Examples of immunoassays are radioimmunoassays (RIA), enzyme immunoassays (e.g. ELISA), immunofluorescence, immunoprecipitation, latex agglutination, hemagglutination, histochemical tests, and sandwich (immunometric) assays. Alternatively, the binding of antibodies to Polypeptide Thyroid Cancer Markers can be detected directly using, for example, a surface plasmon resonance (SPR) procedure such as, for example, Biacore®, microcalorimetry or nano-cantilivers. These terms are well understood by those skilled in the art, and they will know, or can readily discern, other immunoassay formats without undue experimentation.

Antibodies specific for Polypeptide Thyroid Cancer Markers may be labelled with a detectable substance and localised in biological samples based upon the presence of the detectable substance. Examples of detectable substances include, but are not limited to, the following: radioisotopes (e.g., $^3$H, $^{14}$C, $^{35}$S, $^{125}$I, $^{131}$I), fluorescent labels, (e.g., FITC, rhodamine, lanthanide phosphors), luminescent labels such as luminol; and enzymatic labels (e.g., horseradish peroxidase, beta-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), and predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

One of the ways an antibody can be detectably labelled is to link it directly to an enzyme. The enzyme when later exposed to its substrate will produce a product that can be detected. Examples of detectable substances that are enzymes are horseradish peroxidase, beta-galactosidase, luciferase, alkaline phosphatase, acetylcholinesterase, malate dehydrogenase, ribonuclease, urease, catalase, glucose-6-phosphate, staphylococcal nuclease, delta-5-steriod isomerase, yeast alcohol dehydrogenase, alpha-glycerophosphate, triose phosphate isomerase, asparaginase, glucose oxidase, and acetylcholine esterase.

For increased sensitivity in an immunoassay system a fluorescence-emitting metal atom such as Eu (europium) and other lanthanides can be used. These can be attached to the desired molecule by means of metal-chelating groups such as DTPA or EDTA.

A bioluminescent compound may also be used as a detectable substance. Examples of bioluminescent detectable substances are luciferin, luciferase and aequorin.

Indirect methods may also be employed in which the primary antigen-antibody reaction is amplified by the introduction of a second antibody, having specificity for the antibody reactive against Polypeptide Thyroid Cancer Markers. By way of example, if the antibody having specificity against Polypeptide Thyroid Cancer Markers is a rabbit IgG antibody, the second antibody may be goat anti-rabbit IgG, Fc fragment specific antibody labeled with a detectable substance as described herein.

Methods for conjugating or labelling the antibodies discussed above may be readily accomplished by one of ordinary skill in the art.

Cytochemical techniques known in the art for localizing antigens using light and electron microscopy may be used to detect Polypeptide Thyroid Cancer Markers. Generally, an antibody may be labeled with a detectable substance and a Polypeptide Thyroid Cancer Marker may be localized in tissues and cells based upon the presence of the detectable substance.

In the context of the methods of the invention, the sample, binding agents (e.g. antibodies), or Polypeptide Thyroid Cancer Markers may be immobilized on a carrier or support, such as, for example, agarose, cellulose, nitrocellulose, dextran, Sephadex, Sepharose, liposomes, carboxymethyl cellulose, polyacrylamides, polystyrene, filter paper, ion-exchange resin, plastic film, nylon or silk. The support material may have any possible configuration including spherical cylindrical or flat. Thus, the carrier may be in the shape of, for example, a tube, test plate, well, beads, disc, sphere, etc. The immobilized material may be prepared by reacting the material with a suitable insoluble carrier using known chemical or physical methods, for example, cyanogen bromide coupling. Binding agents (e.g. antibodies) may be indirectly immobilized using second binding agents specific for the first binding agent. For example, mouse antibodies specific for Polypeptide Thyroid Cancer Markers may be immobilized using sheep anti-mouse IgG Fc fragment specific antibody coated on the carrier or support.

Where a radioactive label is used as a detectable substance, a Polypeptide Thyroid Cancer Marker may be localized by radioautography. The results of radioautography may be quantitated by determining the density of particles in the radioautographs by various optical methods, or by counting the grains.

Time-resolved fluorometry may be used to detect a fluorescent signal, label, or detectable substance. For example, the method described in Christopoulos T K and Diamandis E P Anal. Chem., 1992:64:342-346 may be used with a conventional time-resolved fluorometer.

According to an embodiment of the invention, an immunoassay for detecting Polypeptide Thyroid Cancer Markers in a biological sample comprises contacting an amount of a binding agent that specifically binds to Polypeptide Thyroid Cancer Markers in the sample under conditions that allow the formation of a complex(es) comprising the binding agent and Polypeptide Thyroid Cancer Markers and determining the presence or amount of the complex(es) as a measure of the amount of the Polypeptide Thyroid Cancer Markers contained in the sample.

In accordance with an embodiment of the invention, a method is provided wherein Polypeptide Thyroid Cancer Marker antibodies are directly or indirectly labelled with enzymes, substrates for the enzymes are added wherein the substrates are selected so that the substrates, or a reaction product of an enzyme and substrate, form fluorescent complexes with lanthanide metals, preferably europium and terbium. A lanthanide metal(s) is added and Polypeptide Thyroid Cancer Markers are quantitated in the sample by measuring fluorescence of the fluorescent complexes. Enzymes are selected based on the ability of a substrate of the enzyme, or a reaction product of the enzyme and substrate, to complex with lanthanide metals.

Examples of enzymes and substrates for enzymes that provide such fluorescent complexes are described in U.S. Pat. No. 5,312,922 to Diamandis. By way of example, when the antibody is directly or indirectly labelled with alkaline phosphatase, the substrate employed in the method may be 4-methylumbelliferyl phosphate, 5-fluorosalicyl phosphate, or diflunisal phosphate. The fluorescence intensity of the complexes is typically measured using a time-resolved fluorometer.

Antibodies specific for Polypeptide Thyroid Cancer Markers may also be indirectly labelled with enzymes. For example, an antibody may be conjugated to one partner of a ligand binding pair, and the enzyme may be coupled to the other partner of the ligand binding pair. Representative examples include avidin-biotin, and riboflavin-riboflavin binding protein. In embodiments, antibodies specific for Polypeptide Thyroid Cancer Markers are labelled with enzymes.

Aspects of the methods of the invention involve (a) reacting a biological sample from a subject with antibodies specific for Polypeptide Thyroid Cancer Markers wherein the antibodies are directly or indirectly labelled with enzymes; (b) adding substrates for the enzymes wherein the substrates are selected so that the substrates, or reaction products of the enzymes and substrates form fluorescent complexes; (c) quantitating Polypeptide Thyroid Cancer Markers in the sample by measuring fluorescence of the fluorescent complexes; and (d) comparing the quantitated levels to levels obtained for other samples from the subject patient, or control subjects. In an embodiment, the Polypeptide Thyroid Cancer Markers are Ep-ICD and β-catenin and the quantitated levels are compared to levels quantitated for normal subjects, subjects with an early stage of disease or the same subject at a different point in time, wherein an increase in the levels of the markers compared with the control subjects is indicative of ATC and/ or poor prognosis or survival.

A particular embodiment of the invention comprises the following steps:
(a) incubating a biological sample with a first antibody specific for Polypeptide Thyroid Cancer Markers which is directly or indirectly labeled with a detectable substance, and a second antibody specific for Polypeptide Thyroid Cancer Markers which is immobilized;
(b) separating the first antibody from the second antibody to provide a first antibody phase and a second antibody phase;
(c) detecting the detectable substance in the first or second antibody phase thereby quantitating Polypeptide Thyroid Cancer Markers in the biological sample; and
(d) comparing the quantitated Polypeptide Thyroid Cancer Markers with levels for a predetermined standard.

The standard may correspond to levels quantitated for samples from control subjects with no disease or early stage disease or from other samples of the subject. Increased levels of Ep-ICD and/or β-catenin as compared to the standard may be indicative of anaplastic thyroid carcinoma.

In accordance with an embodiment, the present invention provides means for determining Polypeptide Thyroid Cancer Markers in a sample by measuring Polypeptide Thyroid Cancer Markers by immunoassay. It will be evident to a skilled artisan that a variety of competitive or non-competitive immunoassay methods can be used to measure Polypeptide Thyroid Cancer Markers in serum. Competitive methods typically employ immobilized or immobilizable antibodies to Polypeptide Thyroid Cancer Markers and labeled forms of Polypeptide Thyroid Cancer Markers. Sample Polypeptide Thyroid Cancer Markers and labeled Polypeptide Thyroid Cancer Markers compete for binding to antibodies specific for Polypeptide Thyroid Cancer Markers. After separation of the resulting labeled Polypeptide Thyroid Cancer Markers that have become bound to antibody (bound fraction) from that which has remained unbound (unbound fraction), the amount of the label in either bound or unbound fraction is measured and may be correlated with the amount of Polypeptide Thyroid Cancer Markers in the test sample in any conventional manner, e.g., by comparison to a standard curve.

In another aspect, a non-competitive method is used for the determination of Polypeptide Thyroid Cancer Markers with the most common method being the "sandwich" method. In this assay, two antibodies specific for a Polypeptide Thyroid Cancer Marker are employed. One of the antibodies is directly or indirectly labeled (the "detection antibody"), and the other is immobilized or immobilizable (the "capture antibody"). The capture and detection antibodies can be contacted simultaneously or sequentially with the test sample. Sequential methods can be accomplished by incubating the capture antibody with the sample, and adding the detection antibody at a predetermined time thereafter or the detection antibody can be incubated with the sample first and then the capture antibody added. After the necessary incubation(s) have occurred, to complete the assay, the capture antibody may be separated from the liquid test mixture, and the label may be measured in at least a portion of the separated capture antibody phase or the remainder of the liquid test mixture. Generally it is measured in the capture antibody phase since it comprises Polypeptide Thyroid Cancer Marker "sandwiched" between the capture and detection antibodies. In another embodiment, the label may be measured without separating the capture antibody and liquid test mixture.

In particular sandwich immunoassays of the invention mouse polyclonal/monoclonal antibodies specific for Polypeptide Thyroid Cancer Markers and rabbit polyclonal/monoclonal antibodies specific for Polypeptide Thyroid Cancer Markers are utilized.

In a typical two-site immunometric assay for Polypeptide Thyroid Cancer Markers one or both of the capture and detection antibodies are polyclonal antibodies or one or both of the capture and detection antibodies are monoclonal antibodies (i.e. polyclonal/polyclonal, monoclonal/monoclonal, or monoclonal/polyclonal). The label used in the detection antibody can be selected from any of those known conventionally in the art. The label may be an enzyme or a chemiluminescent moiety, but it can also be a radioactive isotope, a fluorophor, a detectable ligand (e.g., detectable by a secondary binding by a labeled binding partner for the ligand), and the like. In an aspect, the antibody is labelled with an enzyme which is detected by adding a substrate that is selected so that a reaction product of the enzyme and substrate forms fluorescent complexes. The capture antibody may be selected so that it provides a means for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay. An immobilized capture antibody may comprise an antibody covalently or noncovalently attached to a solid phase such as a magnetic particle, a latex particle, a microtiter plate well, a bead, a cuvette, or other reaction vessel. An example of an immobilizable capture antibody is antibody which has been chemically modified with a ligand moiety, e.g., a hapten, biotin, or the like, and which can be subsequently immobilized by contact with an immobilized form of a binding partner for the ligand, e.g., an antibody, avidin, or the like. In an embodiment, the capture antibody may be immobilized using a species specific antibody for the capture antibody that is bound to the solid phase.

Screening Methods

The invention also contemplates methods for evaluating test agents or compounds for their potential efficacy in treating thyroid cancer, in particular aggressive thyroid cancer, more particularly ATC. Test agents and compounds include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], polynucleotides (e.g. antisense, siRNA), and small organic or inorganic molecules. The agents or compounds may be endogenous physiological compounds or natural or synthetic compounds.

The invention provides a method for assessing a test agent for potential efficacy in treating thyroid cancer, in particular aggressive thyroid cancer, more particularly ATC, the method comprising comparing:
(a) levels of one or more Thyroid Cancer Markers, and optionally other markers in a first sample obtained from a patient and exposed to the test agent; and
(b) levels of one or more Thyroid Cancer Markers, and optionally other markers, in a second sample obtained from the patient, wherein the sample is not exposed to the test agent, wherein a significant difference in the levels of expression of one or more Thyroid Cancer Markers, and optionally the other markers, in the first sample, relative to the second sample, is an indication that the test agent is potentially efficacious for treating thyroid cancer in the patient.

The first and second samples may be portions of a single sample obtained from a patient or portions of pooled samples obtained from a patient.

In an aspect, the invention provides a method of selecting an agent for treating thyroid cancer, in particular aggressive thyroid cancer, more particularly ATC, in a patient comprising:
- (a) obtaining a sample from the patient;
- (b) separately maintaining aliquots of the sample in the presence of a plurality of test agents;
- (c) comparing one or more Thyroid Cancer Markers, and optionally other markers, in each of the aliquots; and
- (d) selecting one of the test agents which alters the levels of one or more Thyroid Cancer Markers, and optionally other markers in the aliquot containing that test agent, relative to other test agents.

In an aspect, the invention provides a method of selecting an agent for inhibiting thyroid cancer in a subject the method comprising (a) obtaining a sample comprising cancer cells from the subject; (b) separately exposing aliquots of the sample in the presence of a plurality of test agents; (c) comparing levels of one or more Thyroid Cancer Markers in each of the aliquots; and (d) selecting one of the test agents which alters the levels of Thyroid Cancer Markers in the aliquot containing that test agent, relative to other test agents, wherein the thyroid cancer markers are Ep-ICD and/or β-catenin. This method may further comprise administering to a subject at least one of the test agents which alters the levels of Thyroid Cancer Markers in the aliquot containing that test agent, relative to other test agents.

In an aspect the invention provides a method of assessing the thyroid cancer cell carcinogenic potential of a test compound, the method comprising: (a) maintaining separate aliquots of thyroid cancer cells in the presence and absence of the test compound; and (b) comparing expression of one or more Thyroid Cancer Markers, in each of the aliquots, and wherein a significant difference in levels of Thyroid Cancer Markers in the aliquot maintained in the presence of the test compound, relative to the aliquot maintained in the absence of the test compound, is an indication that the test compound possesses thyroid cancer cell carcinogenic potential, wherein the Thyroid Cancer Markers are Ep-ICD and/or β-catenin.

Kits

The invention contemplates kits for carrying out the methods of the invention to diagnose thyroid cancer, and in particular to detect the aggressiveness or metastatic potential of a thyroid cancer, more particularly ATC. Such kits typically comprise two or more components required for performing a diagnostic assay. Components include but are not limited to compounds, reagents, containers, and/or equipment. Accordingly, the methods described herein may be performed by utilizing pre-packaged diagnostic kits comprising at least agents (e.g. antibodies, probes, primers, etc.) described herein, which may be conveniently used, e.g., in clinical settings to diagnose patients afflicted with thyroid cancer, or exhibiting a predisposition to developing thyroid cancer and in particular to determine the aggressiveness or metastatic potential of a thyroid cancer, more particularly ATC.

The invention contemplates a container with a kit comprising a binding agent(s) as described herein for diagnosing thyroid cancer, in particular determining the aggressiveness or metastatic potential of a thyroid cancer, more particularly ATC. By way of example, the kit may contain antibodies specific for Polypeptide Thyroid Cancer Markers, antibodies against the antibodies labelled with an enzyme(s), and a substrate for the enzyme(s). The kit may also contain microtiter plate wells, standards, assay diluent, wash buffer, adhesive plate covers, and/or instructions for carrying out a method of the invention using the kit.

In an aspect, the invention provides a test kit for diagnosing thyroid cancer in a subject, in particular the aggressiveness or metastatic potential of a thyroid cancer, more particularly ATC, which comprises an antibody that binds to Polypeptide Thyroid Cancer Markers and/or polynucleotides that hybridize to or amplify Polynucleotide Thyroid Cancer Markers. In another aspect the invention relates to use of an antibody that binds to a Polypeptide Thyroid Cancer Marker and/or a polynucleotide that hybridize to or amplifies a Polynucleotide Thyroid Cancer Marker, in the manufacture of a composition for diagnosing or detecting a thyroid cancer, in particular diagnosing or detecting the aggressiveness or metastatic potential of a thyroid cancer.

In a further aspect of the invention, the kit includes antibodies or antibody fragments which bind specifically to epitopes of Polypeptide Thyroid Cancer Markers and means for detecting binding of the antibodies to their epitopes associated with thyroid cancer cells, either as concentrates (including lyophilized compositions), which may be further diluted prior to testing. In particular, the invention provides a kit for diagnosing the aggressiveness or metastatic potential of a thyroid cancer, in particular ATC, comprising a known amount of a first binding agent that specifically binds to a Polypeptide Thyroid Cancer Marker wherein the first binding agent comprises a detectable substance, or it binds directly or indirectly to a detectable substance.

A kit may be designed to detect the levels of Polynucleotide Thyroid Cancer Markers in a sample. Such kits generally comprise oligonucleotide probes or primers, as described herein, which hybridize to or amplify Polynucleotide Thyroid Cancer Markers. Oligonucleotides may be used, for example, within PCR or hybridization procedures. Test kits useful for detecting target Polynucleotide Thyroid Cancer Markers are also provided which comprise a container containing a Polynucleotide Thyroid Cancer Marker, and fragments or complements thereof. A kit can comprise one or more of the primers of SEQ ID NOs. 3 to 6.

The kits of the invention can further comprise containers with tools useful for collecting test samples (e.g. serum) including lancets and absorbent paper or cloth for collecting and stabilizing blood.

Computer Systems

Analytic methods contemplated herein can be implemented by use of computer systems and methods described below and known in the art. Thus, the invention provides computer readable media comprising one or more Thyroid Cancer Markers. "Computer readable media" refers to any medium that can be read and accessed directly by a computer, including but not limited to magnetic storage media, such as floppy discs, hard disc storage medium, and magnetic tape; optical storage media such as CD-ROM; electrical storage media such as RAM and ROM; and hybrids of these categories such as magnetic/optical storage media. Thus, the invention contemplates computer readable medium having recorded thereon markers identified for patients and controls.

"Recorded" refers to a process for storing information on computer readable medium. The skilled artisan can readily adopt any of the presently known methods for recording information on computer readable medium to generate manufactures comprising information on one or more markers disclosed herein.

A variety of data processor programs and formats can be used to store information on one or more Thyroid Cancer Markers. For example, the information can be represented in a word processing text file, formatted in commercially-available software such as WordPerfect and MicroSoft Word, or represented in the form of an ASCII file, stored in a database application, such as DB2, Sybase, Oracle, or the like. Any number of dataprocessor structuring formats (e.g., text file or database) may be adapted in order to obtain computer readable medium having recorded thereon the marker information.

By providing the marker information in computer readable form, one can routinely access the information for a variety of purposes. For example, one skilled in the art can use the information in computer readable form to compare marker information obtained during or following therapy with the information stored within the data storage means.

The invention provides a medium for holding instructions for performing a method for determining whether a patient has thyroid cancer, in particular aggressive thyroid cancer, more particularly ATC, or a pre-disposition to such condition, comprising determining the presence or absence of one or more Thyroid Cancer Markers, and based on the presence or absence of the markers, determining the condition or a pre-disposition to the condition, optionally recommending a procedure or treatment.

The invention also provides in an electronic system and/or in a network, a method for determining whether a subject has a condition disclosed herein, or a pre-disposition to a condition disclosed herein, comprising determining the presence or absence of one or more markers, and based on the presence or absence of the markers, determining whether the subject has the condition or a pre-disposition to the condition, and optionally recommending a procedure or treatment.

The invention further provides in a network, a method for determining whether a subject has a condition disclosed herein or a pre-disposition to a condition disclosed herein comprising: (a) receiving phenotypic information on the subject and information on one or more markers disclosed herein associated with samples from the subject; (b) acquiring information from the network corresponding to the markers; and (c) based on the phenotypic information and information on the markers, determining whether the subject has the condition or a pre-disposition to the condition, and (d) optionally recommending a procedure or treatment.

The invention still further provides a system for identifying selected records that identify a diseased cell or tissue. A system of the invention generally comprises a digital computer; a database server coupled to the computer; a database coupled to the database server having data stored therein, the data comprising records of data comprising one or more markers disclosed herein, and a code mechanism for applying queries based upon a desired selection criteria to the data file in the database to produce reports of records which match the desired selection criteria.

The invention contemplates a business method for determining whether a subject has a condition disclosed herein or a pre-disposition to a condition disclosed herein, in particular ATC, comprising: (a) receiving phenotypic information on the subject and information on one or more markers disclosed herein associated with samples from the subject; (b) acquiring information from a network corresponding to the markers; and (c) based on the phenotypic information, information on the markers and acquired information, determining whether the subject has the condition or a pre-disposition to the condition, and optionally recommending a procedure or treatment.

In an aspect of the invention, the computer systems, components, and methods described herein are used to monitor a condition or determine the stage of a condition.

Therapeutic Applications

The invention contemplates therapeutic applications associated with the Thyroid Cancer Markers disclosed herein including thyroid cancer, in particular aggressive thyroid cancer, more particularly ATC. Thyroid Cancer Markers may be a target for therapy. For example, nuclear Ep-ICD can be a target for treatment of aggressive thyroid cancers and ATC. Therapeutic methods include immunotherapeutic methods including the use of antibody therapy. In one aspect, the invention provides one or more antibodies that may be used to prevent thyroid cancer, in particular aggressive thyroid cancer, more particularly ATC. In another aspect, the invention provides a method of preventing, inhibiting or reducing thyroid cancer, in particular aggressive thyroid cancer, more particularly ATC, comprising administering to a patient an antibody which binds to a Thyroid Cancer Marker (e.g. Ep-ICD), in an amount effective to prevent, inhibit, or reduce the condition or the onset of the condition.

An antibody which binds to a Thyroid Cancer Marker, in particular Ep-ICD, may be in combination with a label, drug or cytotoxic agent, a target-binding region of a receptor, an adhesion molecule, a ligand, an enzyme, a cytokine, or a chemokine. In aspects of the invention, the Thyroid Cancer Marker, in particular Ep-ICD, may be conjugated to cytotoxic agents (e.g., chemotherapeutic agents) or toxins or active fragments thereof. Examples of toxins and corresponding fragments thereof include diphtheria A chain, exotoxin A chain, ricin A chain, abrin A chain, curcin, crotin, phenomycin, enomycin and the like. A cytotoxic agent may be a radiochemical prepared by conjugating radioisotopes to antibodies, or binding of a radionuclide to a chelating agent that has been covalently attached to the antibody. An antibody may also be conjugated to one or more small molecule toxins, such as a calicheamicin, a maytansine, a trichothene, and CC1065 (see U.S. Pat. No. 5,208,020).

The methods of the invention contemplate the administration of single antibodies as well as combinations, or "cocktails", of different individual antibodies such as those recognizing different epitopes of other markers. Such cocktails may have certain advantages inasmuch as they contain antibodies that bind to different epitopes of Thyroid Cancer Markers and/or exploit different effector mechanisms. Such antibodies in combination may exhibit synergistic therapeutic effects. In addition, the administration of one or more marker specific antibodies may be combined with other therapeutic agents. The specific antibodies may be administered in their "naked" or unconjugated form, or may have therapeutic agents conjugated to them.

The invention also contemplates a method of treating thyroid cancer in a subject, comprising delivering to the subject in need thereof, an antibody specific for Ep-CAM, in particular EpEx or Ep-ICD. In an aspect of the invention, the antibody is conjugated to a cytotoxic agent or toxin (see above). The antibody may be a therapeutic antibody disclosed for example in U.S. Pat. Nos. 7,557,190 and 7,459,538, US Published Application Nos. 20050163785 and 20070122406, and 20070196366 and McDonald et al. (Drug Design, Development and Therapy 2008; 2:105-114). In a particular embodiment, the antibody is an antibody conjugated to a toxin, more particularly VB4-845 immunotoxin (Viventia Biotechnologies Inc., Ontario, Canada).

More particularly, and according to one aspect of the invention, there is provided a method of treating a subject having thyroid cancer wherein an antibody specific for Ep-CAM, in particular EpEx or Ep-ICD, is administered in a therapeutically effective amount. In a further aspect, the antibody is provided in a pharmaceutically acceptable form.

In an aspect, the invention provides a pharmaceutical composition for the treatment of thyroid cancer characterized in that the composition comprises an antibody specific for Ep-CAM, in particular EpEx or Ep-ICD, together with a pharmaceutically acceptable carrier, excipient or vehicle.

Antibodies used in the methods of the invention may be formulated into pharmaceutical compositions comprising a carrier suitable for the desired delivery method. Suitable carriers include any material which when combined with the antibodies retains the function of the antibody and is non-reactive with the subject's immune systems. Examples include any of a number of standard pharmaceutical carriers such as sterile phosphate buffered saline solutions, bacteriostatic water, and the like (see, generally, Remington's Pharmaceutical Sciences 16th Edition, A. Osal., Ed., 1980).

One or more marker specific antibody formulations may be administered via any route capable of delivering the antibodies to the site or injury. Routes of administration include, but are not limited to, intravenous, intraperitoneal, intramuscular, intradermal, and the like. Antibody preparations may be lyophilized and stored as a sterile powder, preferably under vacuum, and then reconstituted in bacteriostatic water containing, for example, benzyl alcohol preservative, or in sterile water prior to injection.

Treatment will generally involve the repeated administration of the antibody preparation via an acceptable route of administration at an effective dose. Dosages will depend upon various factors generally appreciated by those of skill in the art, including the etiology of the condition, stage of the condition, the binding affinity and half-life of the antibodies used, the degree of marker expression in the patient, the desired steady-state antibody concentration level, frequency of treatment, and the influence of any therapeutic agents used in combination with a treatment method of the invention. A determining factor in defining the appropriate dose is the amount of a particular antibody necessary to be therapeutically effective in a particular context. Repeated administrations may be required to achieve a desired effect. Direct administration of one or more marker antibodies is also possible and may have advantages in certain situations.

Patients may be evaluated for Thyroid Cancer Markers in order to assist in the determination of the most effective dosing regimen and related factors. The assay methods described herein, or similar assays, may be used for quantitating marker levels in patients prior to treatment. Such assays may also be used for monitoring throughout therapy, and may be useful to gauge therapeutic success in combination with evaluating other parameters such as levels of markers.

Polynucleotide Thyroid Cancer Markers disclosed herein can be turned off by transfecting a cell or tissue with vectors that express high levels of the polynucleotides. Such constructs can inundate cells with untranslatable sense or antisense sequences. Even in the absence of integration into the DNA, such vectors may continue to transcribe RNA molecules until all copies are disabled by endogenous nucleases. Vectors derived from retroviruses, adenovirus, herpes or vaccinia viruses, or from various bacterial plasmids, may be used to deliver polynucleotides to a targeted organ, tissue, or cell population. Methods well known to those skilled in the art may be used to construct recombinant vectors that will express polynucleotides such as antisense. (See, for example, the techniques described in Sambrook et al (supra) and Ausubel et al (supra).)

Methods for introducing vectors into cells or tissues which are suitable for in vivo, in vitro and ex vivo therapy are well known in the art. For example, delivery by transfection, or by liposome are well known in the art.

Modifications of gene expression can be obtained by designing antisense molecules, DNA, RNA or PNA, to the regulatory regions of a Polynucleotide Thyroid Cancer Marker, i.e., the promoters, enhancers, and introns. Preferably, oligonucleotides are derived from the transcription initiation site, e.g. between −10 and +10 regions of the leader sequence. The antisense molecules may also be designed so that they block translation of mRNA by preventing the transcript from binding to ribosomes Inhibition may also be achieved using "triple helix" base-pairing methodology. Triple helix pairing compromises the ability of the double helix to open sufficiently for the binding of polymerases, transcription factors, or regulatory molecules. Therapeutic advances using triplex DNA are reviewed by Gee J E et al (In: Huber B E and B I Carr (1994) Molecular and Immunologic Approaches, Futura Publishing Co, Mt Kisco N.Y.).

Ribozymes are enzymatic RNA molecules that catalyze the specific cleavage of RNA. Ribozymes act by sequence-specific hybridization of the ribozyme molecule to complementary target RNA, followed by endonucleolytic cleavage. The invention therefore contemplates engineered hammerhead motif ribozyme molecules that can specifically and efficiently catalyze endonucleolytic cleavage of a polynucleotide marker.

Specific ribozyme cleavage sites within any potential RNA target may initially be identified by scanning the target molecule for ribozyme cleavage sites which include the following sequences, GUA, GUU and GUC. Once the sites are identified, short RNA sequences of between 15 and 20 ribonucleotides corresponding to the region of the target gene containing the cleavage site may be evaluated for secondary structural features which may render the oligonucleotide inoperable. The suitability of candidate targets may also be determined by testing accessibility to hybridization with complementary oligonucleotides using ribonuclease protection assays.

The invention provides a method of preventing, inhibiting, or reducing thyroid cancer, in particular aggressive thyroid cancer, more particularly ATC, in a patient comprising:
  (a) obtaining a tumor sample from the patient;
  (b) separately maintaining aliquots of the sample in the presence of a plurality of test agents;
  (c) comparing levels of Thyroid Cancer Markers and optionally one or more other markers disclosed herein, in each aliquot;
  (d) administering to the patient at least one test agent which alters the levels of Thyroid Cancer Markers and optionally other markers in the aliquot containing that test agent, relative to the other test agents.

An active therapeutic substance described herein may be administered in a convenient manner such as by injection (subcutaneous, intravenous, etc.), oral administration, inhalation, transdermal application, or rectal administration. Depending on the route of administration, the active substance may be coated in a material to protect the substance from the action of enzymes, acids and other natural conditions that may inactivate the substance. Solutions of an active compound as a free base or pharmaceutically acceptable salt can be prepared in an appropriate solvent with a suitable surfactant. Dispersions may be prepared in glycerol, liquid polyethylene glycols, and mixtures thereof, or in oils.

A composition described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in *Remington: The Science and Practice of Pharmacy* (21$^{st}$ Edition. 2005, University of the Sciences in Philadelphia (Editor), Mack Publishing Company), and in The United States Pharmacopeia: The National Formulary (USP 24 NF19) published in 1999. On this basis, the compositions include, albeit not exclusively, solutions of the active substances in association with one or more pharmaceutically acceptable vehicles or diluents, and contained in buffered solutions with a suitable pH and iso-osmotic with the physiological fluids.

A composition is indicated as a therapeutic agent either alone or in conjunction with other therapeutic agents or other forms of treatment. The compositions of the invention may be administered concurrently, separately, or sequentially with other therapeutic agents or therapies.

The therapeutic activity of compositions and agents/compounds identified using a method of the invention and may be evaluated in vivo using a suitable animal model.

The following non-limiting examples are illustrative of the present invention:

Example 1

EpEx and Ep-ICD protein expression in primary human thyroid cancers as well as in a panel of aggressive and non-aggressive thyroid cancer cell lines and by immunohistochemistry (IHC) using antibodies directed against Ep-Ex and Ep-ICD domains of EpCAM were investigated and the findings confirmed by western blotting. To determine if EpCAM overexpression is attributed to increased transcription quantitative real time PCR (Q-PCR) was used for analysis of EpCAM transcripts in these tumors. Further, concurrent staining for nuclear Ep-ICD and β-catenin was carried out to establish the prognostic value of oncogenic Ep-ICD signaling in thyroid cancer.

The following materials and methods were employed in the Study described in this Example.

Materials and Methods

Patients and Tissue Specimens:

The study was approved by Ontario Ethics Committee and Mount Sinai Hospital, Toronto, Canada. All patients were informed and signed consent was obtained. Thirty thyroid carcinoma paraffin blocks were retrieved from the archives of the Department of Pathology, Mount Sinai Hospital, Toronto, Canada. Thirty fresh frozen samples comprising of 15 thyroid tumors and 15 adjacent normal tissues were also included in the study for quantitative real time PCR analysis. The tissues were flash frozen in RNAlater TissueProtect solution (Qiagen, Mississauga, ON) and stored at −80° C. till use. Each case was reviewed by the pathologist prior to further experiments.

The patient follow up data were retrieved from a data bank to correlate the protein expression in tumors with clinical outcome to evaluate the prognostic relevance of these proteins. The patients were followed up for a minimum period of 15 months and a maximum period of 199 months.

Antibodies

Anti-EpCAM monoclonal antibody MOC-31 (AbD Serotec, Oxford, UK) recognizes an extracellular component (EGF1 domain—aa 27-59) in the amino-terminal region of EpCAM [Chaudry Ma et al., 2007]. Intracellular domain of EpCAM, α-EpICD antibody 1144 (Epitomics) recognizes the cytoplasmic domain of EpCAM. β-catenin antibody raised against aa 571-781 of β-catenin (Cat.#610154, B D Sciences, San Jose, Calif.) and c-myc antibody (C19, sc-788, affinity purified rabbit polyclonal antibody, Santa Cruz Biotechnology Inc.).

Cell Lines

The colon cancer cell line WRO (previously considered a thyroid cancer cell line) from M. Ringel, The Ohio State University, Ohio) and ARO—colon cancer cell line (previously considered as ATC cell line) were grown in RPMI 1640 supplemented with 10% fetal bovine serum (FBS), 2 mmol/L L-glutamine, 1 mmol/L sodium pyruvate and 1× non-essential amino acids. TPC-1, a well differentiated papillary thyroid carcinoma cell line, was maintained in Dulbecco's modified Eagle medium (DMEM) supplemented with 5% FBS and 2 mmol/L L-glutamine. The medullary thyroid cancer cell line, TT, (from J. Fagin, University of Cincinnati, Cincinnati, Ohio) was grown in F-12K medium (Invitrogen Life Technologies, Grand Island, N.Y.) supplemented with 10% FBS. The anaplastic thyroid cancer cell line, CAL62 (from J. Fagin) was grown in DMEM supplemented with 10% FBS. All cell lines were cultured in a humidified, 5% $CO_2$ incubator at 37° C.; 70-80% confluent cells were used for the experiments described below.

Immunohistochemistry for EpEx and Ep-ICD Expression in Thyroid Cancers

Serial sections in 4 μm thickness were cut from the paraffin blocks and mounted on glass slides. The sections were deparaffined and hydrated through xylene and graded alcohol series. The slides were treated with 0.3% $H_2O_2$ at room temperature for 30 minutes to block the endogenous peroxidase activity. After blocking non-specific binding with normal horse or goat serum, the sections were incubated with anti-EpEx mouse monoclonal antibody MOC-31 (dilution 1:200), or α-EpICD antibody 1144 (dilution 1:200), or mouse monoclonal β-catenin antibody (dilution 1:200) for 30 minutes and biotinylated secondary antibody (horse anti-mouse or goat anti-rabbit) for 30 minutes. The sections were finally incubated with VECTASTAIN Elite ABC Reagent (Vector labs, Burlingame, Calif.) and diaminobenzedine was used as the chromogen.

Evaluation of Immunohistochemical Staining.

Immunopositive staining was evaluated in five areas of the tissue sections as described [Ralhan et al., 2008]. Sections were scored as positive if epithelial cells showed immunopositivity in the cytoplasm, plasma membrane, and/or nucleus when observed by two evaluators who were blinded to the clinical outcome. These sections were scored as follows: 0, <10% cells; 1, 10-30% cells; 2, 30-50% cells; 3, 50-70% cells; and 4, >70% cells showed immunoreactivity. Sections were also scored semi-quantitatively on the basis of intensity as follows: 0, none; 1, mild; 2, moderate; and 3, intense. Finally, a total score (ranging from 0 to 7) was obtained by adding the scores of percentage positivity and intensity for each of the thyroid cancer and normal thyroid tissue sections. The immunohistochemical data were subjected to statistical analysis as described previously [Ralhan et al., 2008].

The immunohistochemical scoring data were verified using the Visiopharm Integrator System (Visiopharm, Horsholm, Denmark). Only the nuclear staining was quantitated, as the software did not permit simultaneous quantitation of membranous, cytoplasmic and nuclear staining based on differences in intensity of positive brown staining.

Statistical Analysis

The immunohistochemical data were subjected to statistical analysis using SPSS 10.0 software (Chicago). Box plots were used to determine the distribution of total score of membranous EpEx, nuclear Ep-ICD and nuclear or cytoplasmic β-catenin expression in normal thyroid tissues and thyroid cancers. A cut-off= or >2 was defined as positive criterion for nuclear β-catenin immunopositivity for statistical examination. For membranous β-catenin, score of 6 was defined as loss of expression.

The correlation between expression of EpEx, Ep-ICD and/or β-catenin staining with overall patient survival was evaluated using life tables constructed from survival data with Kaplan-Meier plots.

RNA Isolation from Cell Lines, Frozen Specimens, Paraffin Sections and First Strand cDNA Synthesis All RNA isolations were performed according to the manufacturer's instructions. Total RNA were extracted from cell lines using RNeasy Mini Kit (Qiagen, Maryland, Mass.). High Pure RNA Tissue Kit and High Pure RNA Paraffin Kit (Roche, Mannheim, Germany) were used to isolate RNA from fresh frozen thyroid tissue specimens and FFPE samples, respectively. The quantity of RNA was measured using ND-1000 spectrophotometer (Nanodrop Technologies, Wilmington, Del.). First strand cDNA synthesis was performed using Transcriptor First Strand cDNA Synthesis Kit (Roche, Mannheim, Germany). Five p. 1 of the reaction product was used as a template for real-time PCR.

Quantitative Real-Time RT-PCR

Quantitative Real-time RT-PCR (Q-PCR) analyses were performed using LightCycler480 (Roche, Mannheim, Germany) with SYBR Green I Master kit (Roche, Mannheim, Germany) according to manufacturer's instructions. The real-time PCR reaction initiated with incubation at 95° C. for 5 min, followed by 45 cycles of denaturation at 95° C. for 10 sec, annealing at 65° C. for 15 sec, and extension at 72° C. for 15 sec. The melting curve analyses were performed immediately after the completion of the PCR. All reactions were performed in triplicate and the experiments were repeated at least twice. The data were analyzed using LightCycler480 software1.5.

The primers for EpCAM and GAPDH were designed using ProbeFinder assay design software (Roche, Mannheim, Germany), were synthesized and HPLC purified by Sigma. Primer sequences were as follows: EpCAM, 5'-CCATGT-GCTGGTGTGTGAA-3' [SEQ ID NO. 3] (forward) and 5'-TGTGTTTTAGTTCAATGGATGATCCA-3' [SEQ ID NO. 4] (reverse); GAPDH, 5'-AGCCACATCGCTCAGA-CAC-3' [SEQ ID NO. 5] (forward) and 5'-GCCCAATAC-GACCAAATCC-3' [SEQ ID NO. 6] (reverse).

Immunocytochemistry

The aggressive and non-aggressive thyroid carcinoma cells (WRO, CAL-62, TT and TPC-1) and control cells (ARO) were plated (1×103) on cover slips and grown overnight. Thereafter, the cells were washed with PBS thrice and fixed using 4% paraformaldehyde. For Ep-Ex, Ep-ICD and β-catenin detection by immunocytochemistry, fixed cells were stained with MOC-31, 1144 (dilution 1:200) or mouse monoclonal β-catenin antibody respectively for 30 minutes and biotinylated secondary antibody for 30 minutes. The sections were finally incubated with VECTASTAIN Elite ABC Reagent (Vector labs, Burlingame, Calif.) and diaminobenzedine was used as the chromogen.

For immunofluorescence detection, goat anti-mouse IgG-FITC (Sigma, St Louis, Mo.) or IgG-Alexa were used as the secondary antibodies. Nuclei were stained with DAPI. Immunofluorescence was detected using a fluorescent microscope (Leica DM IRBE, Houston, Tex.).

Western Blotting

Cell lysates were prepared in lysis buffer (0.15 mM NaCl, 5 mM EDTA (pH 8.0), 1% Triton, 10 mM Tris-Cl (pH 7.4)), and protease inhibitors cocktail (Roche Diagnostics, Indianapolis, Ind.). The cell lysates (30 micrograms protein) were resolved by SDS-PAGE and transferred to a PVDF membrane (Millipore, Billerica, Mass.). The membrane was probed with the anti-EpCAM mouse monoclonal antibody B302 (Santa Cruz Biotechnology, Santa Cruz, Calif.) (dilution 1:500), followed by a horseradish peroxidase-conjugated secondary goat anti-mouse antibody and chemiluminescence detection system according to the manufacturer's instructions (Perki-nElmer Life Sciences, Boston, Mass.). As a control for protein loading, blots were probed for β-Actin, using a mouse monoclonal antibody, C-4 (Santa Cruz Biotechnology, Santa Cruz, Calif.) (dilution 1:1000). Quantitation was performed by densitometry analysis using ImageGauge software (Altura Software Inc.).

Results

Immunohistochemical Analysis of EpEx and Ep-ICD Expression in Thyroid Cancers

To determine the clinical significance of Ep-Ex and Ep-ICD in thyroid cancers, their expressions were analyzed in archived tissues by immunohistochemistry using domain specific antibodies MOC-31 and 1144 respectively. No plasma membrane EpEx immunoreactivity was observed in ATC (FIG. 1, panel IA). To determine if the loss of membranous EpEx resulted in its cytoplasmic/nuclear accumulation, Ep-ICD immunostaining was carried out using 1144 antibody—intense nuclear and cytoplasmic Ep-ICD immunostaining was observed in ATC (FIG. 1, panel IIA). The activated Ep-ICD has been shown to bind to β-catenin and activate cell proliferation in cancer cells in vitro [Maetzel et al., 2009]. β-catenin immunostaining was carried out in serial sections to determine if there was any correlation between cytoplasmic/nuclear Ep-ICD and nuclear/cytoplasmic β-catenin. The study showed concurrent cytoplasmic and nuclear β-catenin immunostaining in ATCs (FIG. 1, panel IIIA).

In comparison, a subset of the poorly differentiated follicular thyroid cancers (PDFTC) showed intense focal EpEx membrane staining localized to the regions of cell-cell contacts (FIG. 1, panel IB); moderate nuclear staining and cytoplasmic Ep-ICD immunostaining was observed in these tumors (FIG. 1, panel IIB); and mild cytoplasmic staining and predominant membrane staining was observed for β-catenin (FIG. 1, panel IIIB) The poorly differentiated papillary thyroid cancers (PDPTC) showed EpEx membrane staining (FIG. 1, panel IC); no nuclear staining and faint cytoplasmic Ep-ICD immunostaining was observed in these tumors (FIG. 1, panel IIC); membrane and mild cytoplasmic staining was observed for β-catenin (FIG. 1, panel IIIC). The well differentiated papillary thyroid cancer (WDPTC) showed intense EpEx membrane staining (FIG. 1, panel ID); no nuclear staining but mild cytoplasmic Ep-ICD immunostaining was observed in these tumors (FIG. 1, panel IID); and intense membrane staining was observed for β-catenin (FIG. 1, panel IIID) In comparison the normal (non-malignant) thyroid tissues showed basal EpEx membrane immunoreactivity (FIG. 1, panel IE) and faint or no cytoplasmic or nuclear Ep-ICD staining (FIG. 1, panel IIE) and basal membrane immunoreactivity for β-catenin (FIG. 1, panel IIIE) The squamous cell carcinoma variant showed faint EpEx membrane immunoreactivity (FIG. 1, panel IF); intense cytoplasmic and nuclear Ep-ICD staining (FIG. 1, panel IIF); and membranous and cytoplasmic immunoreactivity for β-catenin (FIG. 1, panel IIIF).

The nuclear Ep-ICD staining was quantified using visioform; the histogram showing percentage nuclear Ep-ICD positivity in different subtypes of thyroid cancers is given in FIG. 1G. All the five ATCs showed nuclear positivity; the total nuclear Ep-ICD positive area ranged from 12-40%. Notably, one PDPTC and one PDFTC also showed nuclear Ep-ICD positivity. Overall, analysis of β-catenin expression in different subtypes of thyroid tumors showed cytoplasmic and nuclear expression in ATCs, while membrane localization was observed in PDFTC and PDPTC and in WDPTC as well as in the non-malignant thyroid tissues.

Figure 2:
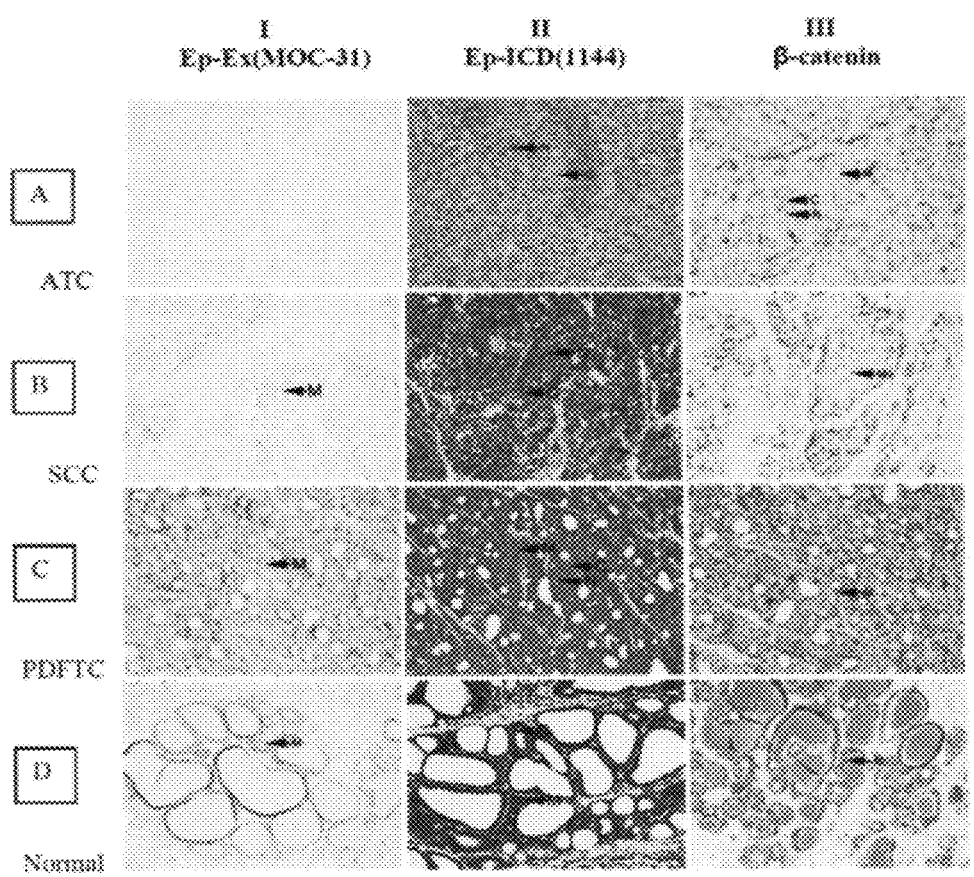
FIG. 2. Immunohistochemical analysis of EpEx, Ep-ICD and β-catenin in the same thyroid cancer patient. No membranous EpEx staining was observed in the anaplastic thyroid cancer section (IA), faint membranous EpEx staining in squamous cell section (IB), strong membranous EpEx staining in both poorly differentiated section and normal section (IC, ID). Nuclear and cytoplasmic Ep-ICD staining in undifferentiated and poorly differentiated sections (IIA-IIC), membranous and cytoplasmic staining in normal tissue (IID). Nuclear and cytoplasmic β catenin staining in anaplastic thyroid cancer section (IIIA), membranous β-catenin staining in the other subsets of this specimen (IIIB-IIID).

Analysis of tissue sections from different tissue blocks of the same patient with different pathology demonstrated differences in expression patterns of these proteins as were observed in individual thyroid tumors. FIG. 2 panel AI depicts an ATC section showing no EpEx membrane staining, while the panel AII shows intense nuclear and cytoplasmic localization of Ep-ICD in serial ATC section and panel AIII shows nuclear and cytoplasmic β-catenin expression. Another tissue block from the same patient showed SCC and Panel BI shows focal faint membrane EpCAM expression, while Panel BII shows intense nuclear and cytoplasmic Ep-ICD expression and Panel BIII shows nuclear and membranous β-catenin expression. In comparison another tissue block from the same patient showing PDFTC demonstrated only membranous EpEx (Panel CI), while only cytoplasmic Ep-ICD was observed (Panel CII) and membranous β-catenin with no nuclear immunostaining was observed (Panel CIII). The normal thyroid tissue from the same patient showed intense membranous staining for EpCAM (Panel DI), no nuclear and intense staining for Ep-ICD (Panel DII) and membranous staining for β-catenin (Panel DIII). These different staining patterns observed in the same patient support observations of differential expression of these proteins in different subsets of thyroid cancers.

Box-Plot Analysis.

Figure 3:
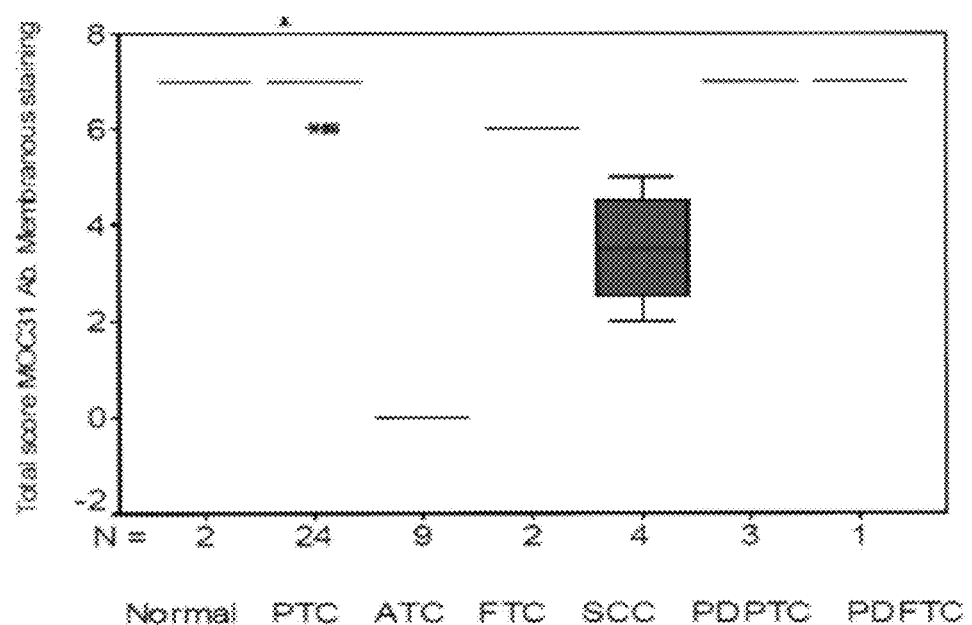
FIG. 3. Box-Plot analysis of EpEx, Ep-ICD and β-catenin expression in thyroid cancers. Box plots showing distribution of total immunostaining scores determined by immunohistochemistry in paraffin-embedded sections of normal thyroid tissues and different types of thyroid cancers. The vertical axis gives the total immunostaining score, obtained as described in Example 1. Panel A shows box plots for EpEx staining—I depicts membranous localization in normal tissues and PTCs, no detectable expression in ATCs and varying reduced expressions in FTC and SCC (with a median score of 3, bold horizontal line). Panel AII depicts cytoplasmic localization of EpEx in normal tissues, PTCs, PDPTC, PDFTC and FTCs, no detectable expression in ATCs and varying reduced expression in SCCs. Panel AIII depicts no detectable EpEx nuclear localization in normal tissues and all subtypes of thyroid cancers. Panel B shows box plots for Ep-ICD staining. Panel BI shows variable Ep-ICD membrane localization in normal tissues, PTCs, ATCs, FTCs and SCCs, PDPTC and PDFTC. Panel BII depicts cytoplasmic Ep-ICD localization in normal tissues, PTCs, ATCs, FTCs and SCCs, PDPTC and PDFTC. Panel BIII depicts nuclear localization in ATCs and varying expression in SCCs, (with a median score of 3, bold horizontal line, range 0-4, as shown by vertical bars), as compared to PTCs, FTCs, PDPTC, PDFTC and normal thyroid tissues with a median score of 0. Panel C shows box plots for β-catenin staining—CI depicts nuclear staining in ATCs only. Panel CII shows cytoplasmic β-catenin in all the subtypes of thyroid cancers analysed. Panel CIII shows membranous β-catenin in normal tissues and all the subtypes of thyroid cancers analyzed except most of the ATCs. Panel D shows Ep-ICD nuclear staining in different subtypes of thyroid cancers using the Visiopharm Integrator System. All the ATCs and one PDPTC and one PDFTC analyzed showed nuclear Ep-ICD expression.
Figure 3:
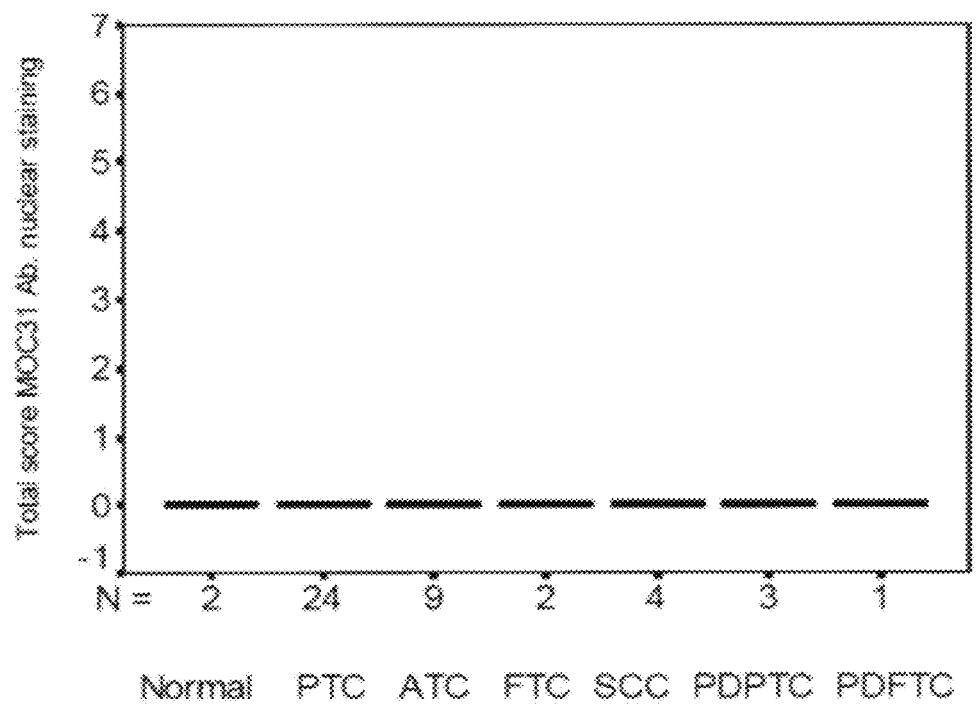
Figure 3:
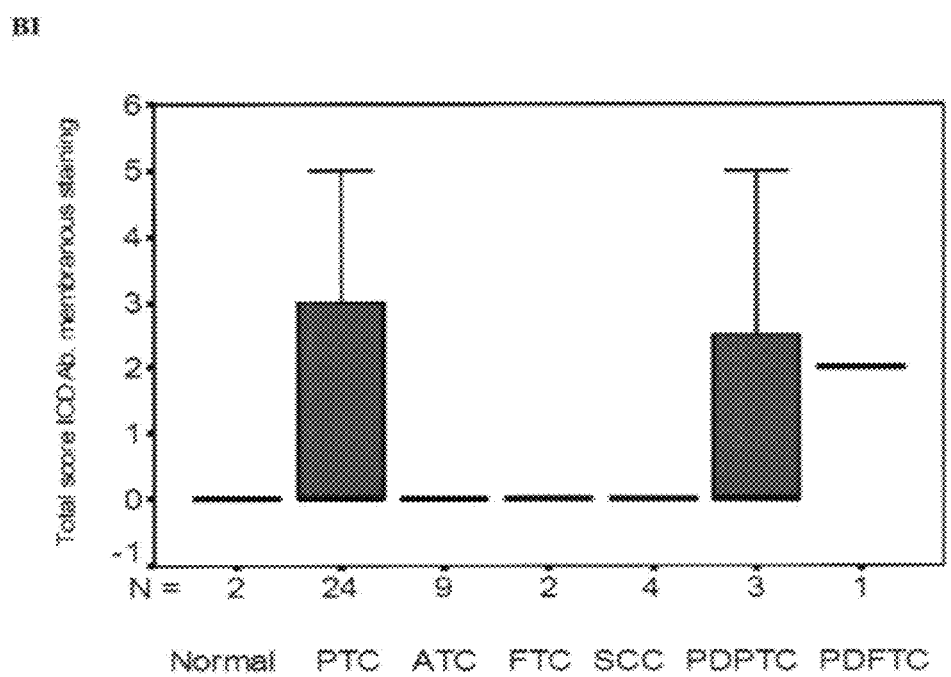
Figure 3:
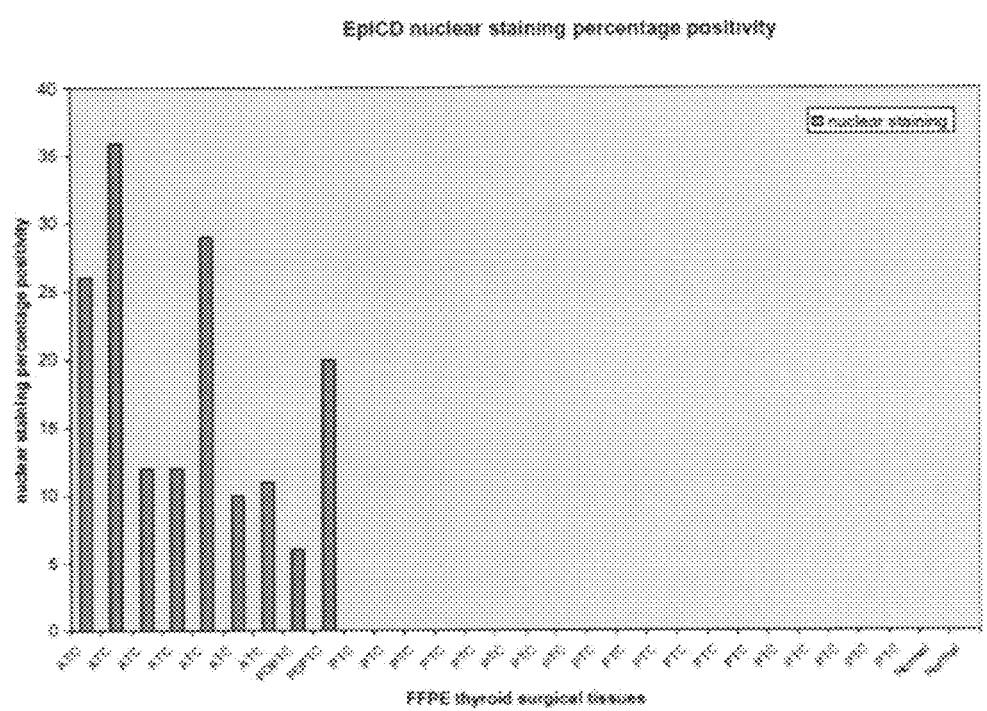

The distribution of total immunostaining scores of EpEx, Ep-ICD and β-catenin, determined in paraffin-embedded sections of normal thyroid tissues and different subtypes of thyroid cancers are shown in FIG. 3. Panel A shows box plots for EpEx staining—AI depicts membranous EpEx localization in normal tissues and PTCs, no detectable expression in ATCs and varying reduced expressions in FTC and SCC (with a median score of 3, bold horizontal line). Panel AII depicts cytoplasmic EpEx localization in normal tissues, PTCs, PDPTC, PDFTC and FTCs, no detectable expression in ATCs and varying reduced expression in SCCs. Panel AIII depicts no detectable nuclear EpEx staining in normal tissues, or any of the thyroid cancers.

Panel B shows box plots for Ep-ICD staining—I depicts membranous Ep-ICD localization in some PTCs, PDFTC and PDPTC, but no membranous staining in ATCs, FTCs and SCCs. Panel BII depicts cytoplasmic Ep-ICD localization in normal tissues, PTCs, ATCs, FTCs and SCCs, PDPTC and PDFTC. Panel BIII depicts nuclear Ep-ICD localization in ATCs and varying expression in SCCs, (with a median score of 3, bold horizontal line, range 0-4, as shown by vertical bars), as compared to PTCs, FTCs, PDPTC, PDFTC and normal thyroid tissues with a median score of 0.

Panel C shows box plots for β-catenin staining—I depicts nuclear staining in ATCs only. Panel CII shows cytoplasmic β-catenin in all the subtypes of thyroid cancers analyzed. Panel CIII shows membranous β-catenin in normal tissues and all the subtypes of thyroid cancers analyzed except most of the ATCs.

The immunohistochemical scoring data were further verified using the Visiopharm Integrator System. FIG. 3D shows the Ep-ICD nuclear staining in different subtypes of thyroid cancers. All the ATCs and one PDPTC and one PDFTC analyzed showed nuclear Ep-ICD expression.

Quantitative Real-Time RT-PCR Analysis of EpCAM expression in Thyroid Cancers

Figure 4:
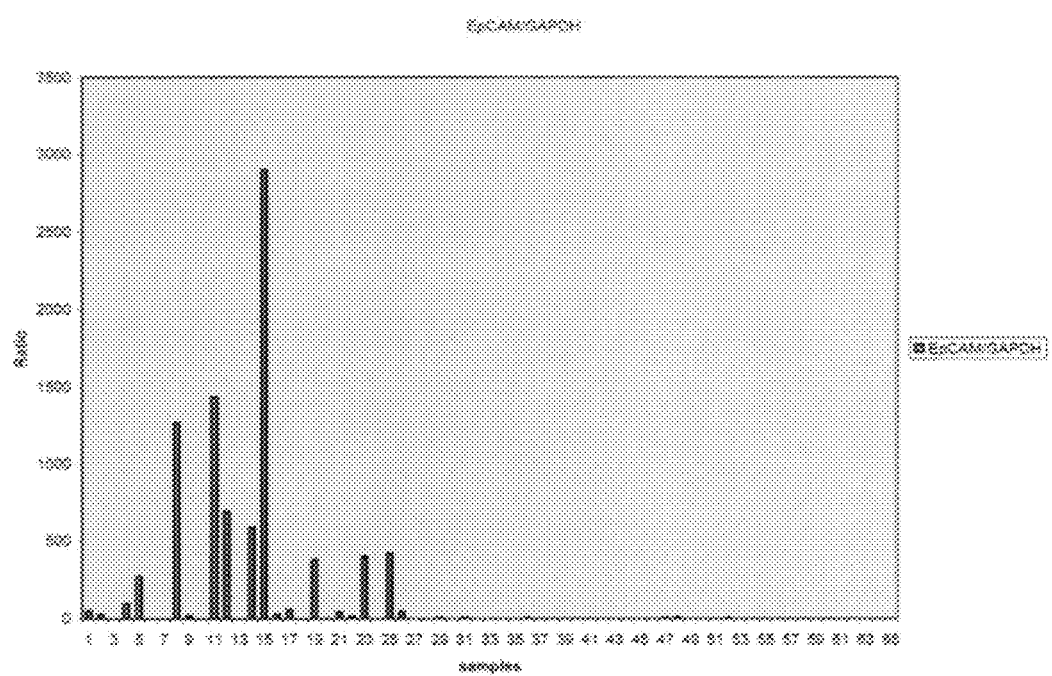
FIG. 4. Quantitative Real Time PCR analysis of EpCAM in human thyroid primary tumors. The histogram shows the levels of EpCAM transcripts in different subsets of thyroid cancers.

The differential expression of EpCAM in aggressive and non-aggressive thyroid cancers was determined at transcript level by Q-PCR. FIG. 4 shows the levels of EpCAM transcripts in thyroid tumors and non-malignant (histologically normal) thyroid tissues. The ATCs showed very low levels of EpCAM transcripts in comparison with FTCs and PTCs. No correlation was observed between EpCAM transcripts and aggressiveness of thyroid cancers.

Association of EpEx, Ep-ICD and β-Catenin Expression with Disease Outcome

Figure 5:
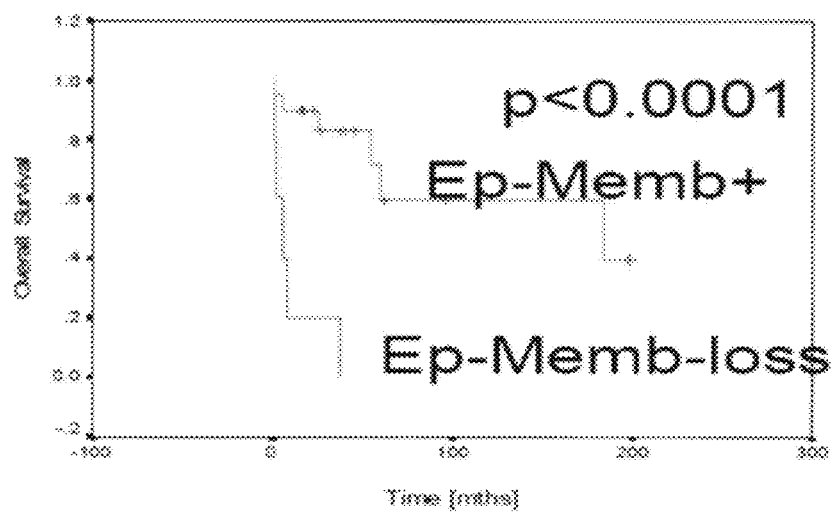
FIG. 5. Kaplan-Meier estimation of cumulative proportion of overall survival: (A) loss of membranous EpEx expression. (B) Nuclear Ep-ICD accumulation. (C) Nuclear β-catenin accumulation. (D) concomitant nuclear Ep-ICD and β-catenin expression in thyroid cancers.
Figure 5:
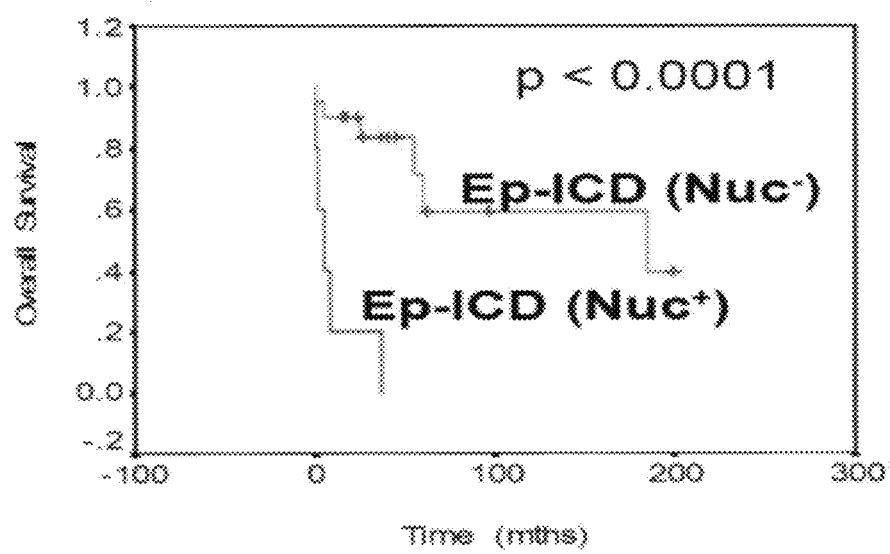
Figure 5:
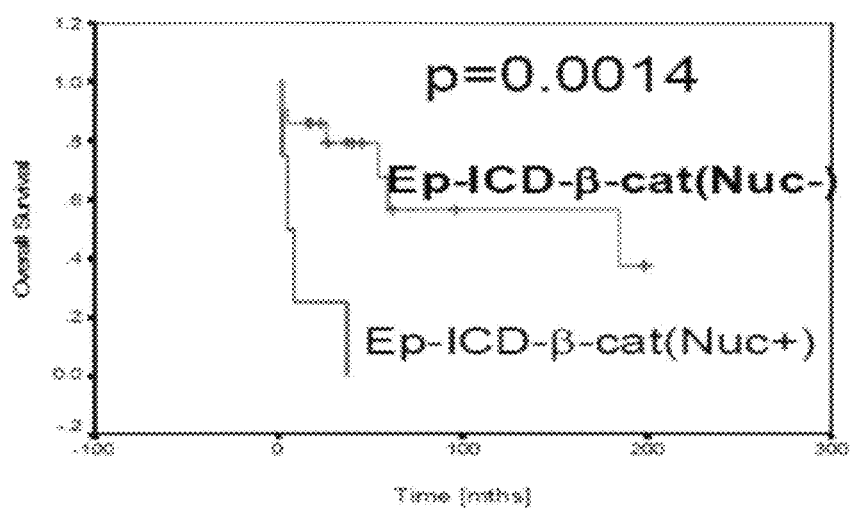

Kaplan-Meier Survival analysis revealed reduced overall survival for thyroid cancer patients showing nuclear Ep-ICD expression (p<0.0001, FIG. 5A). The median overall survival was 5 months in patients showing nuclear Ep-ICD as compared to 185 months for patients who did not. Patients showing loss of membranous EpEx had shorter overall survival (median=5 months) than those showing membranous expression (median=185 months, p<0.0001, FIG. 5B). The patients showing nuclear β-catenin had shorter overall survival (median=5 months) than those who did not (median=185 months, p=0.0014, FIG. 5C). Thyroid cancer patients showing nuclear expression of both Ep-ICD and β-catenin had shorter overall survival (median=5 months) than those who did not (median=185 months, p=0.0014, FIG. 5D).

Subcellular Localization EpEx in Aggressive Human Thyroid Cancer Cell Lines

Figure 6:
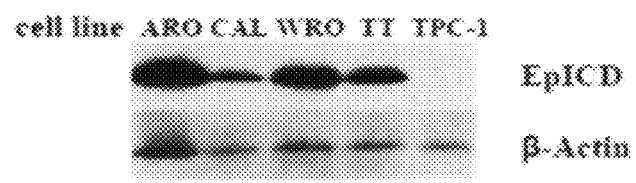
FIG. 6. EpCAM expression in human thyroid cancer derived cell lines. (A) Panel I-Immunocytochemistry-EpEx staining was localized to the plasma membrane in ARO (colon cancer cells, previously considered as ATC cells), WRO (colon cancer cells, previously considered aggressive follicular thyroid cancer cells), and TT (medullary thyroid cancer cells); cytoplasmic Ep-Ex was detected in CAL-62, while no EpEx staining was observed in TPC-1 (low-grade papillary thyroid cancer cells) (Original magnification×200). Panel II-Immunocytochemistry with Ep-ICD (1144). Ep-ICD staining was localized to the plasma membrane and cytoplasm in ARO (colon cancer cells, previously considered as ATC cells), WRO (colon cancer cells, previously considered aggressive follicular thyroid cancer cells), and TT (medullary thyroid cancer cells); cytoplasmic Ep-ICD was detected in CAL-62, while no Ep-ICD staining was observed in TPC-1 (low-grade papillary thyroid cancer cells) (Original magnification×200). Panel III Immunofluorescence-EpEx staining was localized to the plasma membrane of ARO, WRO, and TT (middle panel) and in cytoplasm in CAL-62 (Original magnification× 400). Panel IV—To define the nuclear localization, 4'-6-Diamidino-2-phenylindole (DAPI) nucleic acid staining (Original magnification×400) is shown. (B) Immunofluorescence analysis. Intense EpEx staining with MOC-31 was localized to the plasma membrane in ARO and WRO cells while Ep-ICD staining was cytoplasmic and nuclear in CAL 62 cells (Original magnification×400). (C) Western Blot analysis of EpCAM expression in the same panel of thyroid cancer cell lines. The cell lysates were separated by SDS-PAGE, and were probed for EpCAM using antibody to EpCAM (B302) (upper panel). To ensure the equal loading, the same lysates were probed for beta-actin (lower panel). A 40 kDa band is observed in ARO, WRO and TT cells, but no band was detected in TPC-1 cells. (D) Quantitative Real Time PCR analysis of EpCAM in the same panel of thyroid cancer cell lines. The ratio of EpCAM to GAPDH in ARO, WRO, TT cells is shown, while no transcripts could be quantitated in TPC-1 cells. (E) Immunofluorescence EpEx staining with MOC-31 and β-catenin in the same panel of thyroid cancer cell lines. (F) Immunofluorescence EpEx staining with MOC-31 and c-myc in the same panel of thyroid cancer cell lines.
Figure 6:
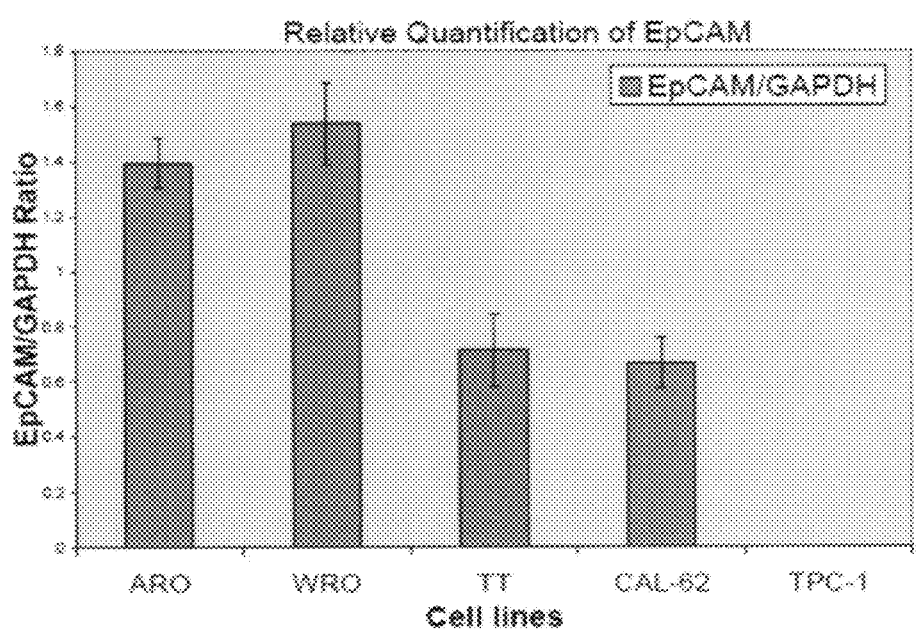
Figure 6:
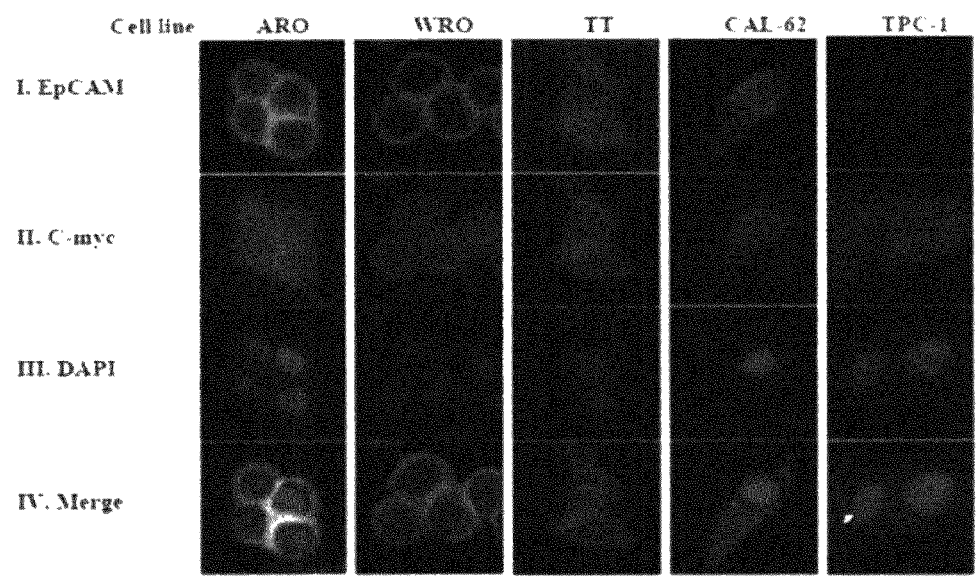

The differential subcellular localization of Ep-Ex and Ep-ICD observed in aggressive and non-aggressive human thyroid cancers is simulated in thyroid cancer cell lines propagated in vitro was determined by immunocytochemistry. Strong EpEx immunostaining localized to the plasma membrane was observed in WRO cells, medullary thyroid cancer cells—TT, and the positive control colon cancer cells—ARO (previously considered as ATC cells) by immunocytochemistry, while no membranous EpCAM staining was detected in anaplastic thyroid cancer cells (CAL-62) and in low-grade papillary thyroid cancer cells (TPC-1) (FIG. 6A panel I). These findings were confirmed by immunofluorescence (FIG. 6A panel III).

Cytoplasmic and nuclear Ep-ICD staining was observed in CAL-62 cells, in comparison, WRO cells showed cytoplasmic Ep-ICD and faint nuclear staining (FIG. 6B panels II and IV). The merged images of EpEx and Ep-ICD staining are presented in FIG. 6B, panel IV depicts strong membrane and faint cytoplasmic staining in WRO cells. In TT cells EpEx showed strong focal staining at cell-cell contacts in the membrane and faint cytoplasmic Ep-ICD staining. In comparison, the anaplastic CAL-62 cells showed nuclear and cytoplasmic Ep-ICD staining and no or faint EpEx staining. In contrast, the non-aggressive papillary thyroid cancer cell line TPC-1 did not show detectable EpEx or Ep-ICD staining.

Western blot analysis corroborated EpEx marked overexpression in ARO, WRO and TT cells; in comparison reduced EpEx levels were observed in CAL-62 cells and no EpEx was detected in TPC-1 cells (FIG. 6C).

Q-PCR analysis showed no marked difference in the levels of EpCAM transcripts in the same panel of cancer cell lines.

FIG. 6D shows EpCAM/GAPDH ratios in ARO, WRO, TT and CAL-62 cells; no transcripts could be quantitated in TPC-1 cells.

EpCAM as Oncogenic Signal Transducer

The oncogenic potential of EpCAM is proposed to be activated by release of its intracellular domain, which can signal into the cell nucleus by activation of Wnt pathway components. To determine if there is any correlation between the loss of EpEx expression from the plasma membrane, cytoplasmic accumulation and translocation into the nucleus, with subcellular localization of the Wnt pathway component β-catenin and expression of target genes such as c-myc, the expressions of these proteins were analyzed in the above panel of thyroid cancer cell lines. FIGS. 6E and 6F show intense EpEx expression at the cell contacts and cytoplasmic and nuclear localization of β catenin and c-myc in WRO and ARO cells, but not in CAL-62, TT and TPC-1 cells.

Discussion

The key findings of the study are: (i) The anaplastic thyroid tumors showed loss of membrane EpEx, but increased Ep-ICD accumulation in cytoplasm and nucleus of tumor cells, that was paralleled by concurrent β-catenin expression, suggesting that Ep-ICD may be acting as an oncogenic signal transducer in these tumors and consequent activation of Wnt pathway components including β-catenin might account for the rapid growth of these tumors and their poor prognosis; (ii) EpEx membrane overexpression was observed in both well differentiated—follicular and papillary thyroid cancers, while a subset of poorly differentiated-follicular and papillary thyroid cancers showed nuclear Ep-ICD; (iii) EpEx was overexpressed on the surface of cancer cells in culture, WRO and TT, but was not detected on the membrane in anaplastic thyroid cancer cells (CAL62) and in the less aggressive cells TPC-1, while nuclear Ep-ICD was detected in CAL62 cells, supporting the clinical findings.

The study is the first report using an antibody specific for the cytoplasmic domain of Ep-ICD that demonstrates its cytoplasmic and nuclear accumulation in ATCs. The regulated intramembrane proteolysis (RIP) of EpCAM has recently been proposed to produce Ep-ICD that has been shown to transduce EpCAM signaling in cancer cells and activate Wnt proteins-resulting in increased nuclear accumulation of β-catenin and the target genes—c-myc and cyclinD1 (Munz et al., 2009). It is demonstrated that concomitant expression of cytoplasmic and nuclear Ep-ICD and β-catenin in ATCs, suggesting that activation of Ep-ICD signaling and consequent Wnt pathway component activation might account for the rapid growth of ATCs.

β-catenin plays an important role as a signaling factor involved in canonical Wnt pathway [Li H et al., 2002]. Nuclear localization of β-catenin is involved in precancerous change in oral leukoplakia [Ishida K et al., 2007] and is known to associate with malignant transformation of human cancers including colorectal, gastric and esophageal tumors [Morin P J 1997, Ogasawara N 2006, Takayama T, 1996, Zhou X B 2002]. The activation of canonical Wnt signaling pathway results in nuclear translocation of β-catenin [Lustig B 2003], hence nuclear β-catenin is a marker for active cell proliferation. In contrast to membranous and cytoplasmic expression, nuclear localization of β-catenin is implicated in tumor progression. The nuclear β-catenin expression in ATCs is a reflection of the aggressive nature of these tumors.

Further, the in vitro findings in aggressive thyroid cancer cell lines CAL62 suggest colocalization of Ep-ICD, β-catenin and c-myc supporting the activation of oncogenic Ep-ICD signaling, Wnt pathway component activation and overexpression of its target protein—cmyc that might account for the aggressive behavior of ATCs and a subset of SCCs, PDPTCs and PDFTCs. The survival analysis data also demonstrate association of loss of membranous EpEx with reduced overall survival of thyroid cancer patients ($p<0.0001$). Furthermore, nuclear Ep-ICD accumulation ($p<0.0001$) and nuclear β-catenin expression ($p=0.0014$) alone, or concomitant with Ep-ICD ($p=0.0014$) were found to be associated with reduced overall survival (median=5 months) as compared to those thyroid cancer patients who did not show nuclear accumulation of these proteins (median=185 months). This is the first report underscoring the clinical significance of nuclear Ep-ICD alone, or in correlation with nuclear β-catenin, as adverse prognosticators for aggressive thyroid cancers.

The in vitro findings in thyroid cancer cell lines and primary thyroid tumors suggest EpEx overexpression in the plasma membranes of well and poorly differentiated thyroid cancers and underscore its potential as an immunotherapeutic target. It is noteworthy that in an earlier immunohistochemical study, Ensinger et al., (2006) reported EpEx overexpression in well and poorly differentiated thyroid cancers, but no expression was observed in the 22 ATCs analyzed. The results also confirm the loss of EpEx expression from the cell surface in ATCs using MOC-31, an antibody that recognizes the extracellular domain of Ep-CAM. EpEx overexpression on the plasma membrane of most well and poorly differentiated follicular and papillary thyroid tumor cells make it an ideal candidate as a cancer marker as well as an immunotherapeutic target. The loss of membrane EpEx and its nuclear localization in ATCs suggests that novel therapeutic approaches are needed for targeting Ep-ICD in these tumors.

CONCLUSIONS

In conclusion, loss of membranous EpEx and nuclear accumulation of Ep-ICD in aggressive thyroid cancers (anaplastic thyroid cancers and some poorly differentiated papillary thyroid cancers) was demonstrated. A concomitant increase in nuclear β-catenin in these tumors suggested activation of Wnt pathway signaling in these tumors. Further, loss of membranous EpEx, or nuclear accumulation of Ep-ICD alone, or in combination with β-catenin, was associated with poor overall survival of thyroid cancer patients. Ep-ICD may serve as a marker for aggressive thyroid cancers and is a potential target for novel therapeutics.

Example 2

EpCAM—Potential Therapeutic Target

Inhibition of EpCAM-Positive Thyroid Cancer Cell Proliferation Upon Treatment with VB4-845/VB6-845

Figure 7:
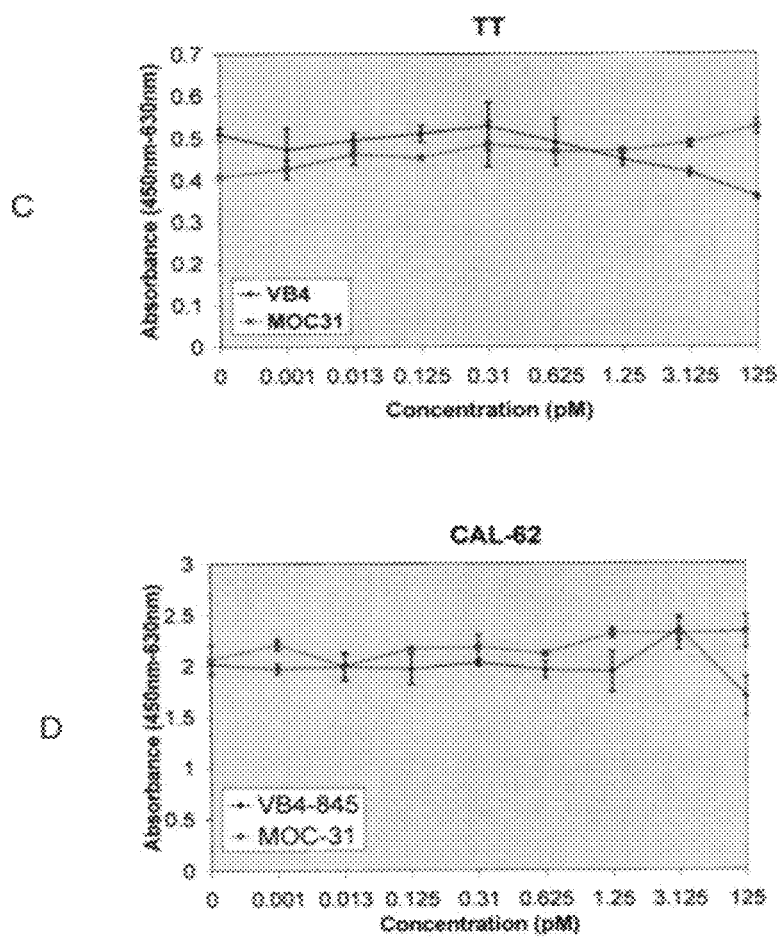
FIG. 7 shows inhibition of EpCAM-positive thyroid cancer cell proliferation upon treatment of cancer cell lines and a positive control colon cancer cell line with the immunotoxin VB4-845/VB6-845.

The effects of EpCAM-specific immunotoxin, VB4-845/VB6-845, on cell proliferation were examined in the panel of thyroid cancer cell lines as well as in the positive control colon cancer cell line with different levels of EpCAM expression. As shown in the FIG. 7, the MTT based cell viability assay showed that VB4-845 inhibited proliferation of WRO and ARO cells, with $IC_{50}$ of 1 pM and 0.7 pM, respectively. In comparison, the medullary thyroid cancer cell line, TT, was marginally responsive to the immunotoxin treatment, while the papillary cell line, TPC-1, and anaplastic cell line, CAL-62, with no detectable membrane EpCAM expression were non-responsive to VB4-845. Similar results were observed in the same cell lines treated with VB6-845 (data not shown).

Induction of Apoptosis by VB4-845 in Thyroid Cancer Cell Lines.

Figure 8:
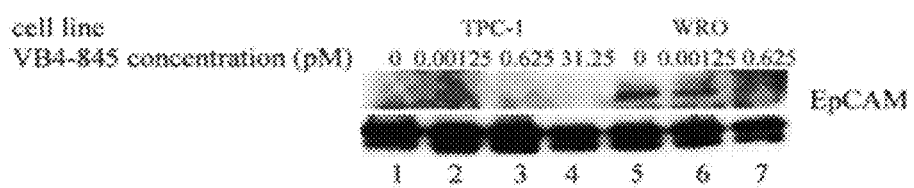
FIG. 8 shows the effects of VB4-845 on EpCAM expression in cell lines determined by Western blotting before and after treatment with different concentrations of VB4-845.

Cell cycle analysis of VB4-845 treated thyroid cancer cells by FACS showed a time dependent induction of apoptosis reflected by a marked increase in subG0 fraction in WRO and the positive control ARO cells as compared to TT and TPC-1 cells. The effects of VB4-845 on EpCAM expression in cell lines were also determined by Western blotting before and after treatment with different concentrations of VB4-845. FIG. 8 shows a dose dependent decrease in EpCAM expression in WRO cells treated with the immunotoxin; no EpCAM expression was detected in untreated or VB4-845 treated TPC-1 cells.

VB4-845 Cytotoxicity Resulted from the Binding of Immunotoxin and EpCAM.

Immunotoxin VB4-845 is a recombinant fusion protein that combines an anti-EpCAM single chain variable fragment with the toxicity of Pseudomonas exotoxin A. The protein is flanked by two hexahistinide tags. As determined in flow cytometry assay, the anti-His antibody was detected in the cells showing EpCAM expression, after two hours incubation with VB4-845.

Figure 9:
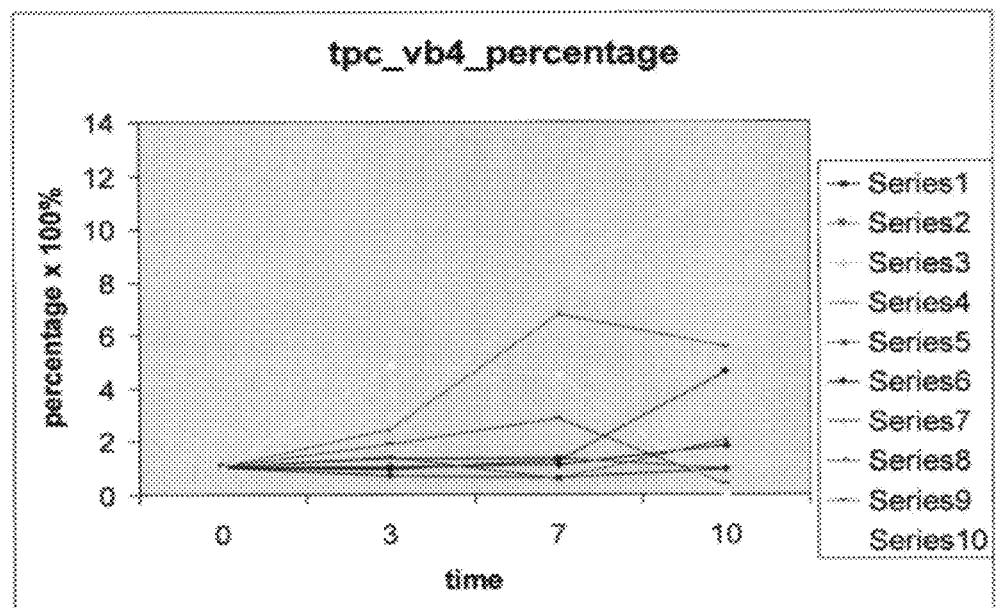
FIG. 9 shows tumor size variation in SCID mice treated with Thyroid papillary carcinoma-1 (TPC-1) cells and VB4 (A) and PBS (B).
Figure 9:
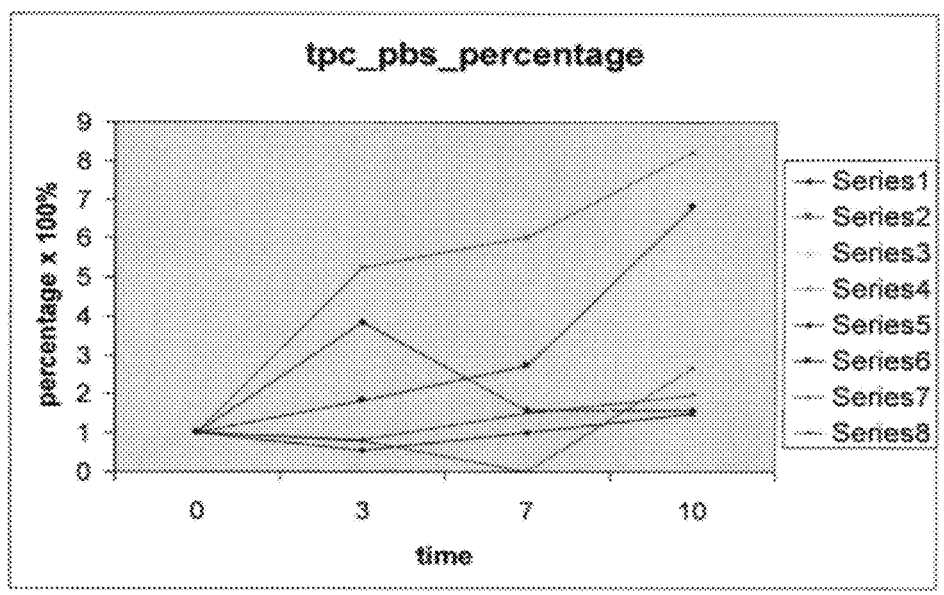

TPC-1 cells ($10^6$) were injected into 6-week old SCID mice. Four weeks later, 7.5 ug VB4 in 100 ul PBS was peritumorally injected for each tumor every 2 days. Approximately two weeks later, the mice were sacrificed mainly due to the oversized tumor. The size of the tumors were measured and compared between VB4 treatment and PBS treatment. Also the EpCAM expression was screened for TPC-1 both in vivo and in vitro. Due to the tumor size variation, the tumor volumes were converted into percentage. With VB4 treatment, four out of ten tumors decreased (FIG. 9(A)), while only one out of eight tumors decreased in PBS group (FIG. 9(B)).

Example 3

The following materials and methods were employed in the Study described in this Example.

Patients and Tissue Specimens:

The study was approved by Mount Sinai Hospital Research Ethics Board, Toronto, Canada. For IHC analysis, archived tissue blocks of normal thyroid tissues (N=9), Non-neoplastic-Hyperplastic/colloid nodules (N=1), papillary thyroid carcinoma (PTC, N=86), follicular thyroid carcinoma (FTC, N=2), poorly-differentiated PTC (N=1), poorly-differentiated FTC (N=1), medullary thyroid carcinoma (N=3), Insular carcinoma (N=6), SCC (N=4), anaplastic thyroid carcinoma (N=11) were retrieved from the tumor bank, reviewed by the pathologist and used for cutting tissue sections for immunostaining with Ep-ICD and EpEx (Moc31) antibodies as described below.

The following is a discussion of the results of the study.

Scatter Plot Analysis

Figure 10:
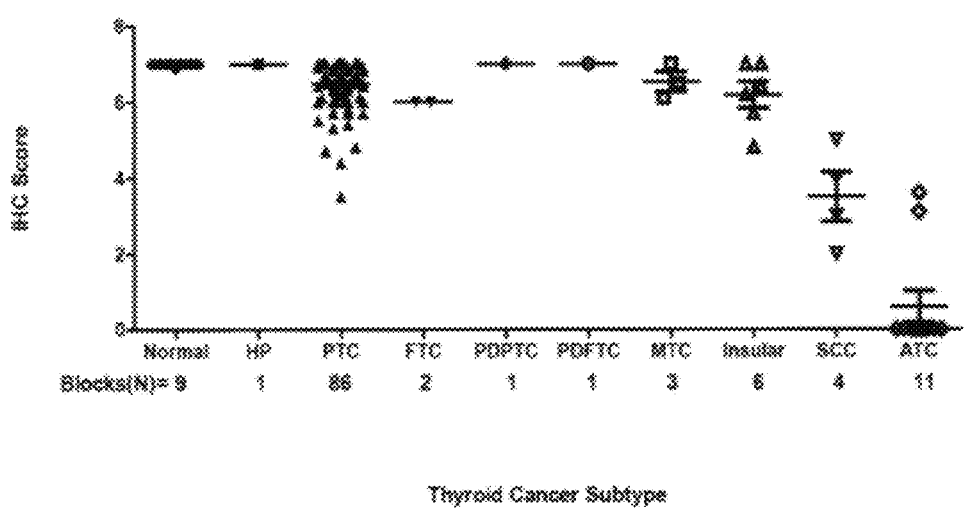
FIG. 10 is a scatter plot showing EpEx Membrane Staining in Thyroid Cancers.
Figure 11:
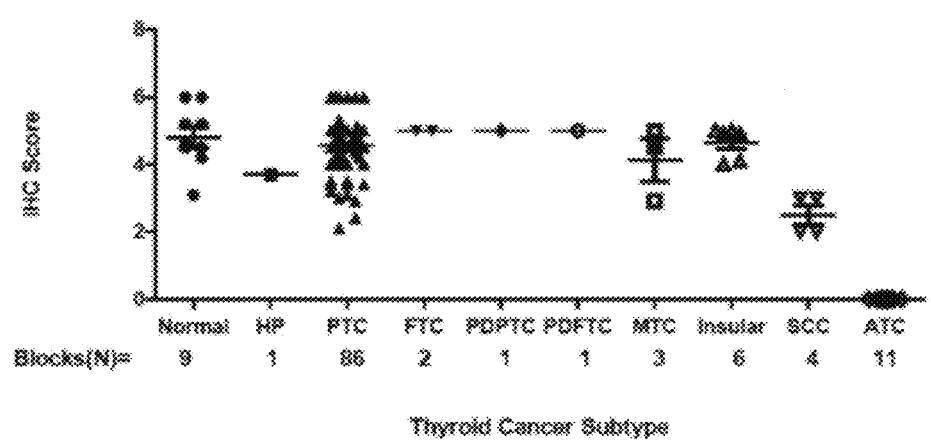
FIG. 11 is a scatter plot showing EpEx Cytoplasmic Staining in Thyroid Cancers.

The scatter plots in FIG. 10-14 illustrate the distribution of Ep-ICD and EpEx membrane/cytoplasmic/nuclear immunohistochemical staining scores in the normal thyroid tissue and nine subtypes of thyroid tumor tissues analyzed. The ATC and SCC groups showed marked reduction in membranous EpEx staining with an average score of less than 4, with insular showing moderate decrease in membranous EpEx. Notably, ATCs showed loss of EpEx with the membrane IHC score of less than 1 (FIG. 10). Similar to the normal thyroid tissue group, the other less aggressive thyroid tumor subtypes showed high EpEx membrane staining with average IHC scores greater than 6 (FIG. 10). In the observation on the EpEx cytoplasm staining (FIG. 11), similar as the normal thyroid group, some less aggressive thyroid cancer subtypes such as PTC, FTC and showed higher EpEx staining than those more aggressive thyroid cancer subtypes including ATC, SCC and insular subtypes. The ATC group showed no detectable low EpEx staining or faint immunoreactivity.

Figure 12:
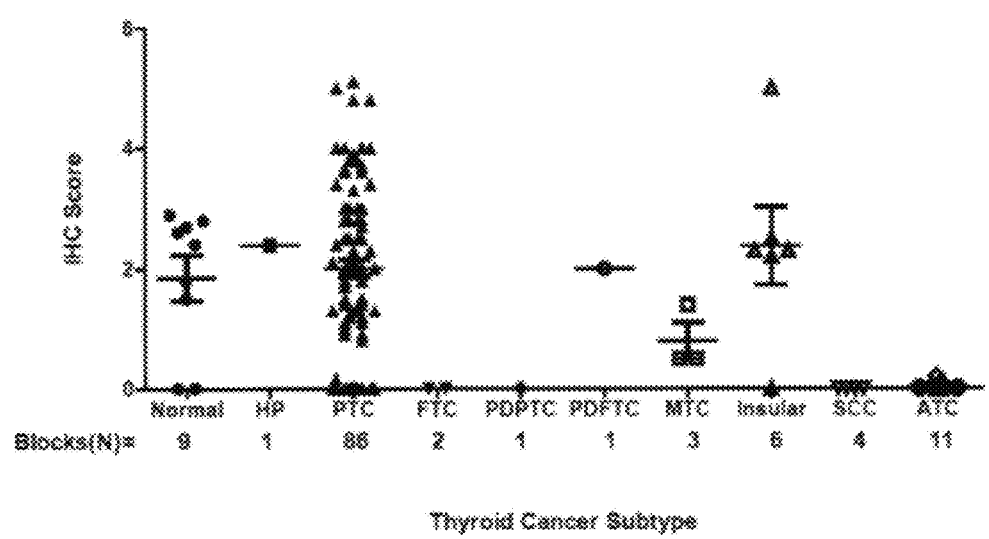
FIG. 12 is a scatter plot showing Ep-ICD Membrane Staining in Thyroid Cancers.
Figure 13:
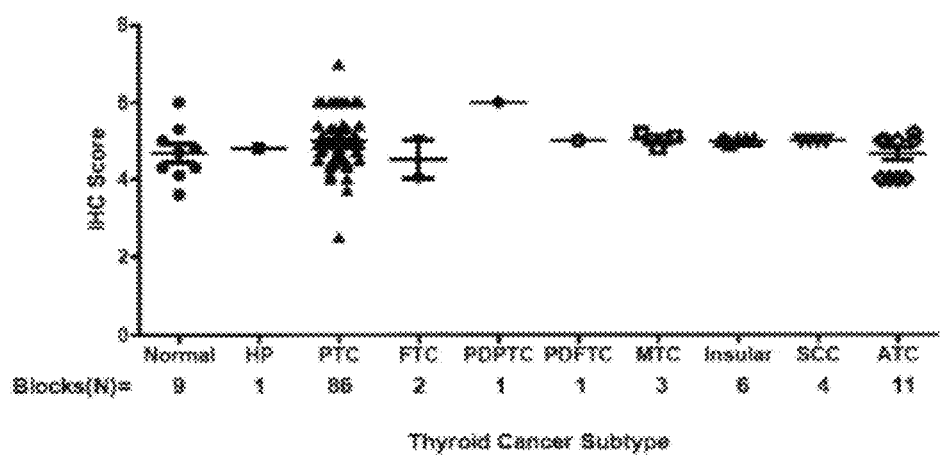
FIG. 13 is a scatter plot showing Ep-ICD Cytoplasmic Staining in Thyroid Cancers.
Figure 14:
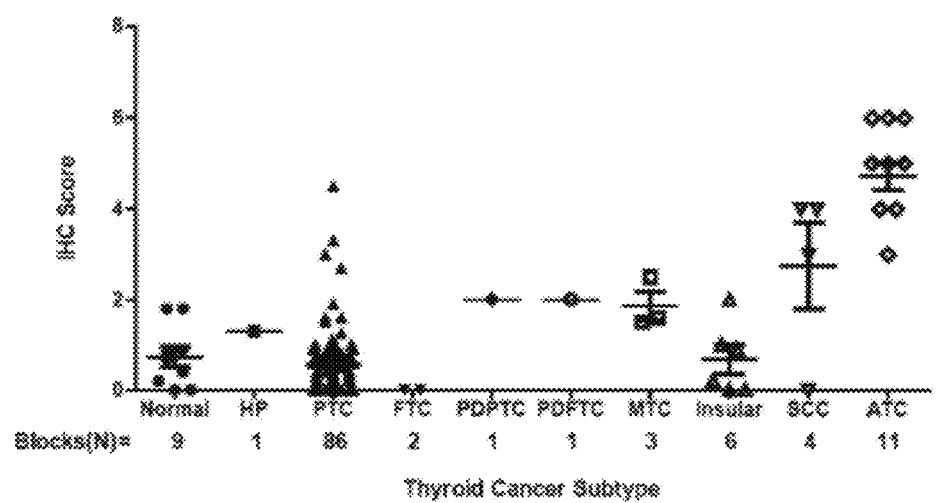
FIG. 14 is a scatter plot showing Ep-ICD nuclear Staining in Thyroid Cancers.

Importantly, using an antibody specific to the intracellular cytoplasmic domain of EpCAM (Ep-ICD), the membrane staining is shown in FIG. 12 and FIG. 13 shows the average expression level at IHC score of 4-5 observed in all of the thyroid tumor subtypes and also the normal thyroid group. Elevated nuclear Ep-ICD staining (above the cutoff≥4) was observed in 10 of the 11 ATC tissue blocks examined (FIG. 14) with a mean staining score of 4.7. In the less aggressive subtype SCC group, 2 of the 4 cases showed nuclear Ep-ICD staining reaching cutoff of 4. Among all the 86 PTC tissue blocks, the majority of the tumors showed very low EpICD nuclear staining with an average score of 0.6 (Table 2), which is similar to the normal group. Other subtypes such as HP, FTC, PDPTC, PDFTC, MTC, Insular, all showed low levels of EpICD nuclear staining with Ep-ICD nuclear expression scores between 0 to 2 (FIG. 14).

Immunohistochemical Analysis of Ep-ICD and EpEx Expression in Thyroid Tumors

Among the two tumor thyroid cancer subtypes (papillary thyroid carcinoma and anaplastic thyroid carcinoma) that were compared (Table 2), the ATC group demonstrated nuclear Ep-ICD positivity in 10 of 11 tissue blocks (90.9%) when choosing a cut off value of ≥4 to determine positivity, while all the 11 tissues showed loss of EpEx membrane expression at a cutoff value of ≤4. Only 1 of 86 PTC tissues (1.2%) demonstrated nuclear Ep-ICD positivity. The correlation of a high nuclear EpICD score of 4.5 in PTC with clinical history revealed that the patient was a 35 year old male with evidence of lymph node metastasis. Another PTC patient with a nuclear Ep-ICD score of 3 had metastatic pancreatic cancer with sepsis. The Ep-ICD and EpEx IHC staining scores differed significantly between PTC and ATC groups and distinguished aggressive from non-aggressive thyroid cancer (TCs).

ROC Curve Analysis

Figure 15:
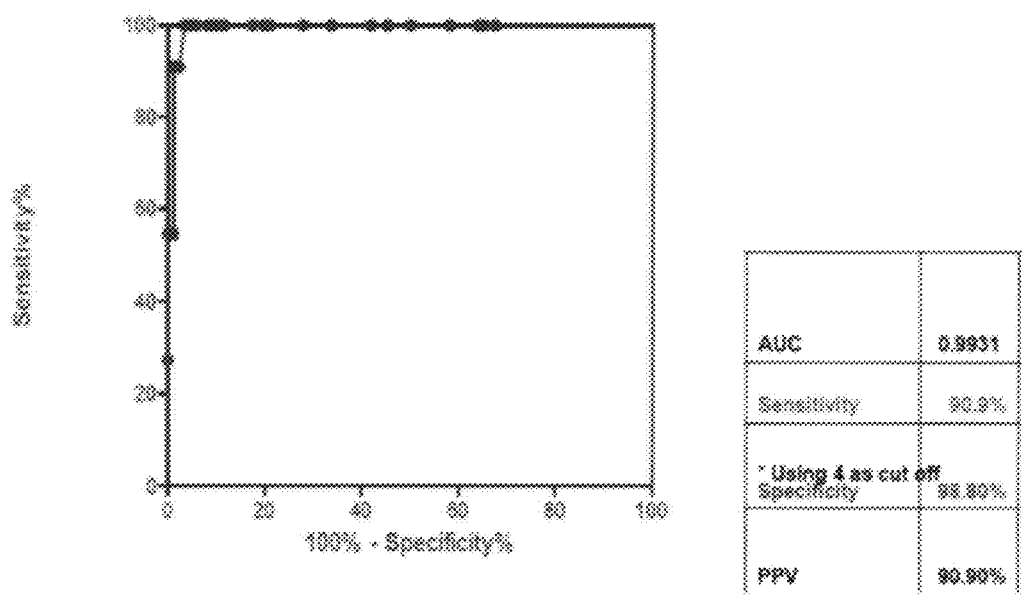
FIG. 15 is a Receiver-operating characteristic ("ROC") curve analysis of EpICD nuclear staining to distinguish ATC from PTC.
Figure 16:
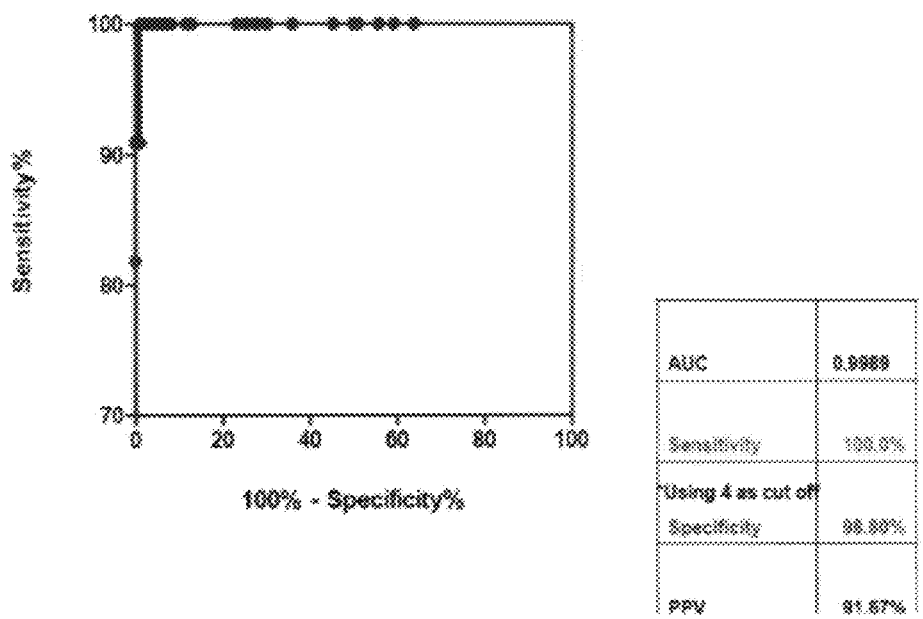
FIG. 16 is a ROC analysis of EpEx Membrane staining to distinguish ATC from PTC.

ROC curves were generated for membrane EpEx and nuclear Ep-ICD to distinguish the most aggressive thyroid cancer subtype—ATC from the most frequently observed but non-aggressive thyroid cancer subtype—PTC (FIGS. 15 and 16), Results of ROC analysis are summarized in Table 4. At a cutoff of ≥4 nuclear Ep-ICD accumulation distinguished ATC from PTC with a sensitivity of 90.9%, specificity of 98.8% and an AUC of 0.9931 (FIG. 15 and Table 4). This suggests the high level of nuclear EpICD accumulation has the potential to serve as a good biomarker to distinguish aggressive from other non-aggressive thyroid cancer subtypes. As shown in FIG. 15 and Table 5, when the cutoff of nuclear EpICD IHC staining score is chosen between 2.5 to 4, this biomarker (nuclear EpICD) can distinguish ATC from PTC with high sensitivity of 90-100% and high specificity of 95-98%. At a cutoff of ≤4, the loss of membrane EpEx expression could also distinguish all of the ATC cases from PTC with a high sensitivity of 100%, high specificity of 98.8% and an AUC value of 0.914 (FIG. 16 and Table 6). The positive predictive value is 91.67% and the negative predictive value is 100% (FIG. 16 and Table 6). As shown in FIG. 16 and Table 7, the cutoff of EpEx membrane IHC staining score is chosen between 3.5 to 5, this biomarker (membrane EpEx) can distinguish ATC from PTC with high sensitivity of 90-100% and high specificity of 95-100%.

Example 4

Filipino Thyroid Cancer Study

The Filipino population has been observed to have a higher incidence of thyroid cancer and the tumors are more aggressive than in non-Filipino patients. The expression of EpEx and Ep-ICD has been analyzed in aggressive and non-aggressive thyroid cancers in Filipino patients. The results are presented below.

Immunohistochemical Analysis of Ep-ICD Expression in Filipino Thyroid Tumors

Figure 17:
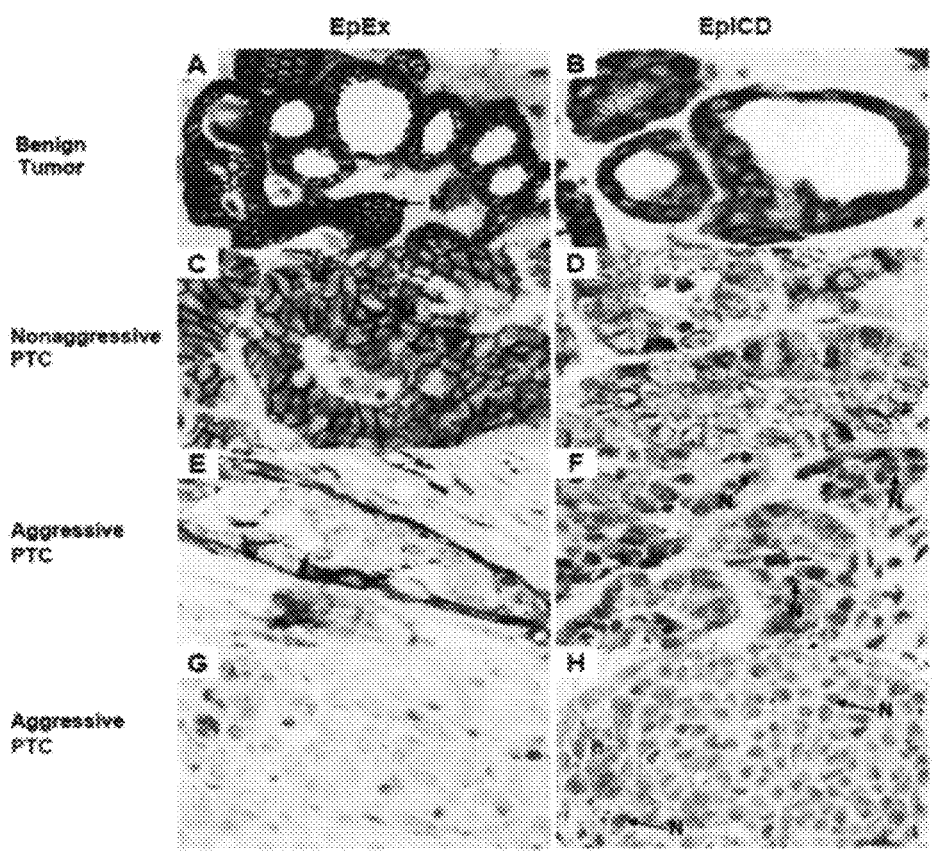
FIG. 17 shows an immunohistochemical analysis of EpEx and Ep-ICD expression in Thyroid Tumors. The photomicrographs show membrane expression of EpEx staining in thyroid benign tumor (A), thyroid non-aggressive malignant tumor (C), thyroid aggressive malignant tumor (E) and (G); Ep-ICD nuclear expression is observed in thyroid benign tumor (B), thyroid non-aggressive malignant tumor (D), thyroid aggressive malignant tumor (F) and (H). M, Membrane staining; N, nuclear staining. All the photomicrographs are at original magnification×400.

Among the three tumor groups that were compared (Table 3), the aggressive malignant tumor group exhibited nuclear Ep-ICD positivity in 7 of 10 tissues and 6 of 10 tissues showed the loss of EpEx membrane expression at an IHC score cutoff value of 4. No loss of EpEx membrane expression was observed in any of the 9 benign tumor cases and 11 non-aggressive malignant cases analyzed. Non-aggressive thyroid cancers did not show nuclear Ep-ICD positivity and only 1 of 9 benign tumors analyzed showed nuclear Ep-ICD positivity. The photomicrographs shown in FIG. 17 depict membrane EpEx expression in benign thyroid tumor (A) and non-aggressive malignant tumor (C), the loss of EpEx membrane expression was observed in some areas of all of the 10 thyroid aggressive malignant tumor cases (E, G). Ep-ICD nuclear expression was observed in the thyroid aggressive malignant tumors (F, H), but not in the benign tumor group and the non-aggressive malignant tumor group (B, D).

Box Plot Analysis

Figure 18:
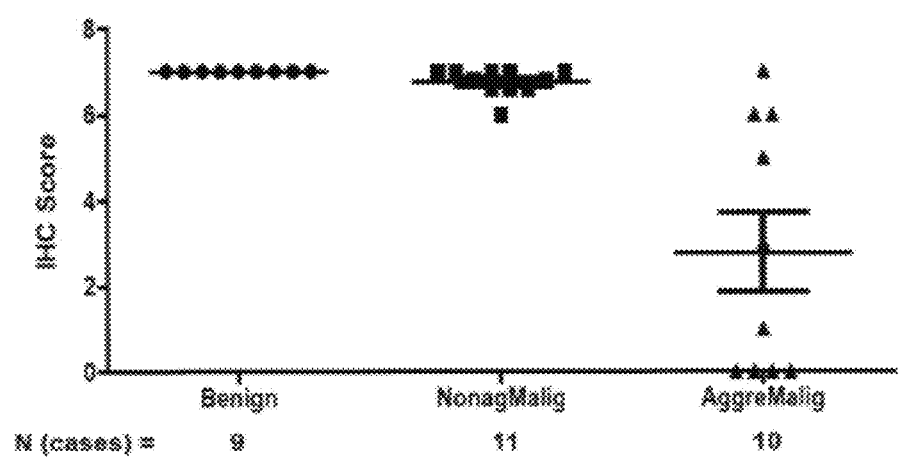
FIG. 18 is a Scatter Plot Analysis of Membrane EpEx Expression in Filipino patients. Scatter plot showing distribution of total immunostaining scores in thyroid benign tumors, clinically non-aggressive and aggressive thyroid malignant tumors. The vertical axis gives the total immunohistochemical staining score as described in the examples. A cutoff of ≥4 was used to determine positivity. Decreased membrane expression of EpEx was observed in most of the aggressive Filipino malignant tumor cases analyzed; high membrane EpEx expression was observed in all of the benign tumor cases and non-aggressive malignant tumor cases. A cutoff score of ≤4 was used to determine positivity (Loss of Membrane expression).
Figure 19:
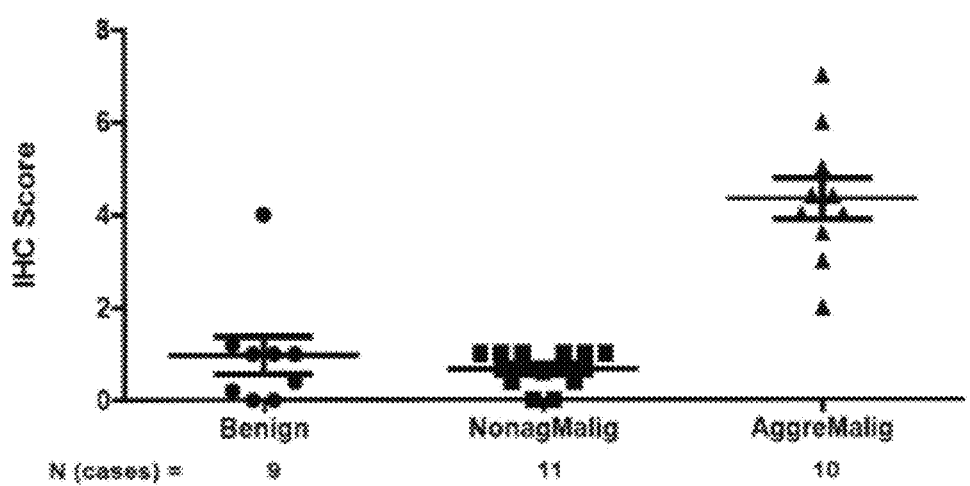
FIG. 19 is a Scatter Plot Analysis of Nuclear Ep-ICD Expression in Filipino patients. Scatter plots showing distribution of total immunostaining scores determined in thyroid benign tumors, clinically non-aggressive and aggressive thyroid malignant tumors. The vertical axis gives the total immunohistochemical staining score as described in the examples. A cutoff of ≥4 was used to determine positivity. Increased nuclear expression of Ep-ICD was observed in almost all aggressive Filipino thyroid malignant tumors analyzed, but not in benign tumors and nonaggressive malignant tumor cases.
Figure 22:
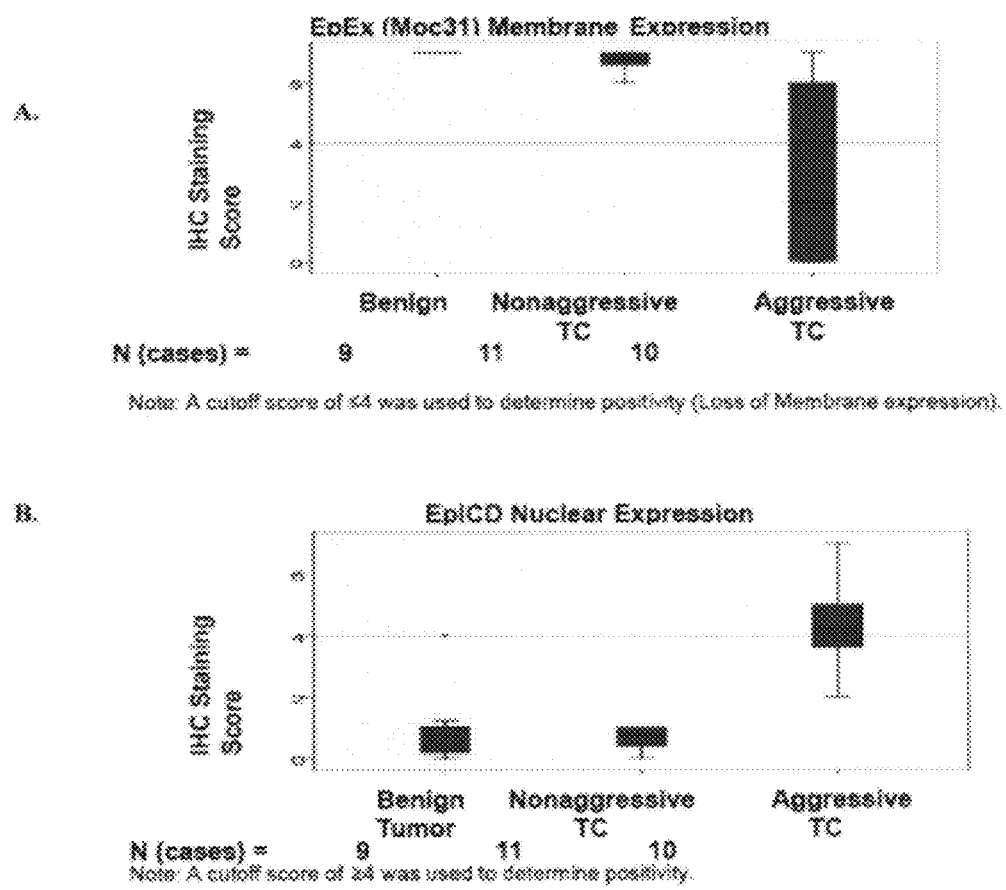
FIG. 22 shows a Box Plot Analysis of Membrane EpEx Expression and Nuclear Ep-ICD Expression. Box plots showing distribution of total immunostaining scores determined by immunohistochemistry of tissue sections of thyroid benign tumors, clinically nonaggressive and aggressive thyroid malignant tumors. The vertical axis gives the total immunohistochemical staining score as described in the examples. A. Decreased membrane expression of EpEx was observed in most of the aggressive Filipino malignant tumor cases analyzed; high membrane EpEx expression was observed in all of the benign tumor cases and nonaggressive malignant tumor cases. A cutoff of ≤4 was used to determine positivity (Loss of Membrane expression). B. Increased nuclear expression of Ep-ICD was observed in almost all aggressive Filipino thyroid malignant tumors analyzed, but not in benign tumors and nonaggressive malignant tumor cases. A cutoff of ≥4 was used to determine positivity.

The scatter plots in FIGS. 18 and 19 and the box plots in FIGS. 21A and 21B and 22A and 22B show the distribution of membrane EpEx and nuclear Ep-ICD staining scores in the three groups (30 cases in total) of Filipino thyroid tumor cases analyzed. Elevated nuclear Ep-ICD staining (above the cutoff≥4) was found in 7 of the 10 aggressive malignant tumors examined (FIG. 22B.), showing a mean staining score of 4.3. Nuclear Ep-ICD staining reached cutoff≥4 was observed in only 1 in the 9 benign tumors and none of the 11 non-aggressive malignant tumor tissues. All of the 9 benign thyroid tumor tissues examined and all of the 11 non-aggressive malignant tumors show high level membrane EpEx staining with a mean score of around 7 scores (FIG. 21(A)). The loss of membrane EpEx expression was observed in two third of the aggressive malignant cases (FIG. 22A.).

ROC Curve Analysis

Figure 20:
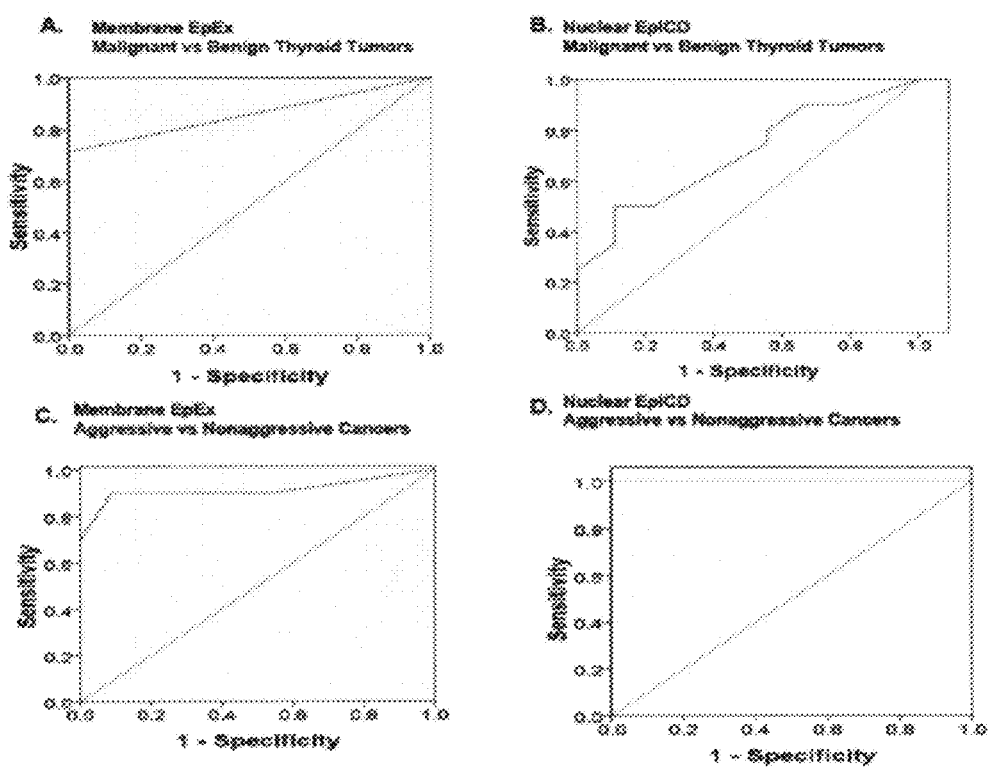
FIG. 20 shows Receiver operating characteristic (ROC) curves of membrane EpEX (A,C) and nuclear Ep-ICD (B,D) in Filipino thyroid benign tumors, non-aggressive and aggressive cancers. ROC curves were generated based on the sensitivities and 1-specificities of membrane EpEx and nuclear Ep-ICD expression. The vertical axis indicates the sensitivity and the horizontal axis indicates the 1-specificity. The sensitivity, specificity, and area under the curve (AUC) values for the cancers are summarized in Table 8.
Figure 21:
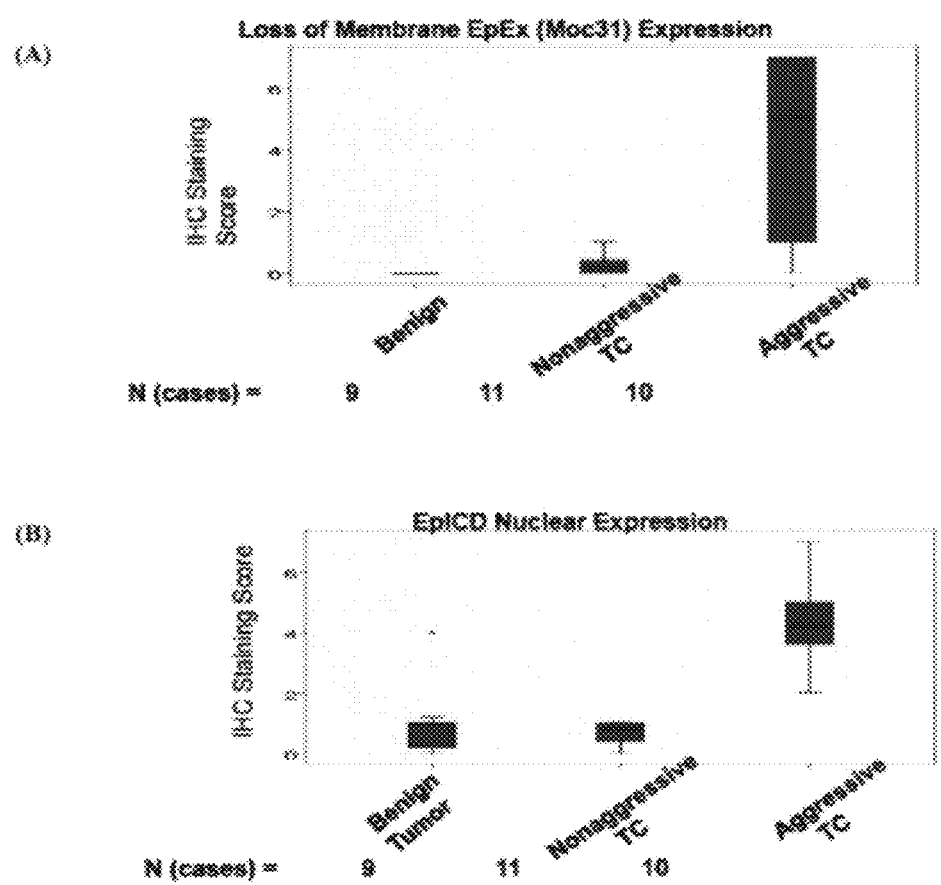
FIG. 21 shows a Box Plot Analysis of Nuclear Ep-ICD (B) and loss of Membrane EpEx Expression (A).

ROC curves were generated for membrane EpEx and nuclear Ep-ICD to distinguish malignant thyroid tumors from benign tumors (FIG. 20A, B) and also to distinguish aggressive malignant tumors from the nonaggressive tumors (FIG. 20C, D). Relevant ROC analysis including results are summarized in Table 8.

Nuclear Ep-ICD accumulation distinguished thyroid malignant tumors from benign tumors with a 33.33% sensitivity, a specificity of 88.89% and with the AUC value of 0.703. Nuclear Ep-ICD accumulation distinguished aggressive thyroid malignant tumors from nonaggressive cancers with an 80% sensitivity, a specificity of 100% and an AUC of 1.0 (Table 8). The loss of membrane EpEx expression distinguished thyroid malignant tumors from benign tumors with a 28.57% sensitivity, a specificity of 100% and with the AUC value of 0.857. Nuclear Ep-ICD accumulation distinguished aggressive thyroid malignant tumors from nonaggressive cancers with a 60% sensitivity, a specificity of 100% and an AUC of 0.914 (Table 8).

Example 5

Ep-ICD Subcellular Localization Index (ESLI) is a Marker of Aggressiveness and Poor Prognosis in Papillary Thyroid Carcinoma The present example illustrates the clinical significance of Ep-ICD subcellular localization index (ESLI) in distinguishing aggressive papillary thyroid carcinoma (PTC) from non-aggressive cases. ESLI was defined as sum of the IHC scores for accumulation of nuclear and cytoplasmic Ep-ICD and loss of membranous EpEx; ESLI=[Ep-ICDnuc+Ep-ICDcyt+loss of membranous EpEx].

To investigate the potential of ESLI as a diagnostic and prognostic marker to identify patients with aggressive PTC, subcellular IHC analysis of tissue specimens was performed. The findings indicate that the nuclear and cytoplasmic accumulation of Ep-ICD and loss of membranous EpEx may be used to detect aggressive PTC cases with high specificity. These observations have been incorporated into the application of an index of malignancy and aggressiveness, ESLI, scored on the basis of Ep-ICD and EpEx subcellular localization to improve the diagnostic sensitivity and specificity for detecting aggressiveness compared to either biomarker alone.

Materials and Methods

Ethics Statement

The study was approved by Mount Sinai Hospital Research Ethics Board, Toronto, Canada.

Clinicopathological Characteristics of Patients and Tissue Specimens

Two hundred patients with PTC or benign thyroid disease were included in this study. The diagnosis was based on histopathological analysis of the tissue specimens. Archived formalin fixed paraffin embedded tissue blocks of 200 patients were retrieved from the Mount Sinai Hospital (MSH) tumor bank, reviewed by the pathologists and used for cutting tissue sections for IHC staining with Ep-ICD and EpEx antibodies as described below. These included 16 benign cases, 63 non-aggressive PTC, and 121 aggressive PTC. The benign cases included multinodular goiters, lymphocytic thyroiditis and benign follicular cysts; non-aggressive thyroid tumors included well differentiated PTC and the aggressive thyroid tumors included well differentiated PTC that showed features such as tumor recurrence, lymph node or distant metastasis, extrathyroidal extension, or aggressive histopathological features such as anaplastic transformation, tall cell variant or angiolymphatic invasion. In addition to these criteria, the clinical and pathological data recorded included clinical tumor stage, site of the lesion, histopathological differentiation, age and gender.

Immunohistochemical Analysis of Ep-ICD and EpEx Expression in Thyroid Carcinomas Anti-human Ep-ICD antibody was obtained from Epitomics Inc. (Burlingame, Calif.). The α-Ep-ICD antibody 1144 recognizes the cytoplasmic domain of human EpCAM and has been used in the a recent study by the inventors on Ep-ICD expression in thyroid carcinoma [Ralhan R. et al., 2010]. Anti-EpCAM monoclonal antibody EpEx (MOC-31, AbD Serotec, Oxford, UK) recognizes an extracellular component (EGF1 domain—aa 27-59) in the amino-terminal region [Chaudry M A et al., 2007]. Formalin fixed paraffin embedded sections (5 μm thickness) of thyroid carcinomas were used for Ep-ICD and EpEx immunostaining as previously described by the inventors [Ralhan R. et al., 2010]. Briefly, after dewaxing and rehydration, antigen retrieval was carried out using a microwave oven in 0.01 M citrate buffer, pH 6.0 and endogenous peroxidase activity was blocked by incubating the tissue sections in methanol containing hydrogen peroxide (0.3%, v/v) for 20 min. After blocking the non-specific binding with normal horse or goat serum, the sections were incubated with either α-Ep-ICD rabbit monoclonal antibody 1144 (dilution 1:1500) or mouse monoclonal antibody MOC-31 (dilution 1:200) for 30 minutes and biotinylated secondary antibody (goat anti-rabbit) for 30 minutes. The sections were finally incubated with VECTASTAIN Elite ABC Reagent (Vector Laboratories, Burlington, ON, Canada) and diaminobenzidine was used as the chromogen.

Immunofluorescence Analysis of Ep-ICD and EpEx Localization in Thyroid Carcinomas Immunofluorescence analysis was carried out using a TRITC-labeled goat anti-rabbit secondary antibody for detecting Ep-ICD (Sigma-Aldrich, 1:200 dilution) and a FITC-labeled goat anti-mouse secondary antibody (Sigma-Aldrich, St. Louis, Mo., 1:200 dilution) for detecting EpEx. Slides were viewed using an Olympus Upright fluorescence microscope (BX61) and images were analyzed using Volocity software (Perkin Elmer, Waltham, Mass.).

Evaluation of Immunohistochemical Staining

Immunopositive staining was evaluated in the five most pathologically aggressive areas of the tissue sections by two researchers blinded to the final diagnosis and the average of these five scores was calculated as described earlier [Ralhan R. et al., 2010]. These sections were scored as follows: 0, <10% cells; 1, 10-30% cells; 2, 31-50% cells; 3, 51-70% cells; and 4, >70% cells showed immunoreactivity. Sections were also scored semi-quantitatively on the basis of intensity as follows: 0, none; 1, mild; 2, moderate; and 3, intense. Finally, a total score (ranging from 0 to 7) of each area was obtained by adding the scores of percentage positivity and intensity for each of the thyroid carcinoma and normal thyroid tissue sections and the average of total scores from the five areas was used for further statistical analysis. Loss of membranous EpEx was calculated as the maximum total score of 7-score for membrane EpEx.

Ep-ICD Subcellular Localization Index (ESLI)

Ep-ICD subcellular localization index (ESLI) was defined as sum of the IHC scores for loss of membranous EpEx and accumulation of nuclear and cytoplasmic Ep-ICD; ESLI= [loss of membranous EpEx+Ep-ICD$_{nuc}$+Ep-ICD$_{cyt}$].

Statistical Analysis

The immunohistochemical data were subjected to statistical analysis using SPSS 20.0 software (SPSS, Chicago, Ill.) and GraphPad Prism 5.0 software (GraphPad Software, La Jolla, Calif.) as described previously [Ralhan R. et al., 2008]. Nonparametric test Mann-Whitney U-test was used for comparisons of benign versus malignant and aggressive PTC versus non-aggressive PTC. P-values of <0.05 were considered significant. Scatter plots were used to determine the distribution of total score of nuclear Ep-ICD expression and membranous EpEx expression in all tissue types examined Receiver operating characteristic (ROC) curve analyses were used to determine the sensitivity, specificity and area under the curve (AUC) values for nuclear Ep-ICD and cytoplasmic Ep-ICD. The cut-offs were based on the optimal sensitivity and specificity obtained from ROC curve analysis. For nuclear Ep-ICD, an IHC score cut-off value of ≥2 was defined as immunopositive for all tissues analyzed for statistical analysis. For membranous EpEx, an IHC score cut-off value of ≤5 was defined as loss of EpEx for all tissues analyzed. Ep-ICD cytoplasmic positivity was taken at an IHC score cut-off value of ≥5. An ESLI score ≥6 was set as the cut-off for distinguishing the malignant tumors from benign cases. An ESLI score >10 was set as the cut-off to differentiate the aggressive PTC from the non-aggressive cases. The correlation between expression of Ep-ICD and ESLI with disease free survival was evaluated using life tables constructed from survival data with Kaplan Meier plots.

Results

Figure 23:
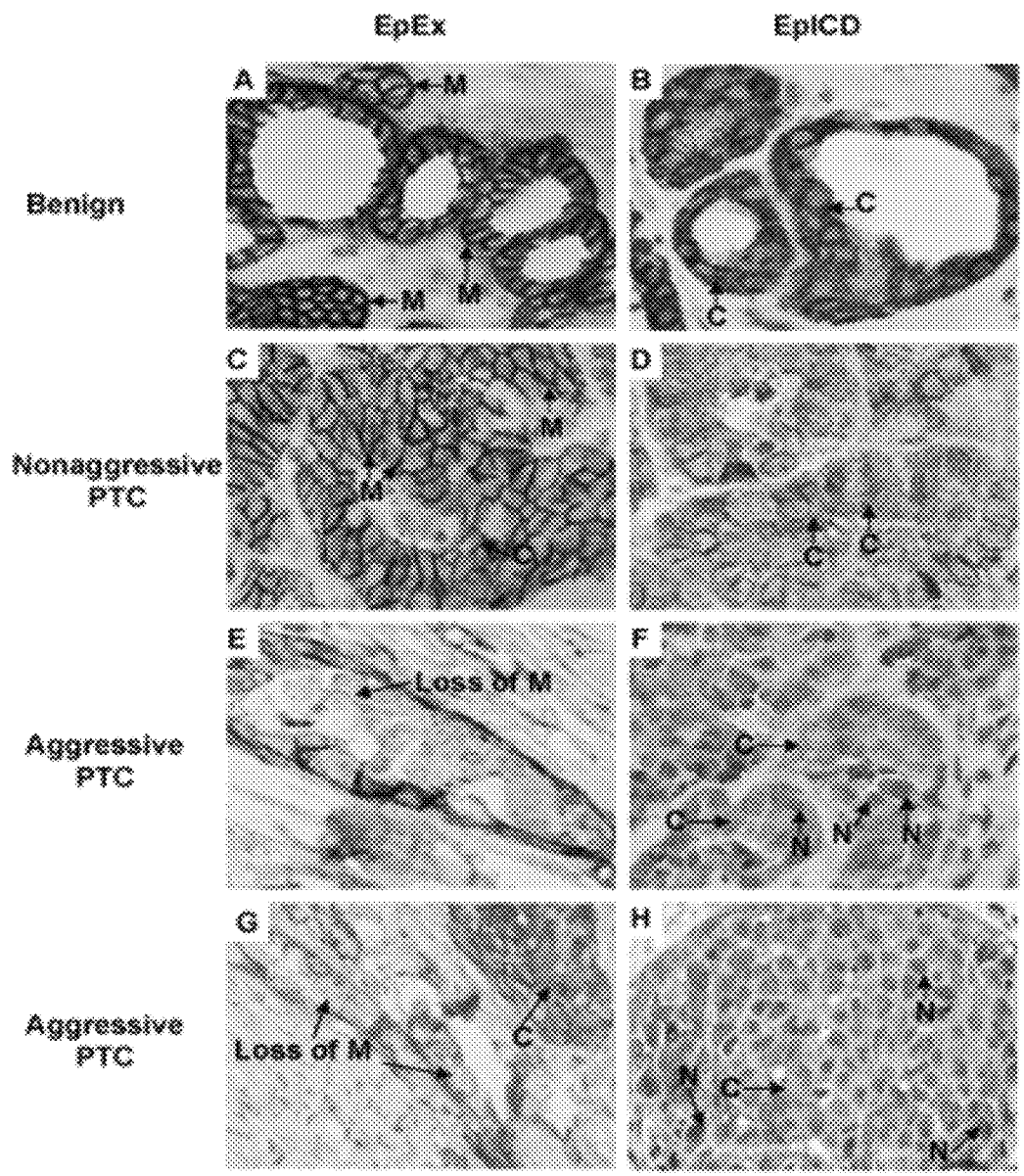
FIG. 23 shows an immunohistochemical analysis of EpEx and Ep-ICD expression in papillary thyroid carcinomas and benign tissues. The representative photomicrographs show immunostaining of EpEx and Ep-ICD in paraffin-embedded thyroid benign nodule goiters, non-aggressive PTC and aggressive PTC tissues. Strong membranous EpEx immunostaining was observed in benign cases (A) and nonaggressive PTC tissues (C); reduced staining of membrane EpEx was observed in aggressive PTC cases (E, G). The benign thyroid nodules and non-aggressive PTC (D) showed predominant cytoplasm localization of Ep-ICD and no detectable nuclear Ep-ICD staining (B, D), while the aggressive PTC cases showed strong nuclear and cytoplasmic Ep-ICD accumulation (F, H). M, membrane staining; C, cytoplasmic staining; N, nuclear staining; Loss of M, loss of membrane expression. Original magnification×400.

Immunohistochemical Analysis of EpEx and Ep-ICD Expression in Papillary Thyroid Carcinomas and Benign Thyroid Tissues Immunohistochemical staining of EpEx and Ep-ICD was carried out in benign thyroid nodular goiters, non-aggressive PTC and aggressive PTC (FIG. 23). Membranous EpEx expression in benign thyroid tissues was observed as a mean IHC score of 6.8 (FIG. 23A) and non-aggressive PTC tissues had a mean IHC score of 6.1 (FIG. 23C). A decrease in membranous EpEx immunostaining was observed in aggressive PTC cases (FIGS. 23E and G). Benign thyroid tumors and non-aggressive PTCs showed predominantly cytoplasmic localization of Ep-ICD and non-detectable nuclear Ep-ICD staining (FIGS. 23B and D). Strong nuclear and cytoplasmic Ep-ICD accumulation was observed in aggressive PTC (FIGS. 23, F and H). Among the 121 aggressive PTC examined, nuclear Ep-ICD localization was observed in 85 tissues (70.3%) when using an IHC score cut-off≥2 to determine positivity (Table 9a, FIG. 24D). Notably, virtually all benign tissues ($^{14}/_{16}$, 87.5%) and non-aggressive PTC ($^{53}/_{63}$, 84.1%) did not show nuclear Ep-ICD immunopositivity based on this cut-off value (Table 1a). Loss of membranous EpEx expression was observed in 111 of 121 (91.7%) aggressive PTC (IHC score cut-off≤5) (Table 9a, FIG. 24B). In contrast, all benign tissues and nearly all non-aggressive PTC ($^{56}/_{63}$, 88.9%) strongly expressed membranous EpEx (FIG. 24A).

Figure 24:
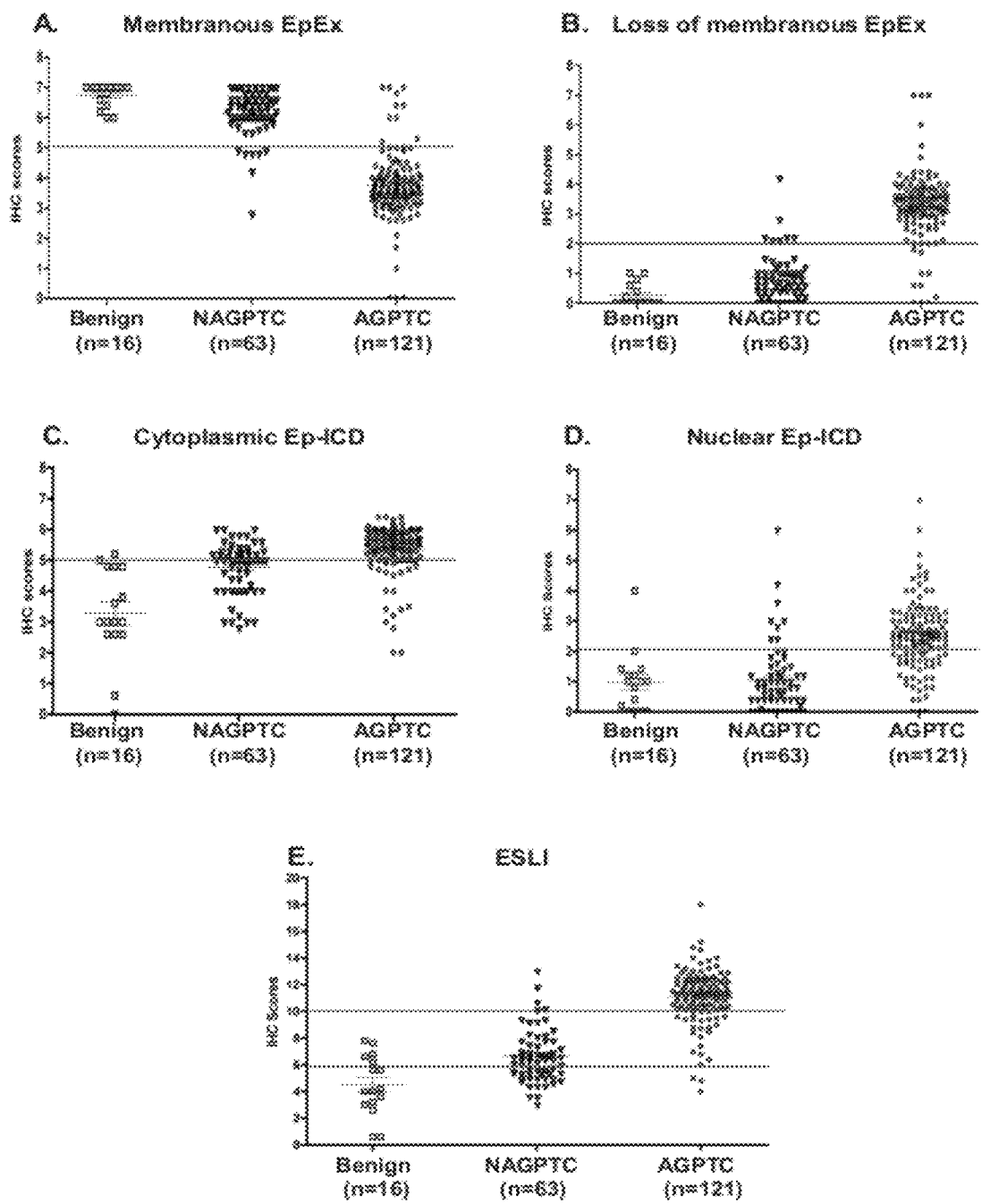
FIG. 24 is a scatter plot analysis of membrane EpEx, Ep-ICD and ESLI ("Ep-ICD subcellular localization index") expression in thyroid tumors. Scatter plots show the distribution of total immunohistochemistry ("IHC") scores determined by immunohistochemical analysis of tissue sections from benign thyroid nodules (n=16), non-aggressive PTC (n=63) and aggressive PTC cases (n=121). The vertical axis gives the immunohistochemical staining score as described in the Methods section. The horizontal bars are the cut-off IHC score threshold derived from the relevant ROC curves to classify aggressive PTC cases from non-aggressive PTC cases with sensitivities and specificities summarized in Table 10. Each point represents an average IHC score of five stained fields in each tissue. The red/green lines show mean±standard error of mean (SEM) values for the markers analyzed. High membrane EpEx expression was observed in all of the benign cases and most of the non-aggressive PTC cases (A). Decreased membrane expression of EpEx was observed in most of the aggressive PTC cases analyzed (B). Increased cytoplasmic (C) and nuclear expression (D) of Ep-ICD was observed in aggressive PTCs as compared to the benign and non-aggressive PTC groups. An increasing trend of ESLI was observed across the three groups of patients correlating with aggressiveness of tumors (E). BN, benign; AGPTC, aggressive PTC; NAGPTC, non-aggressive PTC.

Scatter Plot Analysis of Nuclear and Cytoplasmic Ep-ICD and Membranous EpEx in Papillary Thyroid Cancers The scatter plots in FIG. 24 depict the distribution of membranous EpEx and nuclear Ep-ICD IHC staining scores in the three groups of thyroid tissues analyzed. Using Mann Whitney U test, there were significant differences in nuclear Ep-ICD and cytoplasmic Ep-ICD expression levels between aggressive PTC and non-aggressive PTC (p<0.001) (Table 9b). Similar significant differences in nuclear Ep-ICD and cytoplasmic Ep-ICD levels between the benign thyroid nodules and PTC also (p=0.002, p<0.001 respectively, Table 9b).

ROC Curve Analysis of Cytoplasmic Ep-ICD and Nuclear Ep-ICD in PTC

Figure 25:
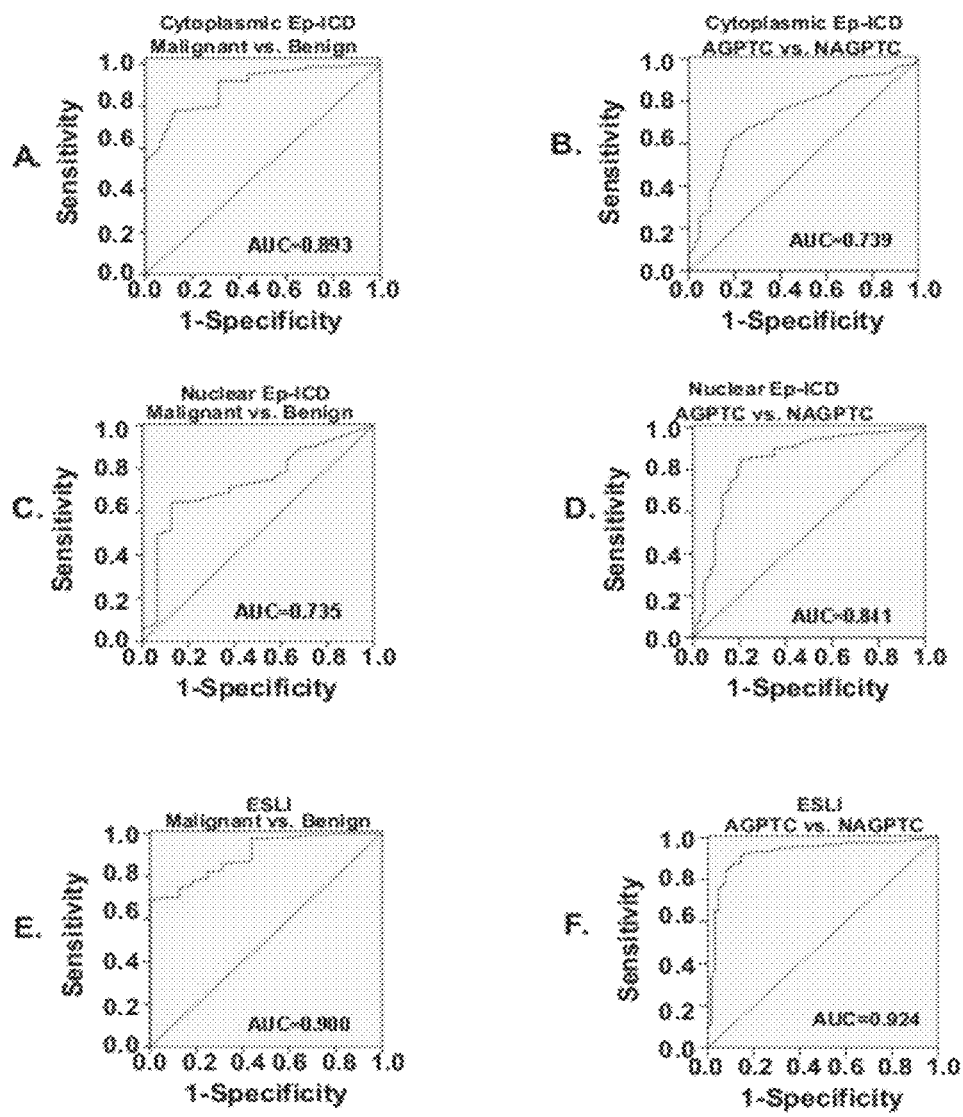
FIG. 25 is a ROC curve analysis of cytoplasmic Ep-ICD, nuclear Ep-ICD and ESLI in thyroid tissues. The vertical axis indicates sensitivity and the horizontal axis indicates 1-specificity. The sensitivity, specificity, and area under the curve (AUC) values for the cancers are summarized in Table 10. ROC curves for malignant vs. benign for cytoplasmic Ep-ICD (A), nuclear Ep-ICD (C) and ESLI (E). ROC curves for aggressive and non-aggressive PTC for cytoplasmic Ep-ICD (B), nuclear Ep-ICD (D) and ESLI (F). AGPTC, aggressive PTC; NAGPTC, non-aggressive PTC.

ROC curves were generated for cytoplasmic Ep-ICD (FIGS. 25A and B) and accumulation of nuclear Ep-ICD (FIGS. 25C and D) to evaluate their ability to distinguish PTC from benign thyroid nodules and aggressive PTC from non-aggressive PTC respectively. ROC curve analysis was performed to evaluate nuclear Ep-ICD accumulation as a potential biomarker for aggressiveness of PTC (FIG. 25D). Our results suggest nuclear Ep-ICD is able to distinguish aggressive PTC from the non-aggressive PTC with an AUC of 0.841, a sensitivity of 70.2% and a specificity of 83.9% when a cut-off score at ≥2 was used to determine positivity (Table 10, FIG. 25D).

Ep-ICD Subcellular Localization Index (ESLI) Analysis in Thyroid Carcinomas

ROC curve analysis of ESLI showed an AUC of 0.9 for distinguishing PTC cases from benign thyroid nodules (FIG. 25E, Table 10), with a sensitivity of 84.8% and a specificity of 68.8%. FIG. 25F showed that ESLI distinguished aggressive PTC from the non-aggressive PTC with an AUC of 0.924, sensitivity of 88.4% and specificity of 85.5% (Table 10). FIG. 24E shows the distributions of ESLI in the three groups of thyroid tissues. An increasing trend was observed among the groups based on aggressive behavior of the tumor. Analysis of benign and malignant tissues showed that the benign group had a mean ESLI value of 4.5, whereas the non-aggressive PTC group showed a mean of 6.7 and the aggressive PTC group had a mean of 11.

Figure 26:
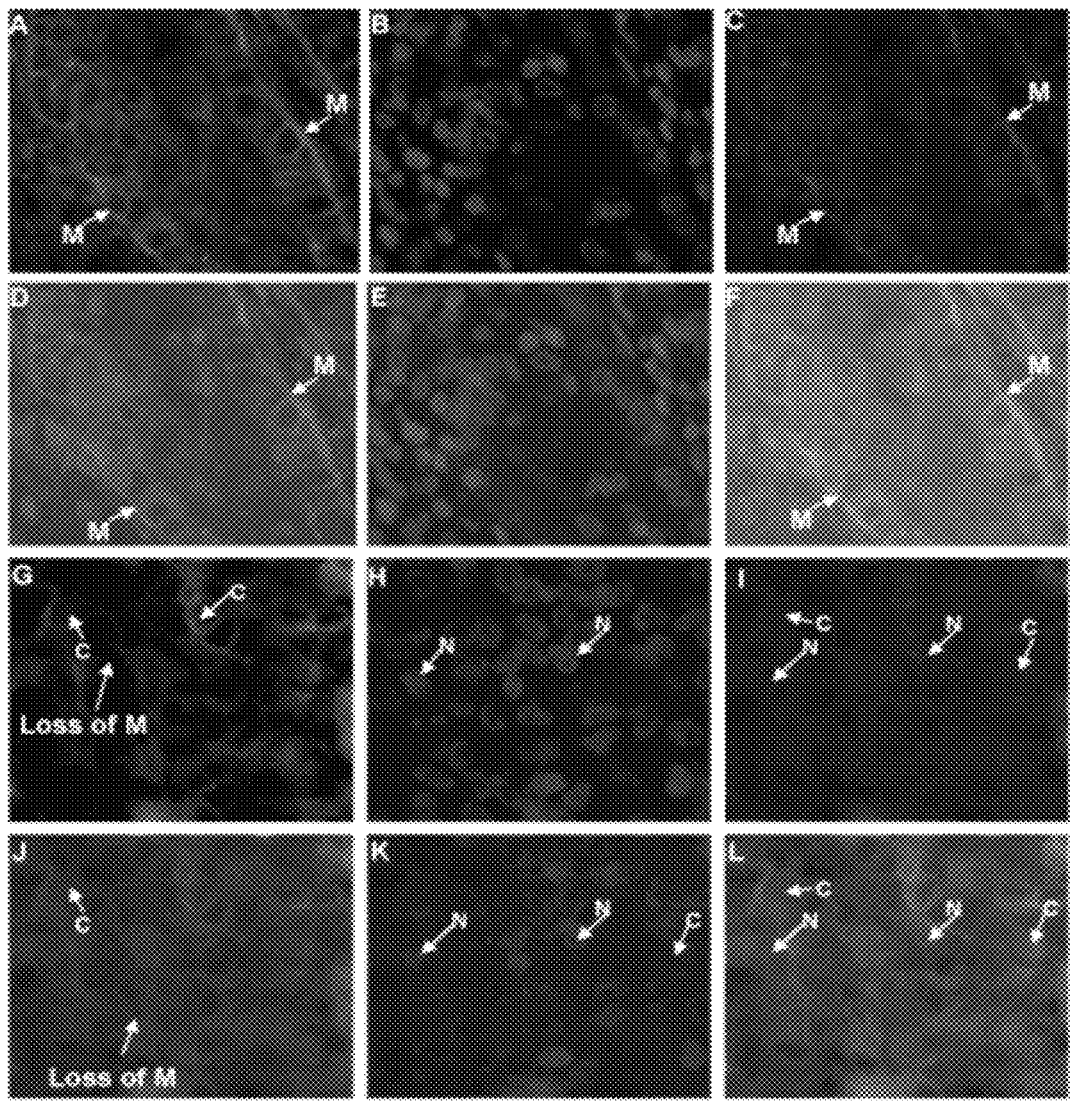
FIG. 26 is a fluorescence immunostaining with anti-EpEx and anti-Ep-ICD antibodies in aggressive and non-aggressive papillary thyroid carcinomas. Secondary antibodies are FITC-anti-mouse (green) and TRITC-anti-rabbit (red). A-F images from a non-aggressive PTC; G-L Images from an aggressive PTC. A,G) EpEx; B,H) DAPI; C, I) Ep-ICD; D) EpEx and DAPI (A & C merged); E) Ep-ICD and DAPI (B & C merged); F) EpEx, Ep-ICD, and DAPI (A, B, C merged). J) EpEx and DAPI (G & I merged); K) Ep-ICD and DAPI (H & I merged); L) EpEx, Ep-ICD, and DAPI (G, H, I merged). M, Membranous staining; C, Cytoplasm staining; N, Nuclear staining. Original magnification×400.

Immunofluorescence Analysis of Ep-ICD and EpEx Localization in Thyroid Carcinoma The aggressive and non-aggressive PTC tissues analyzed with double immunofluorescence staining with EpEx and Ep-ICD antibodies. EpEx and Ep-ICD were both detected in the plasma membrane (FIG. 26). Intense membrane expression was observed at cell-cell junctions with both EpEx and Ep-ICD domain-specific antibodies in the non-aggressive PTC cases (FIGS. 26, A and C). In addition, accumulation of Ep-ICD was observed in the cytoplasm and nuclei of aggressive PTC cases (FIGS. 26, I and K). No nuclear accumulation was observed in the non-aggressive PTC cases (FIG. 26C). The tumor cells in aggressive PTC showed absence of membranous EpEx staining (FIG. 26G). The merged images in FIGS. 26D and 26F show strong membranous staining of EpEx in non-aggressive PTC. Loss of membranous EpEx in aggressive PTC cases is shown in the merged images (FIGS. 26, J and L). The results from immunofluorescence analysis confirmed our findings of IHC analysis.

Mann Whitney U Test and Kaplan Meier Survival Analysis for ESLI

Statistical evaluation with Mann Whitney U test showed that there were significant differences in ESLI scores between the benign thyroid nodules and PTC (p<0.001) and also between aggressive PTC and non-aggressive PTC (Table 9b, p<0.001). Kaplan Meier survival analysis demonstrated significant correlation between reduced disease free survival (DFS) and ESLI positivity (p=0.039) with the mean DFS for ESLI positive being 133 months compared to 210 months for ESLI negative patients (FIG. 27).

Discussion

The prevalence of thyroid cancer is increasing worldwide, and this is due only in part to improved and earlier detection [Jemal A. et al., 2009] About 48,020 new thyroid cancer cases (7.5% increase compared to 2010) are estimated for 2011 in the United States [Jemal A. et al., 2009]. This rapid increase in thyroid cancer incidence impacts patients, oncologists and health care payers; emphasizes the crucial unmet demand for development of biomarker(s) to predict aggressive thyroid cancers for more effective disease management. The findings of the present study address this niche in biomarker development. Taking into consideration the clinical utility of Ep-ICD as a diagnostic and prognostic marker, the present study has applied a novel index of aggressiveness, ESLI, to aid in identification of aggressive PTC.

The presence of nuclear Ep-ICD is shown herein as an indicator for distinguishing aggressive PTC from the non-aggressive PTC cases. Almost all the benign thyroid tissues and non-aggressive PTC did not show immunopositivity for nuclear Ep-ICD. In contrast, a subset of aggressive PTC was immunopositive for nuclear Ep-ICD accumulation, indicating its potential as a specific biomarker for tumor aggressiveness. Importantly, it was observed the loss of membranous EpEx and accumulation of nuclear Ep-ICD to frequently occur concomitantly in aggressive PTC tumors which lends further support to regulated intramembrane proteolysis of EpCAM being an important tumorigenic event. The prominence of these findings is further underscored by the high specificity exhibited by each of these markers independently. Accumulation of nuclear Ep-ICD, cytoplasmic Ep-ICD, and/or loss of membrane EpEx occur in anaplastic thyroid carcinomas. These parameters, when considered together, account for the intracellular accumulation of Ep-ICD, which is cleaved by TACE. It is herein demonstrated that combining these parameters can improve the diagnostic and prognostic utility of these biomarkers and can serve as a novel index of aggressiveness. ESLI provides a scoring index which combines nuclear and cytoplasmic accumulation of Ep-ICD with loss of membrane EpEx. Not being bound by any one theory, one rationale for this approach is based on the hypothesis that both cytoplasmic and nuclear Ep-ICD may better account for the loss of EpEx from the membrane of cells as a result of regulated intramembrane proteolysis of EpCAM. This novel index of aggressiveness, ESLI, was able to not only identify aggressive PTC but also could distinguish it from non-aggressive PTC. A recent study examined the biological effects of EpCAM expression in thyroid cancer cells as a potentially important event in tumorigenesis [Chaves-Perez A et al., 2012]. The findings of this study showed that EpCAM directly affects cell cycle progression via its capacity to regulate the expression of cyclin D1 at the transcriptional level and depending on the direct interaction partner FHL2 (four-and-a-half LIM domains protein 2). As a result, downstream events such as phosphorylation of the retinoblastoma protein (Rb) and expression of cyclins E and A are similarly affected. In vivo, EpCAM expression strength and pattern were both positively correlated with the proliferation marker Ki67, high expression and nuclear localisation of cyclin D1, and Rb phosphorylation. Thus, EpCAM enhances cell cycle progression via the classical cyclin-regulated pathway [Chaves-Perez A et al., 2012].

Early identification of aggressive PTC could allow for a more rational therapeutic intervention in patients with more aggressive tumors that will ultimately improve treatment and management of such patients. On the other hand, it will also avoid unnecessary overtreatment for patients with non-aggressive PTC and spare exposure to potential adverse side effects from such modalities as chemotherapy and radiation exposure, while reducing the health care costs. The future diagnostic, prognostic and therapeutic application of ESLI can improve the management of PTC patients.

TABLE 1

Known Antibodies Directed Against the EpCAM

| Antibody | Epitope | Reference |
| --- | --- | --- |
| AUA1 | EGF-like domain I | Durbin et al |
| Ber-EP4 | EGF-like domain I | Latza et al |
| CO 17-1A | EGF-like domain I | Herlyn et al |
| C215 | EGF-like domain I | Bjork et al |
| ESA, EGP-2, EGP40 | Not established | Simon et al |
| FU-MK-1 | Not established | Watanabe et al |
| GA733-2 | EGF-like domain I | Szala et al |
| HEA125 | Not established | Momburg et al |
| K928 | Not established | Quak et al |
| K931 | EGF-like domain I | Copper MP |
| KSA, KS-1, KS1/4 | EGF-like domain I | Varki et al |
| MM104 | Cysteine-poor region | Schön et al |
| MH99 | EGF-like domain I | Mattes et al |
| MOC31 | EGF-like domain I | Myklebust et al |
| MT201 | Not established | Naundorf et al |
| VU-1D9 | EGF-like domain I | Tsubura et al |
| 2G8 | EGF-like domain II | Unpublished data |
| 311-1K1 | Cysteine-poor region | Helfrich et al |
| 323/A3 | EGF-like domain I | Edwards et al |

TABLE 2

Immunohistochemical Analysis of EpEx and Ep-ICD in Benign and Malignant Thyroid Tumors

| Tumour Tissue | Number Blocks (N) | Nuclear EpICD Positive (n) | Nuclear EpICD Positivity (%) | IHC Score Mean ± Std. Deviation | t-test p Value | Membrane EpEx (n) | Membrane EpEx Percentage (%) | IHC Score Mean ± Std. Deviation | t-test P Value |
| --- | --- | --- | --- | --- | --- | --- | --- | --- | --- |
| PTC | 86 | 1 | 1.2 | 0.57 ± 0.77 | P < 0.001 | 1 | 1.2 | 6.47 ± 0.66 | P < 0.001 |
| ATC | 11 | 10 | 90.9 | 4.73 ± 1.01 | | 11 | 100 | 0.61 ± 1.36 | |

Note:
A cutoff value of ≥4 was used to determine nuclear Ep-ICD positivity; a cutoff value of ≤4 scores was used to determine the loss of membrane EpEX expression.

TABLE 3

Biomarker Analysis of Nuclear Ep-ICD Expression and Membrane EpEx Expression in Filipino Thyroid Tumor Cancers

|  | AUC | Sensitivity (%) | Specificity (%) | PPV (%) | NPV (%) | Asymptotic Sig. |
|---|---|---|---|---|---|---|
| Ep-ICD Nuclear Staining Scores |  |  |  |  |  |  |
| PTC vs. ATC | 0.993 | 90.90 | 98.80 | 90.90 | 98.80 | <0.001 |
| EpEX Membrane Staining Scores |  |  |  |  |  |  |
| PTC vs. ATC | 0.914 | 100 | 98.80 | 91.67 | 100 | <0.001 |

Note:
A cutoff value of ≥4 was used to determine nuclear Ep-ICD positivity; a cutoff value of ≤4 scores was used to determine the loss of membrane EpEX expression.

TABLE 4

ROC curve for nuclear EpICD

| Area under the ROC curve | |
|---|---|
| Area | 0.9931 |
| Std. Error | 0.006375 |
| 95% confidence interval | 0.9806 to 1.006 |
| P value | <0.0001 |
| Data | |
| Controls (PTC) | 86 |
| Patients (ATC) | 11 |
| Missing Controls | 0 |
| Missing Patients | 0 |

TABLE 5

EpICD Nuclear Staining to Distinguish ATC from PTC

| Cutoff | Sensitivity % | Specificity % |
|---|---|---|
| >2.300 | 100 | 95.35 |
| >2.850 | 100 | 96.51 |
| >3.150 | 90.91 | 97.67 |
| >3.650 | 90.91 | 98.84 |
| >4.250 | 54.55 | 98.84 |
| >4.750 | 54.55 | 100 |
| >5.500 | 27.27 | 100 |

TABLE 6

ROC Curve for EpEX-Membrane

| Area under the ROC curve | |
|---|---|
| Area | 0.9989 |
| Std. Error | 0.001768 |
| 95% confidence interval | 0.9955 to 1.002 |
| P value | <0.0001 |
| Data | |
| Controls (PTC) | 86 |
| Patients (ATC) | 11 |
| Missing Controls | 0 |
| Missing Patients | 0 |

TABLE 7

EpEx membrane staining to distinguish ATC from PTC

| Cutoff | Sensitivity % | Specificity % |
|---|---|---|
| <3.300 | 90.91 | 100 |
| <3.550 | 90.91 | 98.84 |
| <4.000 | 100 | 98.84 |
| <4.550 | 100 | 97.67 |
| <4.750 | 100 | 96.51 |
| <5.050 | 100 | 95.35 |

TABLE 8

Biomarker Analysis of Nuclear Ep-ICD Expression and Membrane EpEx Expression in Filipino Thyroid Tumor Cancers

|  | AUC | Sensitivity (%) | Specificity (%) | PPV (%) | NPV (%) | Asymptotic Sig. |
|---|---|---|---|---|---|---|
| Ep-ICD Nuclear Staining Scores |  |  |  |  |  |  |
| Benign vs. Malignant Tumors | 0.703 | 33.33 | 88.89 | 87.5 | 36.3 | 0.085 |
| Nonaggressive vs. Aggressive Cancers | 1.0 | 80.00 | 100 | 100 | 83.33 | 0.000 |
| Loss of EpEX Membrane Staining Scores |  |  |  |  |  |  |
| Benign vs. Malignant Tumors | 0.857 | 28.57 | 100 | 100 | 37.50 | 0.002 |
| Nonaggressive vs. Aggressive Cancers | 0.914 | 60.00 | 100 | 100 | 73.33 | 0.001 |

Note:
A cutoff value of 4 was used to determine positivity.

TABLE 9a

IHC analysis of Ep-ICD and EpEx subcellular localization in thyroid tissues

| Thyroid Tissue | Number of cases (n) | Nuclear Ep-ICD Positive (n) | Nuclear Ep-ICD (%) | Loss of Membranous EpEx (n) | Loss of Membranous EpEx (%) | ESLI Positive (n) | ESLI Positivity (%) |
|---|---|---|---|---|---|---|---|
| Benign nodule | 16 | 2 | 12.5 | 0 | 0 | 0 | 0 |
| Non-aggressive PTC | 63 | 10 | 15.9 | 7 | 11.1 | 38 | 60.3 |
| Aggressive PTC | 121 | 85 | 70.3 | 111 | 91.7 | 118 | 97.5 |

The IHC score cut-off values for positivity were defined as ≥2 for nuclear Ep-ICD positivity; ≥5 for cytoplasmic Ep-ICD positivity and ≤5 for loss of membranous EpEx expression.
ESLI cut-off ≥6 was used to determine ESLI positivity for distinguishing PTC from benign cases; and a cut-off value of >10 was used to determine ESLI positivity for distinguishing aggressive PTCs from non-aggressive PTCs.

TABLE 9b

Comparison of IHC scores for Ep-ICD, EpEx and ESLI in thyroid tissues

| Group | Membranous EpEx (Mean ± SEM) | Cytoplasmic Ep-ICD (Mean ± SEM) | Nuclear Ep-ICD (Mean ± SEM) | ESLI (Mean ± SEM) |
|---|---|---|---|---|
| Benign | 6.8 ± 0.1 | 3.3 ± 0.4 | 0.9 ± 0.2 | 4.5 ± 0.6 |
| Malignant | 4.6 ± 0.1 | 5.1 ± 0.1 | 2.0 ± 0.1 | 9.6 ± 0.2 |
| Non-aggressive PTC | 6.1 ± 0.1 | 4.8 ± 0.1 | 1.0 ± 0.1 | 6.7 ± 0.3 |
| Aggressive PTC | 3.7 ± 0.1 | 5.3 ± 0.1 | 2.5 ± 0.1 | 11.0 ± 0.2 |

Mann-Whitney test p value for benign vs. PTC: cytoplasmic Ep-ICD p = 0.000; nuclear Ep-ICD p = 0.002 and ESLI p = 0.000.
p value for Aggressive vs. Non-aggressive PTC: cytoplasmic Ep-ICD p = 0.000; nuclear Ep-ICD p = 0.000 and ESLI p = 0.000.

TABLE 10

Receiver operating characteristic (ROC) curve analysis of Ep-ICD, EpEx and ESLI in thyroid tissues

| IHC Score | Differentiation of groups | AUC | Sensitivity (%) | Specificity (%) | PPV (%) | NPV (%) | p Value |
|---|---|---|---|---|---|---|---|
| Cytoplasmic Ep-ICD | PTC vs. Benign | 0.893 | 76.7 | 87.5 | 98.6 | 24.6 | <0.001 |
| Cytoplasmic Ep-ICD | Agressive vs. Non-agressive PT | 0.739 | 84.3 | 38.7 | 72.9 | 55.8 | <0.001 |
| Nuclear Ep-ICD | PTC vs. Benign | 0.735 | 51.6 | 87.5 | 97.9 | 13.6 | 0.002 |
| Nuclear Ep-ICD | Agressive vs. Non-agressive PT | 0.841 | 70.2 | 83.9 | 89.5 | 59.0 | <0.001 |
| ESLI | PTC vs. Benign | 0.900 | 84.8 | 68.8 | 96.9 | 28.2 | <0.001 |
| ESLI | Agressive vs. Non-agressive PT | 0.924 | 88.4 | 85.5 | 92.2 | 80.0 | <0.001 |

The IHC score cut-off values for positivity were defined as ≥2 for nuclear Ep-ICD positivity; ≥5 for cytoplasmic Ep-ICD positivity and ≤5 for loss of membranous EpEx expression.
ESLI cut-off ≥6 was used to determine ESLI positivity for distinguishing PTC from benign cases; and a cut-off value of >10 was used to determine ESLI positivity for distinguishing aggressive PTCs from non-aggressive PTCs.

FULL CITATIONS FOR PUBLICATIONS

1. Spizzo G, et al., *Breast Cancer Res Treat.* 2004; 86:207-13
2. Went P, et al., *Br J Cancer.* 2006; 94:128-35.
3. Wenqi D, et al, *J Cancer Res Clin Oncol.* 2009; 135:1277-85
4. Trzpis M, et al., *Am J Pathol.* 2007; 171:386-95.
5. Stingl J, et al, *Breast Cancer Res Treat.* 2001; 67:93-109.
6. Schmelzer E, et al, *Front Biosci.* 2008; 13:3096-100.
7. Trzpis M, et al, *Front Biosci.* 2008; 13:5050-5.
8. Al-Hajj M, et al., *Proc Natl Acad Sci USA.* 2003; 100:3983-8.
9. O'Brien C A, et al, *Nature.* 2007; 445:106-10.
10. Ricci-Vitiani L, et al, *Nature.* 2007; 445:111-5.
11. Weismann P, et al, *Neoplasma.* 2009; 56:230-8.
12. Munz M, et al, *Cancer Res.* 2009; 69:5627-9.
13. Maetzel D et al, *Nat Cell Biol.* 2009; 11:162-71.
14. Litvinov S V, et al, *J Cell Biol.* 1997; 139:1337-48
15. Münz M, et al, *Oncogene.* 2004; 23:5748-58.
16. Reis E M, et al, *Cancer Res.* 2005; 65:1693-9.
17. Jemal A, et al, 2008. *CA Cancer J Clin.* 2008; 58:71-96.
18. Pasieka J L. et al, *Curr Opin Oncol.* 2003; 15:78-83
19. Are C, Shaha A R, *Ann Surg Oncol.* 2006; 13:453-64
20. Smallridge R C, et al, *Endocr Relat Cancer.* 2009; 16:17-44.
21. Salvatore G, et al, *Cancer Res.* 2007; 67:10148-58.
22. Nappi T C, et al, *Cancer Res.* 2009; 69:1916-23.
23. Morin P J, *Bioessays.* 1999; 21:1021-30.
24. Brembeck F H, et al, *Curr Opin Genet Dev.* 2006; 16:51-9.
25. Garcia-Rostan G et al, *Am J Pathol.* 2001; 158:987-96.
26. Rocha A S, et al, *Histopathology.* 2003; 42:580-7.
27. Lantsov D, et al, *Histopathology.* 2005; 47:248-56.
28. Gujral T S, et al, *Cancer Res.* 2008; 68(5):1338-46.
29. Ensinger C, et al, *J Immunother.* 2006; 29:569-73.
30. Chaudry M A, et al, *Br J. Cancer.* 2007; 96:1013-9.
31. Ralhan R, et al, *J Proteome Res.* 2009; 8:300-9.

32. Li H, et al, *Cancer Biol Ther.* 2002; 1:621-5.
33. Ishida K, et al, *Mol Cancer.* 2007; 6:62.
34. Morin P J, et al, *Science.* 1997; 275:1787-90.
35. Ogasawara N, et al, *Histopathology.* 2006; 49:612-21.
36. Takayama T, et al, *Am J Pathol.* 1996; 148:39-46.
37. Bian Y S, et al, *Am J Clin Pathol.* 2000; 114:583-90.
38. Lustig B, Behrens J, *J Cancer Res Clin Oncol.* 2003; 129:199-221.
39. Antolovic D, et al, *BMC Biotechnol.* 2010; 10:35.
40. El-Sahwi K et al, *Mol Cancer Ther.* 2010; 9(1):57-66.
41. Raffel A, et al, *Eur J Endocrinol.* 2010; 162(2):391-8.
42. Terris B, et al, *J Hepatol.* 2010; 52(2):280-1.
43. Ralhan R et. al, *BMC Cancer* 2010, 10(1):331.
44. Jemal A et al, *CA Cancer J Clin* 2009, 59(4):225-249.
45. Sipos J A et al, *Clin Oncol (R Coll Radiol)* 2010, 22(6): 395-404.
46. Lin J D et al, *Thyroid* 2009, 19(10):1053-1059.
47. Ralhan R et al, *Mol Cell Proteomics* 2008, 7(6):1162-1173.
48. Chaves-Perez A et al, *Oncogene* 2012 Mar. 5. doi: 10.1038/onc.2012.75. [Epub ahead of print].

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the antibodies, methodologies etc. which are reported therein which might be used in connection with the invention. Nothing herein is to be construed as an admission that the invention is not entitled to antedate such disclosure by virtue of prior invention.

What is claimed is:

1. A method for diagnosing aggressive thyroid cancer in a subject, the method comprising:
   (A) determining a nuclear Ep-ICD score, a cytoplasmic Ep-ICD score and a membrane EpEx score in a thyroid tissue sample obtained from the subject, the thyroid tissue comprising cells with each cell having a nucleus, cytoplasm and a cell membrane, the step of determining comprising:
      (i) contacting the sample with: a first binding agent that specifically binds to Ep-ICD or part thereof; a first detectable label for detecting binding of the first binding agent to Ep-ICD; a second binding agent that specifically binds to EpEX or part thereof; and a second detectable label for detecting binding of the second binding agent to EpEX; wherein the first detectable label emits a detectable signal upon binding of the first binding agent to Ep-ICD and the second detectable label emits a detectable signal upon binding of the second binding agent to EpEX;
      (ii) measuring:
         (a) a first percentage, comprising the percentage of cells in the sample having Ep-ICD in the nucleus bound to the first binding agent, and assigning a first score to the first percentage according to a first scale;
         (b) a second percentage, comprising the percentage of cells in the sample having Ep-ICD in the cytoplasm bound to the first binding agent, and assigning a second score to the second percentage according to the first scale; and,
         (c) a third percentage, comprising the percentage of cells in the sample having EpEX in the cell membrane bound to the second binding agent, and assigning a third score to the third percentage according to the first scale;
      (iii) measuring:
         (a) a first intensity, comprising the intensity of the signal emitted in the nucleus by the first label, and assigning a fourth score to the first intensity according to a second scale;
         (b) a second intensity, comprising the intensity of the signal emitted in the cytoplasm by the first label and assigning a fifth score to the second intensity according to the second scale; and,
         (c) a third intensity, comprising the intensity of the signal emitted in the cell membrane by the second label, and assigning a sixth score to the third intensity according to the second scale;
      (iv) calculating the nuclear Ep-ICD score, the cytoplasmic Ep-ICD score and the membrane EpEx score by:
         (a) adding the first and fourth scores to generate the nuclear Ep-ICD score;
         (b) adding the second and fifth scores to generate the cytoplasmic Ep-ICD score; and,
         (c) adding the third and sixth scores to generate the membrane EpEX score;
   (B) calculating an Ep-ICD Subcellular Localization Index (ESLI) value for the sample, the ESLI value being a sum of the nuclear Ep-ICD score, the cytoplasmic Ep-ICD score and a membrane EpEX loss value, wherein the membrane EpEX loss value is determined by subtracting the calculated membrane EpEX score from a theoretical maximum of the membrane EpEX score;
   (C) comparing the calculated ESLI value to a reference value, wherein the control reference value is:
      (i) an ESLI value indicative of a non-aggressive thyroid cancer; or
      (ii) an ESLI value indicative of an aggressive thyroid cancer; and,
   (D) diagnosing aggressive thyroid cancer in the subject when the calculated ESLI value of the sample is greater than the reference value of (C)(i) or is greater than or equal to the reference value of (C)(ii);
   wherein: the first, second and third percentages are obtained using immunohistochemical (IHC) analysis; the first, second and third intensities are determined using immunohistochemical (IHC) analysis; and wherein at least the first binding agent is a rabbit monoclonal antibody.

2. The method of claim 1 wherein the thyroid cancer is anaplastic thyroid cancer (ATC), papillary thyroid carcinoma (PTC) or follicular thyroid carcinoma (FTC).

3. The method of claim 1 wherein the sample is obtained from a tumor tissue.

4. The method of claim 1 wherein the first and/or second binding is an antibody.

5. The method of claim 1 wherein the first and second labels are chosen from detectable radioisotopes, luminescent compounds, fluorescent compounds, enzymatic labels, biotinyl groups and predetermined polypeptide epitopes recognizable by a secondary reporter.

6. A method for diagnosing aggressive thyroid cancer in a subject, the method comprising:
(A) determining a nuclear Ep-ICD score, a cytoplasmic Ep-ICD score and a membrane EpEx score in a thyroid tissue sample obtained from the subject, the thyroid tissue comprising cells with each cell having a nucleus, cytoplasm and a cell membrane, each of said scores being determined using immunohistochemical (IHC) analyses, wherein step (A) comprises:
  (i) contacting the sample with: a first binding agent that specifically binds to Ep-ICD or part thereof; a first detectable label for detecting binding of the first binding agent to Ep-ICD; a second binding agent that specifically binds to EpEX or part thereof; and a second detectable label for detecting binding of the second binding agent to EpEX; wherein the first detectable label emits a detectable signal upon binding of the first binding agent to Ep-ICD and the second detectable label emits a detectable signal upon binding of the second binding agent to EpEX;
  (ii) determining:
    (a) a first IHC score, corresponding to the percentage of cells in the sample having Ep-ICD in the nucleus bound to the first binding agent;
    (b) a second IHC score, corresponding to the percentage of cells in the sample having Ep-ICD in the cytoplasm bound to the first binding agent; and,
    (c) a third IHC score, corresponding to the percentage of cells in the sample having EpEX in the cell membrane bound to the second binding agent;
  (iii) determining:
    (a) a fourth IHC score, corresponding to the intensity of the signal emitted in the nucleus by the first label;
    (b) a fifth IHC score, corresponding to the intensity of the signal emitted in the cytoplasm by the first label; and,
    (c) a sixth IHC score, corresponding to the intensity of the signal emitted in the cell membrane by the second label;
  (iv) calculating the nuclear Ep-ICD score, the cytoplasmic Ep-ICD score and the membrane EpEx score by:
    (a) adding the first and fourth IHC scores to generate the nuclear Ep-ICD score;
    (b) adding the second and fifth IHC scores to generate the cytoplasmic Ep-ICD score; and,
    (c) adding the third and sixth IHC scores to generate the membrane EpEX score;
(B) calculating an Ep-ICD Subcellular Localization Index (ESLI) value for the sample, the ESLI value being a sum of the nuclear Ep-ICD score, the cytoplasmic Ep-ICD score and a membrane EpEx loss value, wherein the membrane EpEX loss value is determined by subtracting the calculated membrane EpEX score from a theoretical maximum of the membrane EpEX score;
(C) comparing the calculated ESLI value to a reference value, wherein the reference value is:
  (i) an ESLI value indicative of a non-aggressive thyroid cancer; or
  (ii) an ESLI value indicative of an aggressive thyroid cancer; and,
(D) diagnosing aggressive thyroid cancer in the subject when the calculated ESLI value of the sample is greater than the reference value of (C)(i) or is greater than or equal to the reference value of (C)(ii);
wherein at least the first binding agent is a rabbit monoclonal antibody.

7. The method of claim 6, wherein the thyroid cancer is anaplastic thyroid cancer (ATC), papillary thyroid carcinoma (PTC) or follicular thyroid carcinoma (FTC).

8. The method of claim 6 wherein the sample is obtained from a tumor tissue.

9. The method of claim 6 wherein the second binding is an antibody.

10. The method of claim 6 wherein the first and second labels are chosen from detectable radioisotopes, luminescent compounds, fluorescent compounds, enzymatic labels, biotinyl groups and predetermined polypeptide epitopes recognizable by a secondary reporter.

11. A method for detecting abnormal subcellular localization of Ep-ICD and EpEx in a thyroid tissue sample obtained from a subject, the thyroid tissue comprising cells having a nucleus, cytoplasm and a cell membrane, the method comprising:
(A) determining a nuclear Ep-ICD score, a cytoplasmic Ep-ICD score and a membrane EpEx score for cells in the thyroid tissue sample, wherein step (A) comprises:
  (i) contacting the sample with: a first binding agent that specifically binds to Ep-ICD or part thereof; a first detectable label for detecting binding of the first binding agent to Ep-ICD; a second binding agent that specifically binds to EpEX or part thereof; and a second detectable label for detecting binding of the second binding agent to EpEX; wherein the first detectable label emits a detectable signal upon binding of the first binding agent to Ep-ICD and the second detectable label emits a detectable signal upon binding of the second binding agent to EpEX;
  (ii) measuring:
    (a) a first percentage, comprising the percentage of cells in the sample having Ep-ICD in the nucleus bound to the first binding agent, and assigning a first score to the first percentage according to a first scale;
    (b) a second percentage, comprising the percentage of cells in the sample having Ep-ICD in the cytoplasm bound to the first binding agent, and assigning a second score to the second percentage according to the first scale; and,
    (c) a third percentage, comprising the percentage of cells in the sample having EpEX in the cell membrane bound to the second binding agent, and assigning a third score to the third percentage according to the first scale;
  (iii) measuring:
    (a) a first intensity, comprising the intensity of the signal emitted in the nucleus by the first label, and assigning a fourth score to the first intensity according to a second scale;
    (b) a second intensity, comprising the intensity of the signal emitted in the cytoplasm by the first label and assigning a fifth score to the second intensity according to the second scale; and,
    (c) a third intensity, comprising the intensity of the signal emitted in the cell membrane by the second label, and assigning a sixth score to the third intensity according to the second scale;
(iv) calculating the nuclear Ep-ICD score, the cytoplasmic Ep-ICD score and the membrane EpEx score by:
   (a) adding the first and fourth scores to generate the nuclear Ep-ICD score;
   (b) adding the second and fifth scores to generate the cytoplasmic Ep-ICD score; and,
   (c) adding the third and sixth scores to generate the membrane EpEX score;
(B) calculating an Ep-ICD Subcellular Localization Index (ESLI) value for the sample, the ESLI value being a sum of the nuclear Ep-ICD score, the cytoplasmic Ep-ICD score and a membrane EpEx loss value, wherein the membrane EpEX loss value is determined by subtracting the calculated membrane EpEX score from a theoretical maximum of the membrane EpEX score;
(C) comparing the calculated ESLI value to a reference value, wherein the reference value is:
   (i) an ESLI value indicative of a normal subcellular localization of Ep-ICD and EpEx; or
   (ii) an ESLI value indicative of an abnormal subcellular localization of Ep-ICD and EpEx; and,
(D) detecting abnormal subcellular localization of Ep-ICD and EpEx in the thyroid tissue sample when the calculated ESLI value of the sample is greater than the reference value of (C)(i) or is greater than or equal to the reference value of (C)(ii);
wherein: the first, second and third percentages are obtained using immunohistochemical (IHC) analysis; the first, second and third intensities are determined using immunohistochemical (IHC) analysis; and wherein at least the first binding agent is a rabbit monoclonal antibody.

12. The method of claim 11 wherein the sample is obtained from a tumor tissue.

13. The method of claim 12 wherein the second binding is an antibody.

14. The method of claim 12 wherein the first and second labels are chosen from detectable radioisotopes, luminescent compounds, fluorescent compounds, enzymatic labels, biotinyl groups and predetermined polypeptide epitopes recognizable by a secondary reporter.

* * * * *

UNITED STATES PATENT AND TRADEMARK OFFICE
CERTIFICATE OF CORRECTION

PATENT NO. : 9,110,065 B2
APPLICATION NO. : 13/464494
DATED : August 18, 2015
INVENTOR(S) : Paul Walfish and Ranju Ralhan It is certified that error appears in the above-identified patent and that said Letters Patent is hereby corrected as shown below:

In the claims

Column 81 line 3 Claim 4: Delete "first and/or".

Column 81 lines 3-4 Claim 4: After "second binding" insert --agent--.

Column 82 line 14 Claim 9: After "second binding" insert --agent--.

Column 84 line 14 Claim 13: After "second binding" insert --agent--.

Signed and Sealed this
Twenty-second Day of March, 2016

Michelle K. Lee
*Director of the United States Patent and Trademark Office*